(12) United States Patent
Josien et al.

(10) Patent No.: US 7,998,958 B2
(45) Date of Patent: Aug. 16, 2011

(54) SUBSTITUTED N-ARYLSULFONYLHETEROCYCLIC AMINES AS GAMMA-SECRETASE INHIBITORS

(75) Inventors: Hubert B. Josien, Jersey City, NJ (US); John W. Clader, Cranford, NJ (US); Thomas A. Bara, Scotch Plains, NJ (US); Ruo Xu, Watchung, NJ (US); Hongmei Li, Warren, NJ (US); Dmitri A. Pissarnitski, Scotch Plains, NJ (US); Zhiqiang Zhao, Scotch Plains, NJ (US)

(73) Assignee: Schering Corporation, Rahway, NJ (US)

( * ) Notice: Subject to any disclaimer, the term of this patent is extended or adjusted under 35 U.S.C. 154(b) by 0 days.

(21) Appl. No.: 12/633,311

(22) Filed: Dec. 8, 2009

(65) Prior Publication Data
US 2010/0093695 A1 Apr. 15, 2010

Related U.S. Application Data

(62) Division of application No. 11/168,797, filed on Jun. 28, 2005, now Pat. No. 7,763,613.

(60) Provisional application No. 60/584,010, filed on Jun. 30, 2004.

(51) Int. Cl.
*A61K 31/535* (2006.01)
*C07D 413/14* (2006.01)

(52) U.S. Cl. ...................... 514/234.5; 544/116
(58) Field of Classification Search ............... 514/234.5; 544/116
See application file for complete search history.

(56) References Cited

U.S. PATENT DOCUMENTS

| | | | |
|---|---|---|---|
| 5,646,167 A | 7/1997 | MacPherson et al. |
| 6,683,091 B2 | 1/2004 | Asberom et al. |
| 7,115,634 B2 | 10/2006 | Thurieau et al. |
| 7,122,675 B2 | 10/2006 | Josien et al. |
| 7,208,602 B2 | 4/2007 | Pissarnitski et al. |
| 7,256,186 B2 | 8/2007 | Pissarntiski et al. |
| 7,368,457 B2 | 5/2008 | Josien |
| 2004/0171614 A1 | 9/2004 | Pissarnitski et al. |
| 2005/0239796 A1 | 10/2005 | Thurieau et al. |
| 2006/0004004 A1 | 1/2006 | Asberom et al. |
| 2006/0009467 A1 | 1/2006 | Josien et al. |
| 2006/0100427 A1 | 5/2006 | Pissarnitski et al. |
| 2007/0197581 A1 | 8/2007 | Asberom et al. |

FOREIGN PATENT DOCUMENTS

| | | |
|---|---|---|
| FR | 2802206 | 6/2001 |
| JP | 4-247081 | 9/1992 |
| WO | WO 99/62888 | * 12/1999 |
| WO | WO 00/50391 | 8/2000 |
| WO | WO 01/81308 | 11/2001 |
| WO | WO 02/02554 | 1/2002 |
| WO | WO 02/24649 | 3/2002 |
| WO | WO 03/066592 | 8/2003 |
| WO | WO 03/216380 | 11/2003 |
| WO | WO 2004/101562 | 11/2004 |
| WO | WO 2005/028440 | 3/2005 |

OTHER PUBLICATIONS

Bancher, C., et al., "Low prevalence of apolipoprotein E ∈4 allele in the neurofibrillary tangle predominant form of senile dementia", Springer, 128:46764 (1997).
Beal, M., et al., "Degnerative Diseases of the Nervous System", Harrison's Principals of Internal Medicine, 12th Edition, 1991.
Butcher, J., "Alzheimer's amyloid hypothesis gains support", Science and Medicine, The Lancet, vol. 356, p. 2161, (2000).
Chui, et. al., "Transgenic mice with Alzheimer presenilin 1 mutations show accelerated neurodegeneration without amyloid", Nature America, 131:86371 (1999).
Fortini, M., "γ-Secretase-mediated Proteolysis in Cell-Surface-Receptor Signalling", Nature Reviews/Mol. Cell. Biol. vol. 3 pp. 673-684 (2002).
Goto, G., et al., "Preparation of five-membered heterocyclic amide derivatives" 118:213064 (1993).
Hansen, H., et al., "Multistep Solution-Phase Parallel Synthesis of Spiperone Analogues", Bioorganic & Medicinal Chemistry Letters, vol. 10, pp. 2435-2439 (2000).
Hardy, J., et al., "The Amyloid Hypothesis of Alzheimer's Disease: Progress and Problems on the Road to Therapeutics", Science's Compass Review, vol. 297 pp. 353-356 (2002).
Hock, C., et al., "Antibodies against β-Amyloid Slow Cognitive Decline in Alzheimer's Diesease", Neuron, vol. 38, pp. 547-554 (2003).
Hooper, N., et al., "Membrane Protein Secretases", Portland Press, 126:196601 (1997).
Leblanc., A., et al., "Production of Alzheimer 4kDa β-amyloid peptide requires the C-terminal cytosolic domain of the amyloid precursor protein", Academic, 121:298388 (1994).
MacPherson, L., et al., "Arylsulfonamido-substituted hydroxamic acids", U.S., 31 pp., Cont.-in-part of U.S. 5,552,419, 127:162116 (1997).

(Continued)

*Primary Examiner* — Rebecca Anderson
(74) *Attorney, Agent, or Firm* — Susan L. Hess; Henry C. Jeanette; Gerard M. Devlin

(57) ABSTRACT

Disclosed are novel gamma secretase inhibitors of the formula:

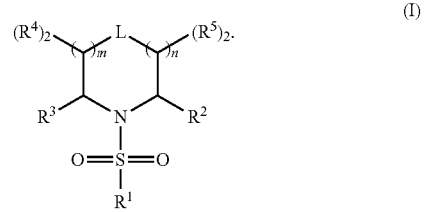

(I)

Also disclosed are methods for inhibiting gamma secretase, for treating one or more neurodegenerative diseases, for inhibiting the deposition of beta amyloid protein, and for treating Alzheimer's disease using the compounds of formula (I).

16 Claims, No Drawings

OTHER PUBLICATIONS

Nielsen, S., et al., "Novel Potent Ligands for the Central Nicotinic Acetylcholine Receptor: Synthesis, Receptor Binding, and 3D-QSAR Analysis", J. Med. Chem. vol. 43, No. 11, pp. 2217-2226 (2000).

Obici, L., et al., "A novel AβPP Mutation Exclusively Associated with Cerebral Amyloid Angiopathy", Ann. of Neurology, vol. 58, No. 4, pp. 639-644 (2005).

Pear, W., et. al., "T cell acute lymphoblastic leukemia/lymphoma: a human cancer commonly associated with aberrant NOTCH1 signaling", Curr. Opin. Hematology, vol. 11(6), pp. 426-433 (2004).

Takefumi, M., et al., Reaction of N-Benzenesulfonyl-9-Azabicyclo-[3.3.1]Nona-2,6-Diene with Diborane: Failure of Cyclic Hydroboration in the Intramolecularly Faced Diene System, *Heterocycles* vol. 6, No. 4 (1977) 469-474.

Wang, H., "High-performance liquid chromatographic analysis of 6β-acetoxynortropane eye drops", 116:91540 (1992).

Xia, W., "Relationship between presenilinase and γ-secretase", Prous Science, 139:357800 (2003).

PCT International Search Report dated Sep. 28, 2005 for PCT Application No. PCT/US2005/011456.

PCT International Search Report dated Dec. 22, 2004 for PCT Application No. PCT/US2004/014671.

English abstract for FR2802206, Jun. 15, 2001.

English abstract for JP 4-247081, Sep. 3, 1992.

STN Registry No. 401648-55-3, Mar. 18, 2002.

Kreier, A., et al., Asymmetric Synthesis of Stereodefined 7-(Alk-1-enyl)-5,6,7,8-tetrahydronaphthalene-2-carboxylic Acids and Their Precursors, Bearing a Polar Group in the 8-Position, by the 3-Sulfonyl-1,3-oxazolidine Method, Synthesis 2000, No. 10, 1391-1402.

Steif, F., et al., Enantio- and Diastereoselective Synthesis of (Protected) 2-Formyl-and 2-(Hydroxymethyl)-1-phenylalkane-1,3-diols from Chiral 2-Methoxy-3-tosyl-1,3-oxazolidines by Subsequent Asymmetric Formylation and Aldolization, Synthesis 2000, No. 5, 743-753.

Almstead, N., et al., Design, Synthesis, and Biological Evaluation of Potent Thiazine- and Thiazepine-Based Matrix Metalloproteinase Inhibitors, J. Med. Chem. 1999, 42, 4547-4562.

Teall, M., et al., Aryl sulfones: a new class of γ-secretase inhibitors, Bioorganic & Medicinal Chemistry Letters 15 (2005) 2685-2688.

PCT International Search Report dated Nov. 2, 2006, for corresponding PCT Application No. PCT/US2005/023187.

* cited by examiner

SUBSTITUTED N-ARYLSULFONYLHETEROCYCLIC AMINES AS GAMMA-SECRETASE INHIBITORS

This application is a divisional of Ser. No. 11/168,797, filed Jun. 28, 2005, now U.S. Pat. No. 7,763,613 issued Jul. 27, 2010, which in turn claims the benefit of U.S. Provisional Application Ser. No. 60/584,010, filed Jun. 30, 2004.

BACKGROUND

WO 00/50391, published Aug. 13, 2000, discloses compounds having a sulfonamide moiety that are useful for the treatment and prevention of Alzheimer's Disease and other diseases relating to the deposition of amyloid protein.

In view of the present interest in the treatment or prevention of neurodegenerative diseases, such as Alzheimer's Disease, a welcome contribution to the art would be compounds for use in such treatment or prevention. This invention provides such a contribution.

SUMMARY OF THE INVENTION

This invention provides compounds that are inhibitors (e.g., antagonists) of gamma-secretase (also termed "γ-secretase") and have the formula I:

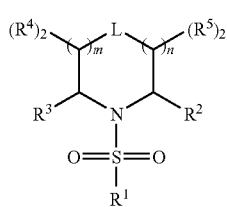

or a pharmaceutically acceptable salt and/or solvate thereof, wherein:

L is —O—, —N($R^6$)—, —S—, —S(O)—, or —S($O_2$)—;

$R^1$ is selected from the group consisting of unsubstituted aryl, aryl substituted with one or more substituents $R^7$ which can be the same or different, unsubstituted heteroaryl, and heteroaryl substituted with one or more substituents $R^7$ which can be the same or different;

$R^2$ is selected from the group consisting of alkyl, alkyl substituted with one or more substituents $R^7$ which can be the same or different, —C(O)—Y, —X—C(O)—Y, -alkylene-X—C(O)—Y, -alkylene-C(O)—Y, -alkylene-cycloalkylene-X—C(O)—Y, alkylene-cycloalkylene-C(O)—Y, -cycloalkylene-alkylene-X—C(O)—Y, -cycloalkylene-alkylene-C(O)—Y, -cycloalkylene-alkylene-C(O)—Y substituted on the alkylene moiety with one or more hydroxy groups, -cycloalkylene-X—C(O)—Y, -cycloalkylene-C(O)—Y, -alkylene-cycloalkylene-alkylene-X—C(O)—Y, -alkylene-cycloalkylene-alkylene-C(O)—Y, unsubstituted aryl, aryl substituted with one or more substituents $R^7$ which can be the same or different, unsubstituted heteroaryl, and heteroaryl substituted with one or more substituents $R^7$ which can be the same or different;

$R^3$ is selected from the group consisting of unsubstituted aryl, aryl substituted with one or more substituents $R^7$ which can be the same or different, unsubstituted heteroaryl, heteroaryl substituted with one or more substituents $R^7$ which can be the same or different, unsubstituted alkyl, alkyl substituted with one or more substituents $R^7$ which can be the same or different, unsubstituted cycloalkyl, cycloalkyl substituted with one or more substituents $R^7$ which can be the same or different, alkylene-cycloalkyl, alkylene-cycloalkyl independently substituted on the cycloalkyl moiety with one or more substituents $R^7$, unsubstituted arylalkyl, arylalkyl optionally independently substituted on the aryl moiety with one or more substituents $R^7$ which can be the same or different, unsubstituted arylcycloalkyl, arylcycloalkyl independently substituted on the aryl moiety with one or more substituents $R^7$ which can be the same or different, unsubstituted heteroarylalkyl, heteroarylalkyl independently substituted on the heteroaryl moiety with one or more substituents $R^7$ which can be the same or different, unsubstituted heteroarylcycloalkyl, heteroarylcycloalkyl independently substituted on the heteroaryl moiety with one or more substituents $R^7$ which can be the same or different, unsubstituted arylheterocycloalkyl, arylheterocycloalkyl independently substituted on the aryl moiety with one or more substituents $R^7$ which can be the same or different, and unsubstituted alkoxyalkyl;

each $R^4$ and $R^5$ is independently selected from the group consisting of H, alkyl, and alkyl independently substituted with one or more substituents $R^7$ which can be the same or different; or $R^3$ and $R^4$ together with the carbon atoms to which they are shown attached form a 4- to 8-membered cycloalkyl or heterocycloalkyl ring;

$R^6$ is selected from the group consisting of H, alkyl, alkyl independently substituted with one or more substituents $R^7$ which can be the same or different, unsubstituted aryl, and aryl independently substituted with one or more substituents $R^7$ which can be the same or different;

$R^7$ is selected from the group consisting of halo, —$CF_3$, —OH, alkyl, alkyl substituted with 1 to 4 hydroxy groups, —O-alkyl, —$OCF_3$, —CN, —NH(alkyl), —N(alkyl)$_2$, —NH(aryl), —N(aryl)$_2$, —N(aryl)(alkyl), —C(O)O-alkyl, -alkylene-NH(alkyl), -alkylene-N(alkyl)$_2$, -alkylene-NH(aryl), -alkylene-N(aryl)$_2$, -alkylene-N(aryl)(alkyl),), —NHC(O)-alkyl, —N(alkyl)C(O)-alkyl, —N(aryl)C(O)-alkyl, —NHC(O)-aryl, —N(alkyl)C(O)-aryl, —N(aryl)C(O)-aryl, —NHC(O)-heteroaryl, —N(alkyl)C(O)-heteroaryl, —N(aryl)C(O)-heteroaryl, —NHC(O)—$NH_2$, —NHC(O)—NH(alkyl), —NHC(O)—N(alkyl)$_2$, —NHC(O)—NH(aryl), —NHC(O)—N(aryl)$_2$, —NHC(O)—N(alkyl)(aryl), —N(alkyl)C(O)—$NH_2$, —N(alkyl)C(O)—NH(alkyl), —N(alkyl)C(O)—N(alkyl)$_2$, —N(alkyl)C(O)—NH(aryl), —N(alkyl)C(O)—N(aryl)$_2$, —N(alkyl)C(O)—N(alkyl)(aryl), —N(aryl)C(O)—$NH_2$, —N(aryl)C(O)—NH(alkyl), —N(aryl)C(O)—N(alkyl)$_2$, —N(aryl)C(O)—NH(aryl), —N(aryl)C(O)—N(aryl)$_2$, and —N(aryl)C(O)—N(alkyl)(aryl);

$R^8$ and $R^9$ are each independently selected from the group consisting of H, alkyl, cycloalkyl, arylalkyl, heteroarylalkyl,

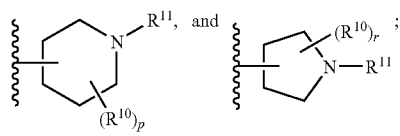

each $R^{10}$ is independently selected from the group consisting of H, —OH, alkyl, alkyl substituted with 1 to 4 hydroxy groups, —O-alkyl, —O-alkyl substituted with 1 to 4 hydroxy groups, cycloalkyl, cycloalkyl substituted with 1 to 4 hydroxy groups, —C(O)O-alkyl, -alkylene-C(O)—OH, unsubstituted heterocycloalkyl, heterocycloalkyl substituted with one or more groups $R^7$, -alkylene-C(O)—$NH_2$, -alkylene-C(O)—NH(alkyl), -alkylene-C(O)—N(alkyl)$_2$, -alkylene-C(O)—NH(aryl), -alkylene-C(O)—N(aryl)$_2$, -alkylene-C(O)—N(alkyl)(aryl), —C(O)—$NH_2$, —C(O)—NH(alkyl), —C(O)—N(alkyl)$_2$, —C(O)—NH(aryl), —C(O)—N(aryl)$_2$, —C(O)—N(alkyl)(aryl), -alkylene-C(O)—O-cycloalkyl, —O-cycloalkyl, and —O-cycloalkyl substituted with 1 to 4 hydroxy groups; or two $R^{10}$ groups together with the ring carbon atoms to which they are shown attached form a 4- to 7-membered cycloalkyl or heterocycloalkyl ring; or two $R^{10}$ groups together with the ring carbon atom to which they are attached form a carbonyl group;

$R^{11}$ is H, alkyl, alkyl substituted with 1 to 4 hydroxy groups, cycloalkyl, cycloalkyl substituted with 1 to 4 hydroxy groups, arylalkyl, heteroarylalkyl, —C(O)O-alkyl, —C(O)-alkyl, —C(O)-alkyl wherein said alkyl moiety is substituted with one or more hydroxyl groups, —C(O)-cycloalkyl, —C(O)—$NH_2$, —C(O)—NH(alkyl), —C(O)—N(alkyl)$_2$, —C(O)—NH(aryl), —C(O)—N(aryl)$_2$, —C(O)—N(alkyl)(aryl), —C(O)-alkylene-$NH_2$, —C(O)-alkylene-NH(alkyl), —C(O)-alkylene-N(alkyl)$_2$, —C(O)-alkylene-NH(aryl), —C(O)-alkylene-N(aryl)$_2$, —C(O)-alkylene-N(alkyl)(aryl), —S($O_2$)-alkyl, -alkylene-C(O)—OH, alkylene-O-alkylene-OH, unsubstituted aryl, aryl independently substituted with one or more substituents $R^7$, unsubstituted heteroaryl, heteroaryl independently substituted with one or more substituents $R^7$, and -alkylene-C(O)O-alkyl;

X is selected from the group consisting of —O—, —N($R^6$)—, —O-alkylene- and -alkylene-O—;

Y is selected from the group consisting of —$NR^8R^9$, —N($R^6$)—($CH_2$)$_b$—$NR^8R^9$ wherein b is an integer of from 2 to 6, unsubstituted aryl, aryl independently substituted with one or more substituents $R^7$ which may be the same or different, unsubstituted heteroaryl, heteroaryl independently substituted with one or more substituents $R^7$ which may be the same or different, alkyl, cycloalkyl, unsubstituted arylalkyl, arylalkyl independently substituted on the aryl moiety with one or more substituents $R^7$ which may be the same or different, unsubstituted arylcycloalkyl, arylcycloalkyl independently substituted on the aryl moiety with one or more substituents $R^7$ which may be the same or different, unsubstituted heteroarylalkyl, heteroarylalkyl independently substituted on the heteroaryl moiety with one or more substituents $R^7$ which may be the same or different, unsubstituted heteroarylcycloalkyl, heteroarylcycloalkyl independently substituted on the heteroaryl moiety with one or more substituents $R^7$ which may be the same or different, unsubstituted heterocycloalkyl, heterocycloalkyl independently substituted with one or more substituents $R^7$ which may be the same or different, unsubstituted arylheterocycloalkyl, and arylheterocycloalkyl independently substituted on the aryl moiety with one or more substituents $R^7$ which may be the same or different; or Y is selected from the group consisting of:

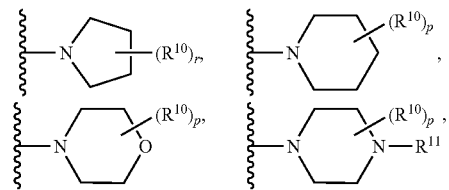

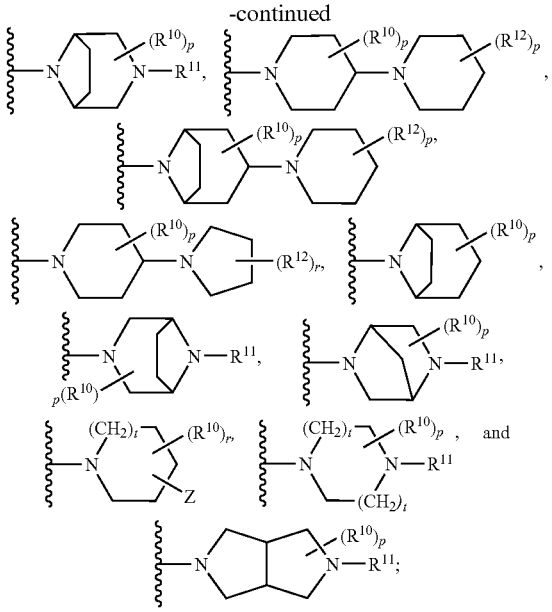

Z is selected from the group consisting of H, —OH, —O-alkyl, unsubstituted heterocycloalkyl, heterocycloalkyl optionally independently substituted with one or more substituents $R^{14}$ which may be the same or different, —$NR^8R^9$, —$NR^8R^{13}$, unsubstituted benzo-fused heterocycloalkyl, and benzo-fused heterocycloalkyl optionally independently substituted on the benzo- or heterocycloalkyl moiety with one or more substituents $R^{14}$ which may be the same or different;

each $R^{12}$ is independently H or alkyl;

$R^{13}$ is selected from the group consisting of H, unsubstituted heterocycloalkyl, heterocycloalkyl independently substituted with one or more substituents $R^{14}$ which may be the same or different, unsubstituted arylalkyl, arylalkyl independently substituted on the aryl moiety with one or more substituents $R^{14}$ which may be the same or different, unsubstituted heteroarylalkyl, heteroarylalkyl optionally independently substituted on the heteroaryl moiety with one or more substituents $R^{14}$ which may be the same or different, unsubstituted cycloalkyl, cycloalkyl optionally independently substituted with one or more substituents $R^{14}$ which may be the same or different, unsubstituted -alkylene-cycloalkyl, -alkylene-cycloalkyl independently substituted on the cycloalkyl moiety with one or more substituents $R^{14}$ which may be the same or different, unsubstituted -alkylene-heterocycloalkyl, and -alkylene-heterocycloalkyl independently substituted on the heterocycloalkyl moiety with one or more substituents $R^{14}$ which may be the same or different;

$R^{14}$ is selected from the group consisting of halo, —$CF_3$, —OH, —O-alkyl, —$OCF_3$, —CN, —$NR^8R^9$, —C(O)-alkyl, —C(O)-aryl, —C(O)—$NR^8R^9$, —C(O)O-alkyl, -alkylene-$NR^8R^9$, -alkylene-C(O)O-alkyl, —N($R^8$)C(O)-alkyl, —N($R^8$)C(O)-aryl, —N($R^8$)C(O)-heteroaryl, —N($R^8$)C(O)—$NR^8R^9$, piperidinyl, pyrrolidinyl, aryl, heteroaryl, and —O—$CH_2$—$CH_2$—O—, wherein both oxygen atoms of said —O—$CH_2$—$CH_2$—O— are bound to the same carbon atom and with the proviso that aryl and heteroaryl moieties are not substituted with said —O—$CH_2$—$CH_2$—O— group;

m and n can be the same or different and are integers of from 0 to 3;

p is an integer of from 1 to 4;

r is an integer of from 1 to 3; and t is an integer of from 0 to 2.

This invention also provides a pharmaceutical composition comprising an effective amount of one or more compounds of Formula I and at least one pharmaceutically acceptable carrier.

This invention also provides a method for inhibiting gamma-secretase comprising administering an effective (i.e., therapeutically effective) amount of one or more compounds of formula I to a patient in need of treatment.

This invention also provides a method of treating one or more neurodegenerative diseases comprising administering an effective (i.e., therapeutically effective) amount of one or more compounds of formula I to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of one or more compounds of formula I to a patient in need of treatment.

This invention also provides a method of treating Alzheimer's disease comprising administering an effective (i.e., therapeutically effective) amount of one or more compounds of formula I to a patient in need of treatment.

DETAILED DESCRIPTION OF THE INVENTION

In a first embodiment, the present invention is directed to compounds of Formula I, or pharmaceutically acceptable salts and/or solvates thereof, as described herein above.

In another embodiment of the compounds of Formula I, $R^1$ is aryl or heteroaryl substituted with one or more substituents $R^7$;

$R^2$ is —$(C_0\text{-}C_6)$alkylene-$(C_3\text{-}C_6)$cycloalkylene-$(C_0\text{-}C_6)$alkylene-X—C(O)—Y, —$(C_0\text{-}C_6)$alkylene-$(C_3\text{-}C_6)$cycloalkylene-$(C_0\text{-}C_6)$alkylene-C(O)—Y, or —$(C_3\text{-}C_6)$cycloalkylene-$(C_1\text{-}C_6)$alkylene-C(O)—Y substituted on the alkylene moiety with one or more hydroxy groups;

$R^3$ is aryl alkyl, or cycloalkyl, each of which may be unsubstituted or substituted with one or more substituents $R^7$ which can be the same or different;

L is —O— or —N($R^6$)—;

X is —O— or —N($R^6$)—; and m and n are independently 0, 1, or 2, with the proviso that m+n is 1 or 2.

In another embodiment of the compounds of Formula I, m and n are each 1;

each $R^4$ and $R^5$ is H; and $R^1$ is phenyl substituted with one or more substituents $R^7$.

In another embodiment of the compounds of Formula I, $R^1$ is phenyl, pyridyl, or thiophenyl substituted with one or more substituents $R^7$;

$R^2$ is —$(C_1\text{-}C_6)$alkylene-X—C(O)—Y, —$(C_3\text{-}C_6)$cycloalkylene-X—C(O)—Y, —$(C_3\text{-}C_6)$cycloalkylene-$(C_1\text{-}C_6)$alkylene-C(O)—Y, or —$(C_3\text{-}C_6)$cycloalkylene-$(C_1\text{-}C_6)$alkylene-C(O)—Y substituted on the $(C_1\text{-}C_6)$alkylene moiety with one or more hydroxy groups;

$R^3$ is phenyl ethyl, n-propyl, iso-propyl, cyclopropyl, or —$CH_2$-cyclopropyl, each of which may be unsubstituted or substituted with one or more substituents $R^7$ which can be the same or different;

L is —O— or —N($R^6$)—;

X is —O— or —N($R^6$)—; and m and n are each 1.

In another embodiment of the compounds of Formula I, L is —O—.

In another embodiment of the compounds of Formula I, L is —NH—.

In another embodiment of the compounds of Formula I, L is —N(($C_1\text{-}C_6$)alkyl).

In another embodiment of the compounds of Formula I, L is —S—.

In another embodiment of the compounds of Formula I, L is —S(O)—.

In another embodiment of the compounds of Formula I, L is —$S(O)_2$—.

In another embodiment of the compounds of Formula I, $R^2$ is selected from the group consisting of —$(C_1\text{-}C_6)$alkylene-X—C(O)—Y, —$(C_0\text{-}C_6)$alkylene-$(C_3\text{-}C_6)$cycloalkylene-$(C_0\text{-}C_6)$alkylene-X—C(O)—Y, and —$(C_0\text{-}C_6)$alkylene-$(C_3\text{-}C_6)$cycloalkylene-$(C_0\text{-}C_6)$alkylene-C(O)—Y.

In another embodiment of the compounds of Formula I, $R^2$ is —$CH_2$—X—C(O)—Y.

In another embodiment of the compounds of Formula I, $R^2$ is —$CH_2$—O—C(O)—Y.

In another embodiment of the compounds of Formula I, $R^2$ is -1,1-cyclopropylene-O—C(O)—Y.

In another embodiment of the compounds of Formula I, $R^2$ is -1,1-cyclopropylene-$CH_2$—C(O)—Y or -1,1-cyclopropylene-CH(OH)—C(O)—Y.

In another embodiment of the compounds of Formula I, $R^3$ is phenyl substituted with one or more substituents $R^7$.

In another embodiment of the compounds of Formula I, $R^3$ is cycloalkyl.

In another embodiment of the compounds of Formula I, $R^3$ is cyclopropyl.

In another embodiment of the compounds of Formula I, $R^3$ is alkyl.

In another embodiment of the compounds of Formula I, $R^3$ is methyl.

In another embodiment of the compounds of Formula I, $R^3$ is ethyl.

In another embodiment of the compounds of Formula I, $R^3$ is propyl.

In another embodiment of the compounds of Formula I, $R^3$ is iso-propyl.

In another embodiment of the compounds of Formula I, $R^3$ is n-propyl.

In another embodiment of the compounds of Formula I, $R^3$ is 3,5-difluorophenyl.

In another embodiment of the compounds of Formula I, $R^3$ is cyclopropyl.

In another embodiment of the compounds of Formula I, $R^3$ is —$CH_2$-cyclopropyl.

In another embodiment of the compounds of Formula I, $R^3$ is —$CH_2$-(2,2-difluorocyclopropyl).

In another embodiment of the compounds of Formula I, $R^1$ is 4-chlorophenyl.

In another embodiment of the compounds of Formula I, $R^1$ is p-tolyl.

In another embodiment of the compounds of Formula I, Y is selected from the group consisting of —$NR^8R^9$,

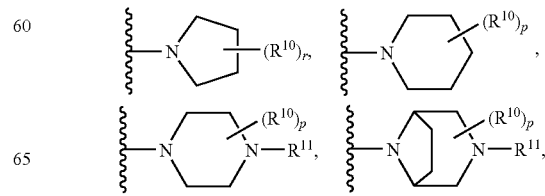

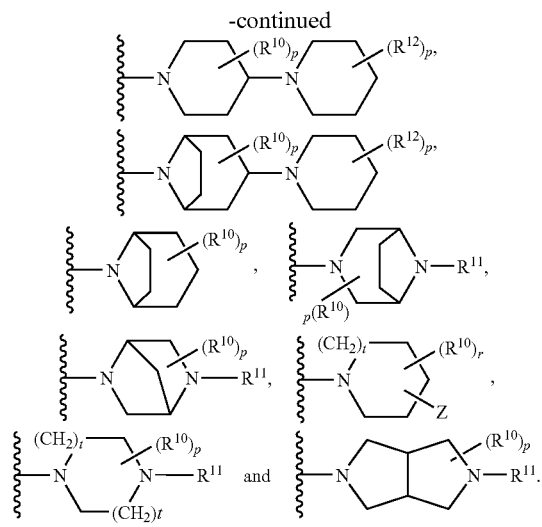

In yet another embodiment of the compounds of Formula I, each $R^4$ is independently H or methyl.

In yet another embodiment of the compounds of Formula I, each $R^5$ is independently H or methyl.

In yet another embodiment of the compounds of Formula I, each $R^4$ is methyl.

In yet another embodiment of the compounds of Formula I, each $R^4$ and each $R^5$ is H.

In yet another embodiment of the compounds of Formula I, each $R^4$ and each $R^5$ is independently selected from the group consisting of H, methyl, ethyl, n-propyl, isopropyl, n-butyl, sec-butyl, and t-butyl.

In yet another embodiment of the compounds of Formula I, $R^3$ and $R^4$ together with the carbon atoms to which they are shown attached form a 4- to 8-membered cycloalkyl or heterocycloalkyl ring.

In yet another embodiment of the compounds of Formula I, $R^6$ is selected from the group consisting of H, methyl, ethyl, propyl, butyl, phenyl, chlorophenyl, fluorophenyl, difluorophenyl, trifluoromethylphenyl, and bis(trifluoromethyl)phenyl.

In yet another embodiment of the compounds of Formula I, $R^7$ is selected from the group consisting of chloro, bromo, fluoro, —CF₃, —OH, methyl, ethyl, propyl, butyl, hydroxymethyl, hydroxyethyl, hydroxypropyl, hydroxybutyl, methoxy, propoxy, butoxy, —OCF₃, —CN, —NH(methyl), —N(methyl)₂, —NH(ethyl), —N(ethyl)₂, —C(O)O-methyl, —C(O)O-ethyl, —CH₂—N(methyl)₂, —CH₂—N(ethyl)₂, —CH₂—NH₂, —N(methyl)C(O)-methyl, —NHC(O)-methyl, —N(methyl)C(O)-phenyl, —NHC(O)-phenyl, —N(methyl)C(O)-pyridyl, —NHC(O)-pyridyl, and —N(methyl)C(O)—N(methyl)₂, —N(methyl)C(O)—NH₂, —NHC(O)—N(methyl)₂, and —NHC(O)—NH₂.

In yet another embodiment of the compounds of Formula I, $R^8$ and $R^9$ are independently selected from the group consisting of H, methyl, ethyl, propyl, butyl, cyclopropyl, cyclobutyl, cyclopentyl, cyclohexyl, benzyl,

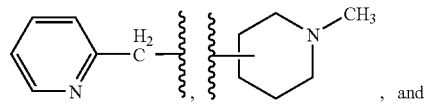

, and

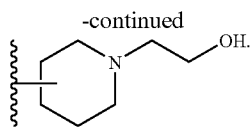

In yet another embodiment of the compounds of Formula I, each $R^{10}$ is independently selected from the group consisting of H, —OH, methyl, ethyl, propyl, butyl, HO—CH₂—, HO—CH₂CH₂—, —C(CH₃)₂CH₂—OH, methoxy, ethoxy, HO—CH₂—CH₂—O—, cyclopentyl, cyclohexyl, hydroxycyclopentyl, hydroxycyclohexyl, cyclopentyloxy, cyclohexyloxy, hydroxycyclopentyloxy, hydroxycyclohexyloxy, —C(O)—CH₃, —C(O)—CH₂CH₃, —CH₂—C(O)—OH, —CH₂CH₂—C(O)—OH, unsubstituted piperidinyl, piperidinyl substituted with one or more groups $R^7$, piperazinyl, piperazinyl substituted with one or more groups $R^7$, diazepanyl, diazepanyl substituted with one or more groups $R^7$, —CH₂—C(O)—NH₂, —CH₂—C(O)—NH(CH₃), —CH₂—C(O)—NH(CH₂CH₃), —CH₂—C(O)—NH(CH(CH₃)₂), —CH₂—C(O)—NH(phenyl), —CH₂—C(O)—N(CH₃)(phenyl), —CH₂—C(O)—N(CH₂CH₃)(phenyl), —CH₂—C(O)—N(phenyl)₂, —CH₂—C(O)—N(CH₃)₂, —C(O)—NH(CH₃), —C(O)—NH(CH₂CH₃), —C(O)—NH(CH(CH₃)₂), —C(O)—NH(phenyl), —C(O)—N(CH₃)(phenyl), —C(O)—N(CH₂CH₃)(phenyl), —C(O)—N(phenyl)₂, and —C(O)—N(CH₃)₂.

In yet another embodiment of the compounds of Formula I. two $R^{10}$ together with the ring carbon atoms to which they are shown attached form a 4- to 7-membered cycloalkyl or heterocycloalkyl ring.

In yet another embodiment of the compounds of Formula I. two $R^{10}$ together with the ring carbon atoms to which they are shown attached form a spiro-fused lactam ring.

In yet another embodiment of the compounds of Formula I. two $R^{10}$ together with the ring carbon atoms to which they are shown attached form a spiro-fused 4-membered lactam ring.

In yet another embodiment of the compounds of Formula I, $R^{11}$ is selected from the group consisting of H, methyl, ethyl, propyl, butyl, HO—CH₂—, HO—CH₂CH₂—, —C(CH₃)₂CH₂—OH, cyclopentyl, cyclohexyl, hydroxycyclopentyl, hydroxycyclohexyl, cyclopentyloxy, cyclohexyloxy, hydroxycyclopentyloxy, hydroxycyclohexyloxy, benzyl,

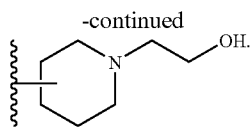

—C(O)O-methyl, —C(O)O-ethyl, —C(O)—O-t-butyl, —C(O)-methyl, —C(O)-ethyl, —C(O)—CH₂CH₂—OH, —C(O)-cyclopropyl, —C(O)-cyclobutyl, —C(O)-cyclopentyl, —C(O)-cyclohexyl, —C(O)—NH₂, —C(O)—NH(CH₃), —C(O)—NH(CH₂CH₃), —C(O)—N(CH₃)₂, —C(O)—N(CH₂CH₃)₂, —C(O)—NH(phenyl), —C(O)—N(phenyl)₂, —C(O)—N(CH₃)(phenyl), —C(O)—CH₂—NH₂, —C(O)—CH₂—NH(CH₃), —C(O)—CH₂—NH(CH₂CH₃), —C(O)—CH₂—N(CH₃)₂, —C(O)—CH₂—N(CH₂CH₃)₂, —C(O)—CH₂—NH(phenyl), —C(O)—CH₂—N(phenyl)₂, —C(O)—CH₂—N(CH₃)(phenyl), —S(O₂)-methyl, —S(O₂)-ethyl, —CH₂—C(O)—OH, —CH₂CH₂—C(O)—OH, —CH₂—O—CH₂—OH, —CH₂—O—CH₂CH₂—OH, phenyl, chlorophenyl, fluorophenyl, difluorophenyl, trifluoromethylphenyl, bis(trifluoromethyl)phenyl, pyridyl, trifluoromethylpyridyl, —CH₂—C(O)O—

CH$_3$, —CH$_2$CH$_2$—C(O)O—CH$_3$, —CH$_2$—C(O)O—CH$_2$CH$_3$, and —CH$_2$CH$_2$—C(O)O—CH$_2$CH$_3$.

In yet another embodiment of the compounds of Formula I, each R$^{12}$ is independently selected from the group consisting of H, methyl, ethyl, propyl, and butyl.

In yet another embodiment of the compounds of Formula I, R$^{13}$ is selected from the group consisting of H, piperazinyl, piperidinyl, tetrahydrothiophenyl, benzyl,

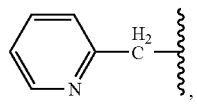

cyclopropyl, cyclopentyl, cyclohexyl, —CH$_2$-cyclohexyl, —CH$_2$CH$_2$-cyclohexyl, —CH$_2$-cyclopenty, —CH$_2$CH$_2$-cyclopentyl, and —CH$_2$-piperidinyl.

In yet another embodiment of the compounds of Formula I, R$^{14}$ is selected from the group consisting of chloro, fluoro, bromo, —CF$_3$, —OH, methoxy, ethoxy, —OCF$_3$, —CN, —NH(methyl), —N(methyl)$_2$, —NH(ethyl), —N(ethyl)$_2$, —C(O)-methyl, —C(O)-ethyl, —C(O)-phenyl, —C(O)—N(methyl)$_2$, —C(O)O-methyl, —C(O)O-ethyl, —CH$_2$—N(methyl)$_2$, —CH$_2$CH$_2$—N(methyl)$_2$, —CH$_2$—C(O)O-methyl, —N(methyl)C(O)-methyl, —NHC(O)-methyl, —N(methyl)C(O)-phenyl, —NHC(O)-phenyl, —N(methyl)C(O)-pyridyl, —NHC(O)-pyridyl, and —N(methyl)C(O)—N(methyl)$_2$, —N(methyl)C(O)—NH$_2$, —NHC(O)—N(methyl)$_2$, —NHC(O)—NH$_2$, piperidinyl, pyrrolidinyl, phenyl, and piperidinyl;

In yet another embodiment of the compounds of Formula I, R15 is selected from the group consisting of chloro, fluoro, bromo, —CF$_3$, —OH, methoxy, ethoxy, —OCF$_3$, —CN, methyl, ethyl, propyl, and butyl.

In yet another embodiment of the compounds of Formula I, X is selected from the group consisting of —O—, —NH—, —N(methyl)-, —N(ethyl)-, —O—CH$_2$—, —O—CH$_2$CH$_2$—, —CH$_2$—O—, and —CH$_2$CH$_2$—O—.

In yet another embodiment of the compounds of Formula I, X is —O—.

In yet another embodiment of the compounds of Formula I, Y is selected from the group consisting of —NH(methyl), —NH(ethyl), —N(methyl)$_2$, —N(ethyl)$_2$,

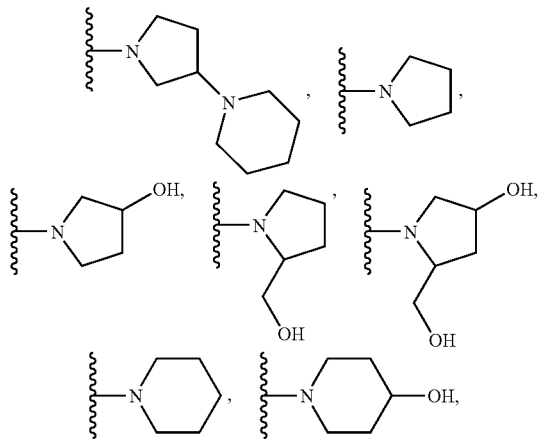

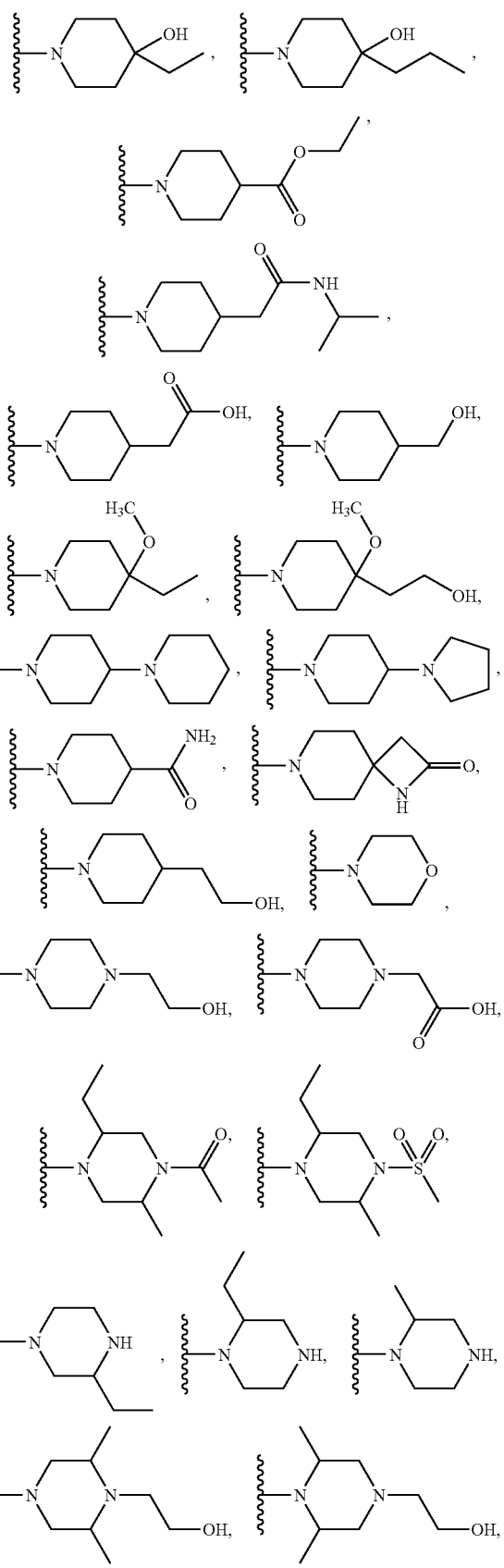

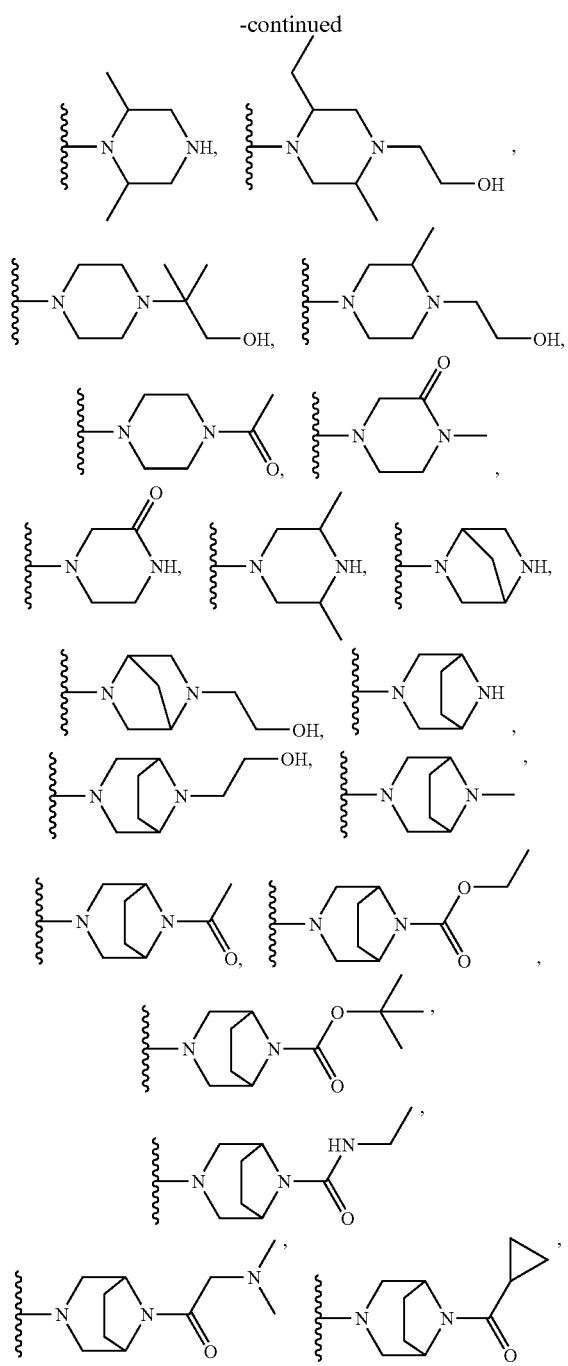
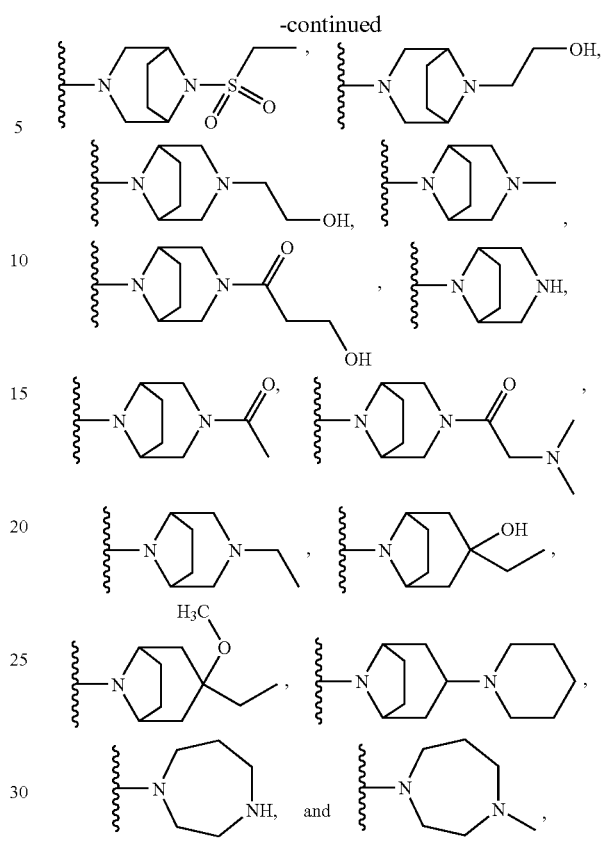
In still another embodiment, the compound of Formula I has a structure according to Formula (II), wherein L, Q, Y, and $R^3$ are as shown in Table 1:
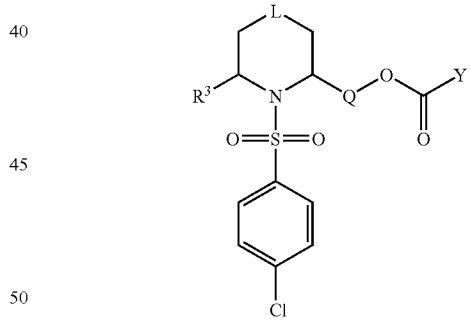
TABLE 1
| Structure | L | Q | Y | $R^3$ |
|---|---|---|---|---|
| i | —O— | —CH$_2$— | (piperazine-N-CH$_2$CH$_2$OH) | (3,5-difluorophenyl) |

TABLE 1-continued

| Structure | L | Q | Y | R³ |
|-----------|---|---|---|-----|
| ii | —O— | —CH₂— | 4-(piperidin-1-yl)piperidin-1-yl | 3,5-difluorophenyl |
| iii | —O— | —CH₂— | 4-hydroxy-4-propylpiperidin-1-yl | 3,5-difluorophenyl |
| iv | —O— | 1,1-cyclopropanediyl | 4-hydroxypiperidin-1-yl | —CH₂CH₂CH₃ |
| v | —O— | 1,1-cyclopropanediyl | 4-(piperidin-1-yl)piperidin-1-yl | —CH₂CH₂CH₃ |
| vi | —O— | 1,1-cyclopropanediyl | 4-(2-hydroxyethyl)piperazin-1-yl | —CH₂CH₂CH₃ |
| vii | —O— | 1,1-cyclopropanediyl | 3-hydroxy-1-methylpyrrolidinyl | —CH₂CH₂CH₃ |
| viii | —O— | 1,1-cyclopropanediyl | 2-(hydroxymethyl)pyrrolidin-1-yl | —CH₂CH₂CH₃ |
| ix | —O— | 1,1-cyclopropanediyl | morpholin-4-yl | —CH₂CH₂CH₃ |
| x | —O— | 1,1-cyclopropanediyl | 4-(1-hydroxy-2-methylpropan-2-yl)piperazin-1-yl | —CH₂CH₂CH₃ |
| xi | —O— | 1,1-cyclopropanediyl | 4-ethyl-4-methoxypiperidin-1-yl | —CH₂CH₂CH₃ |
| xii | —O— | 1,1-cyclopropanediyl | 4-(2-hydroxyethyl)-4-methoxypiperidin-1-yl | —CH₂CH₂CH₃ |

TABLE 1-continued
| Structure | L | Q | Y | R³ |
|---|---|---|---|---|
| xiii | —O— | 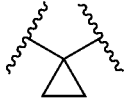 | 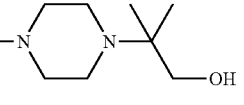 | 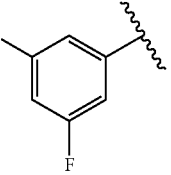 |
| xiv | —O— | 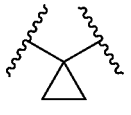 | 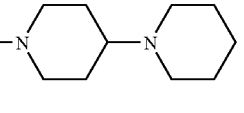 | 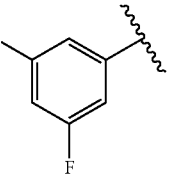 |
| xv | —O— | 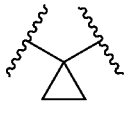 | 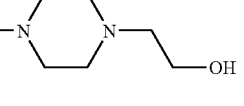 | 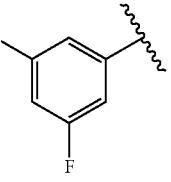 |
| xvi | —O— | 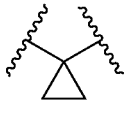 | 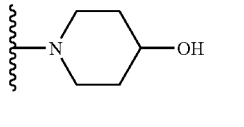 | 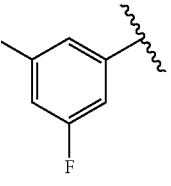 |
| xvii | —O— | 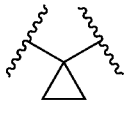 | 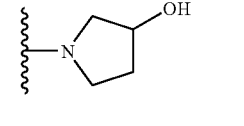 | 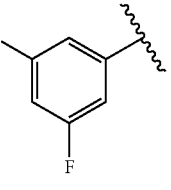 |
| xviii | —O— | 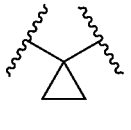 | 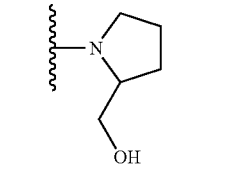 | 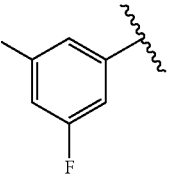 |
| xix | —O— | 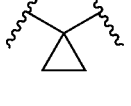 | 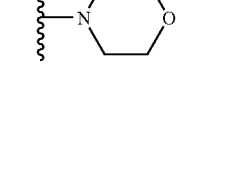 | 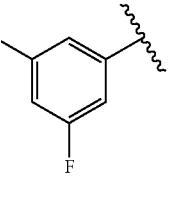 |
| xx | —O— | 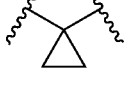 | 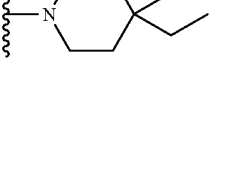 | 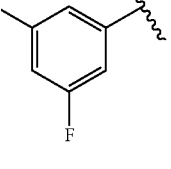 |

TABLE 1-continued
| Structure | L | Q | Y | R³ |
|---|---|---|---|---|
| xxi | —O— | 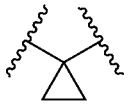 |  | 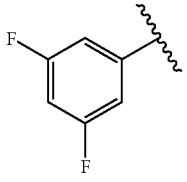 |
| xxii | —O— | 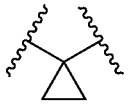 | 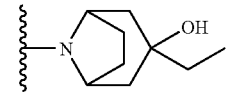 | 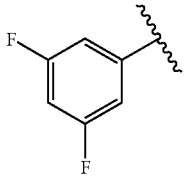 |
| xxiii | —O— | 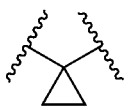 | 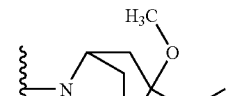 | 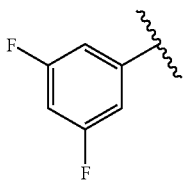 |
| xxiv | —O— | 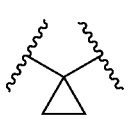 | 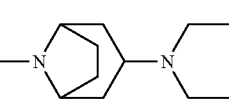 | 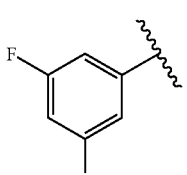 |
| xxv | —O— | 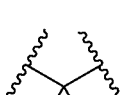 | 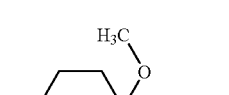 | 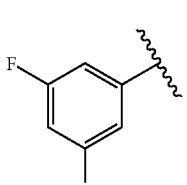 |
| xxvi | —O— | —CH₂— | 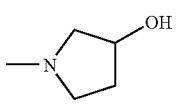 |  |
| xxvii | —O— | —CH₂— | 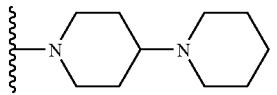 |  |
| xxviii | —O— | —CH₂— | 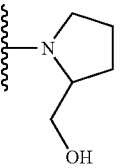 |  |
| xxix | —S— | 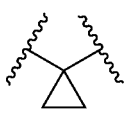 | 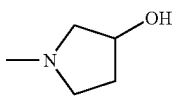 | —CH₂CH₃ |
| xxx | —S(O)— | 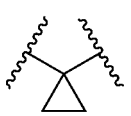 | 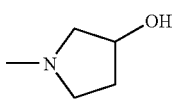 | —CH₂CH₃ |

TABLE 1-continued
| Structure | L | Q | Y | R³ |
|---|---|---|---|---|
| xxxi | —S(O)— | (cyclopropyl) | (pyrrolidinyl-CH₂OH) | —CH₂CH₃ |
| xxxii | —S— | (cyclopropyl) | (pyrrolidinyl-CH₂OH) | —CH₂CH₃ |
| xxxiii | —S— | (cyclopropyl) | (4-piperidinylpiperidinyl) | —CH₂CH₃ |
| xxiv | —N(CH₂CH₃)— | —CH₂— | (4-piperidinylpiperidinyl) | (3,5-difluorophenyl) |
In still another embodiment, the compound of Formula I is selected from the group consisting of:
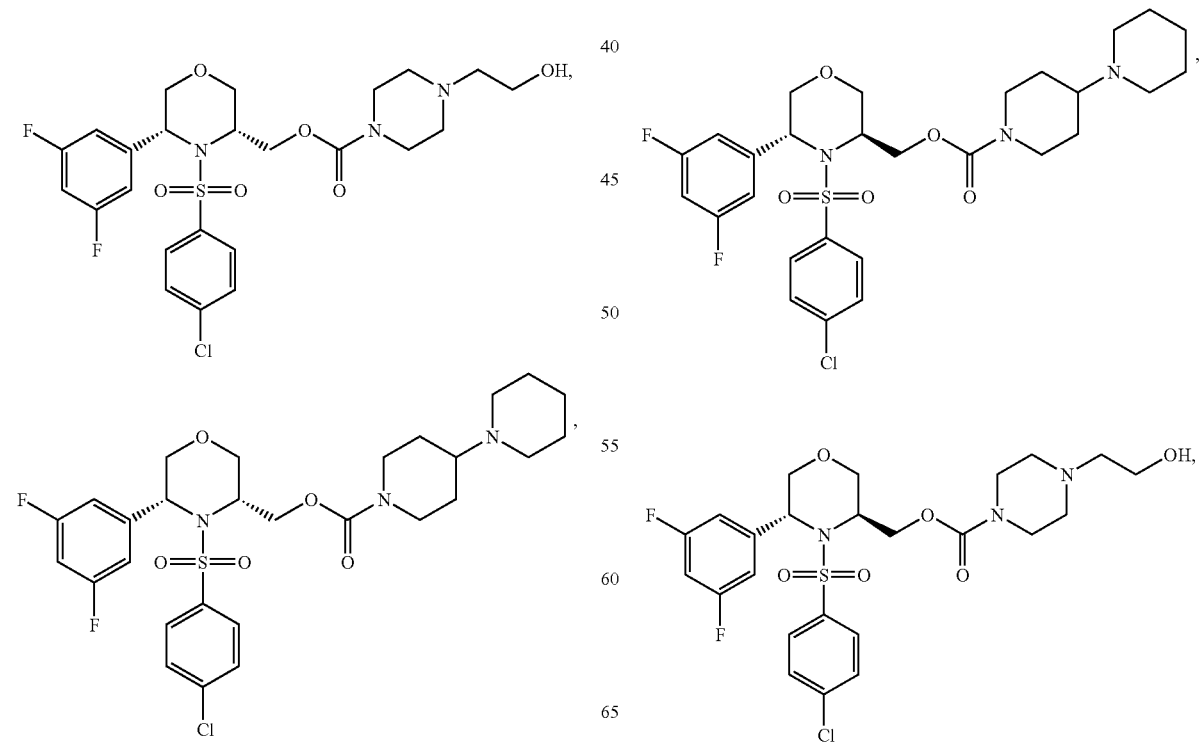

21
-continued
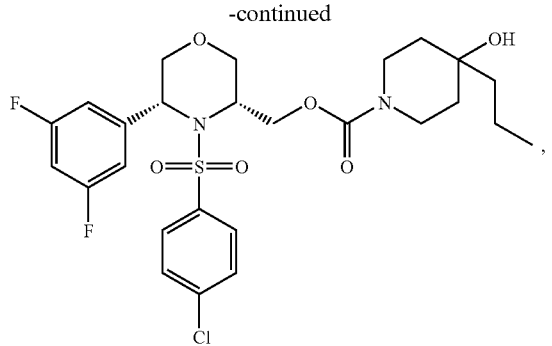
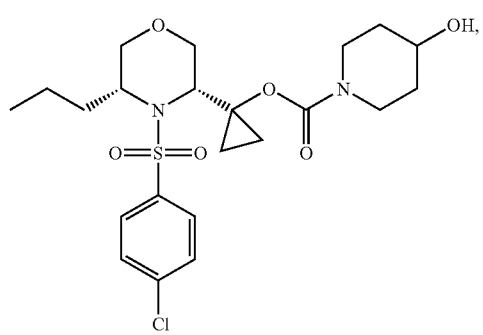
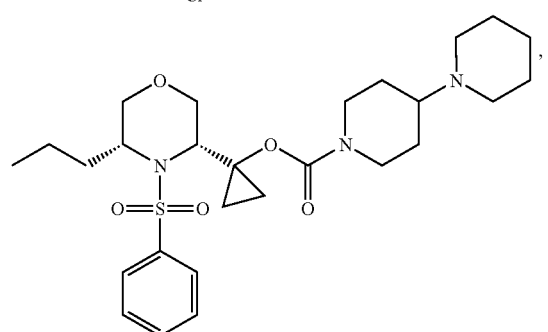
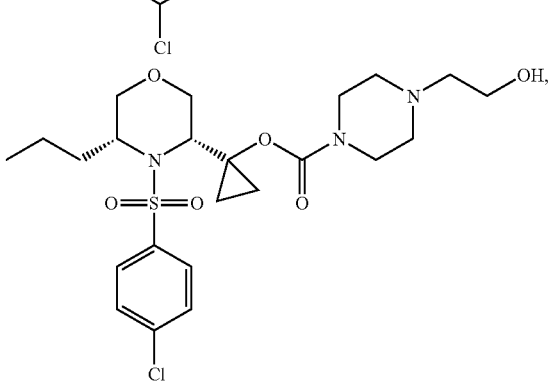
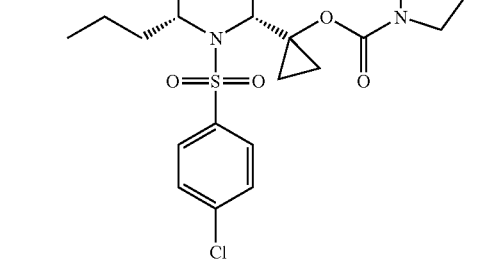
22
-continued
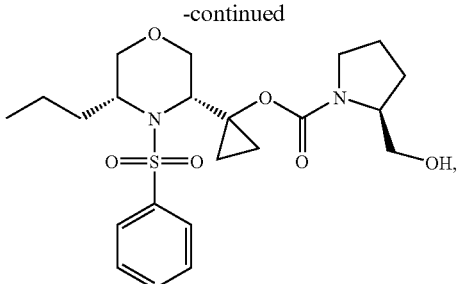
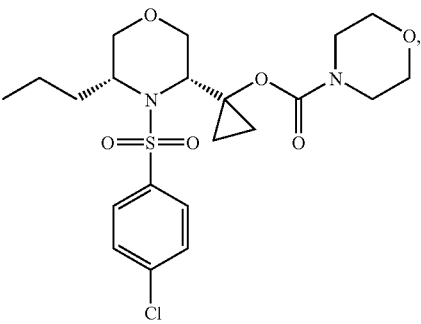
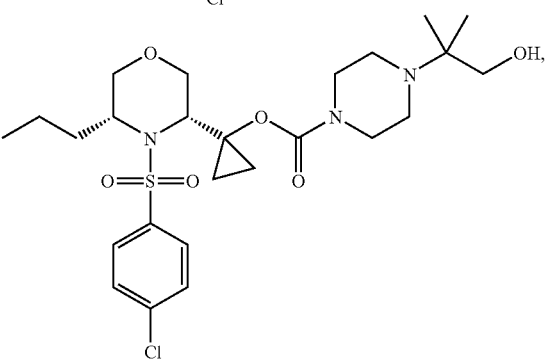
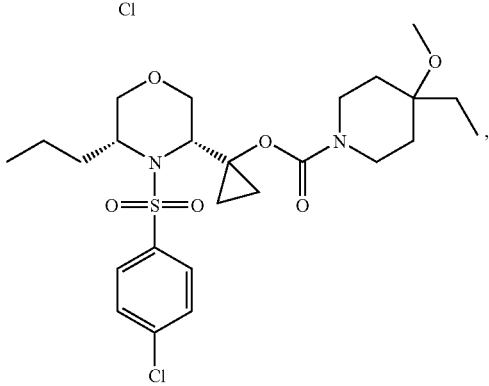
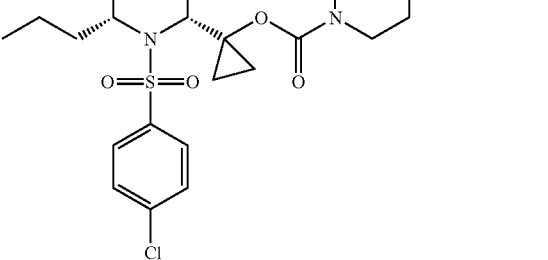

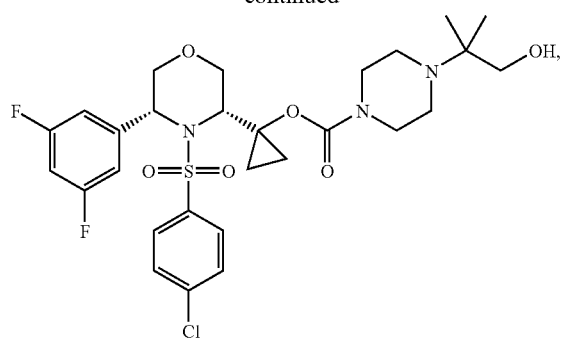
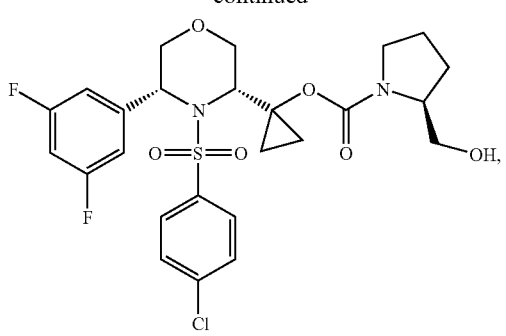
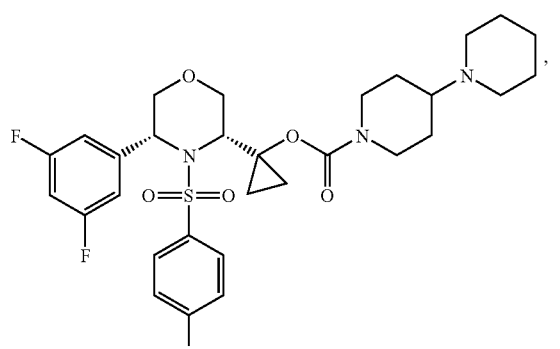
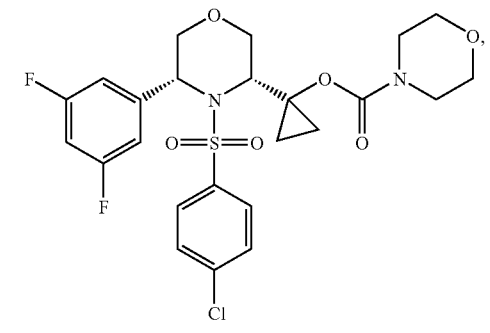
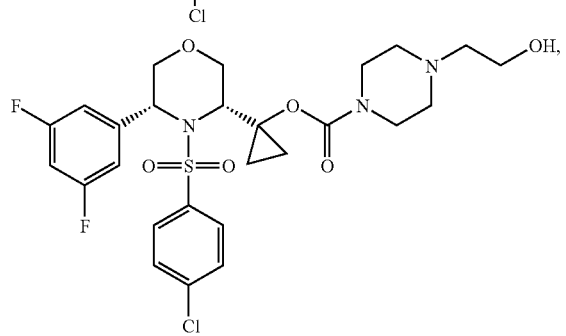
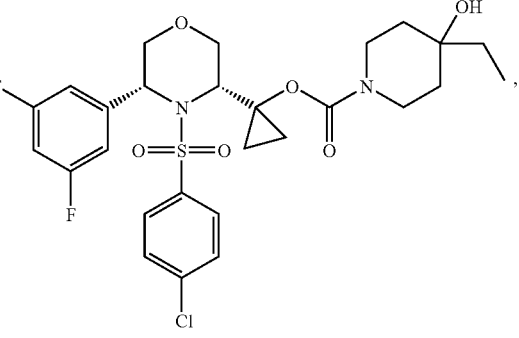
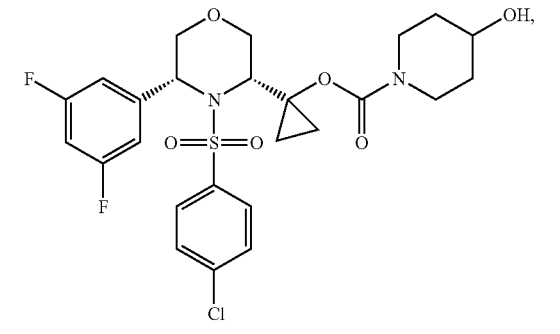
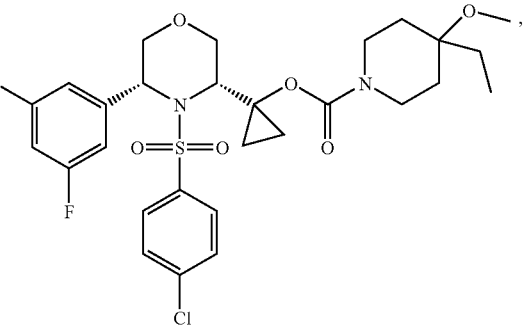
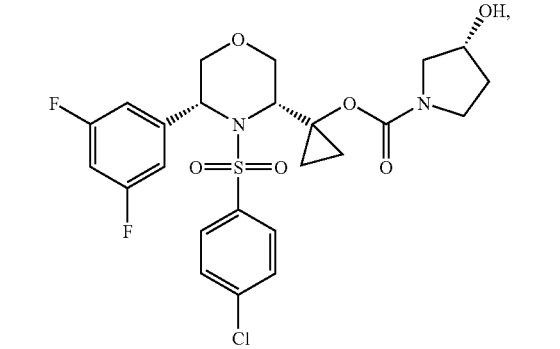
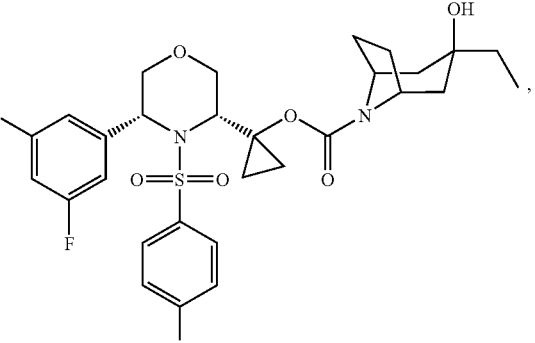

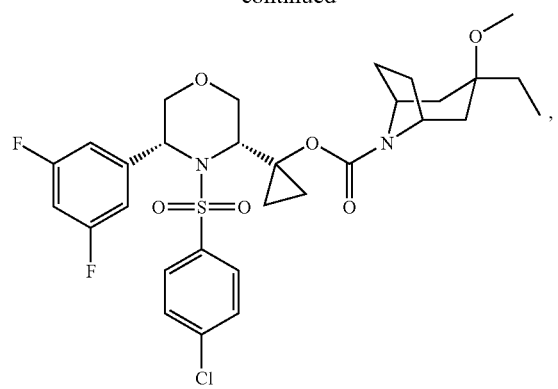
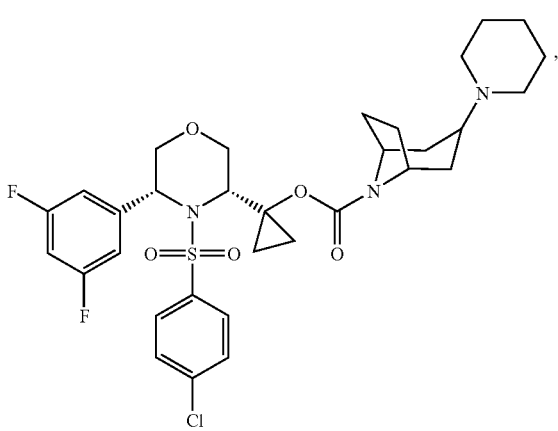
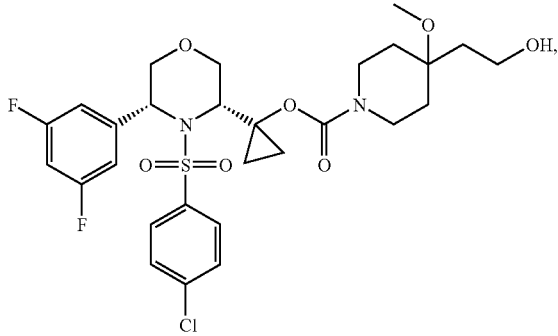
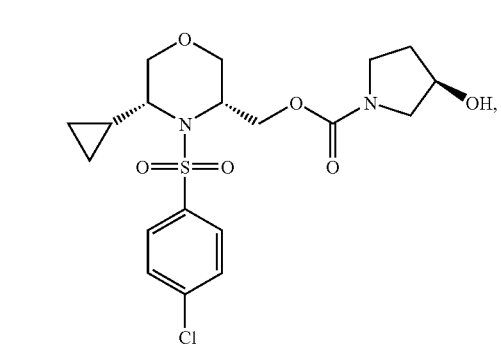
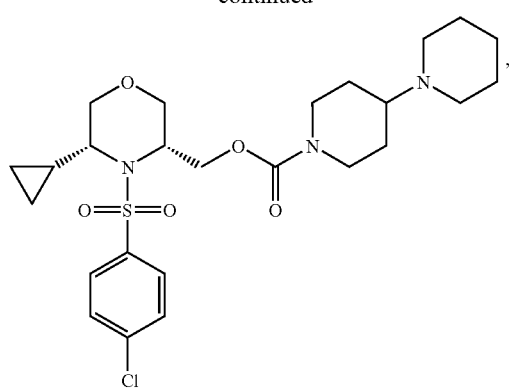
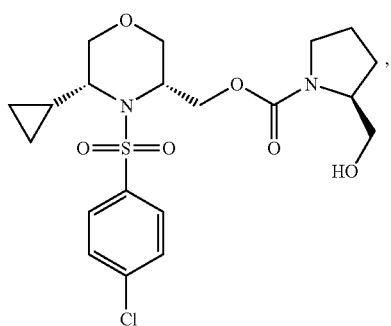
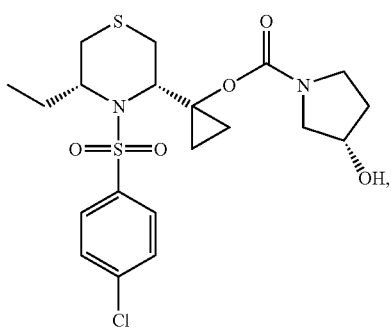
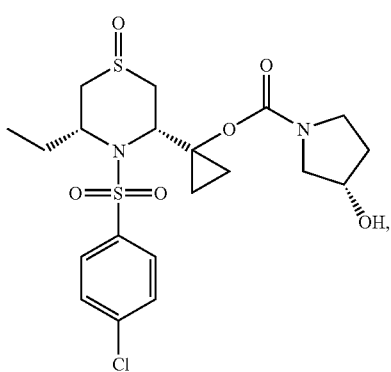

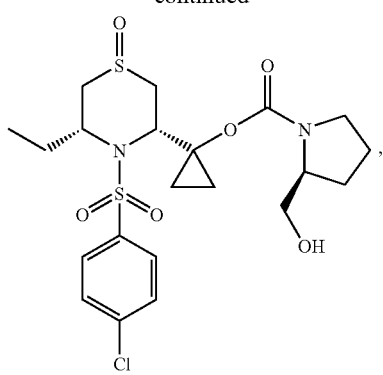
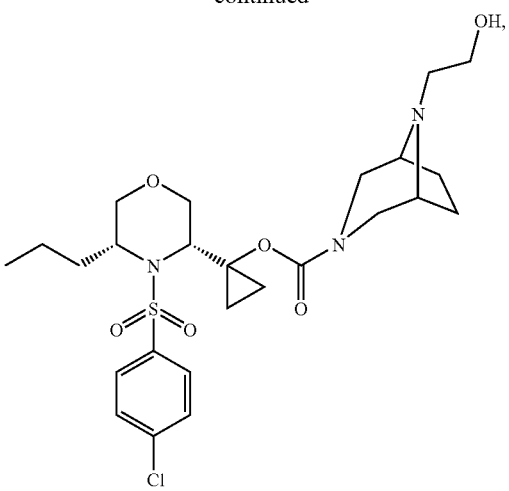
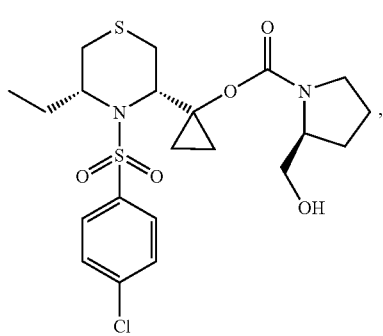
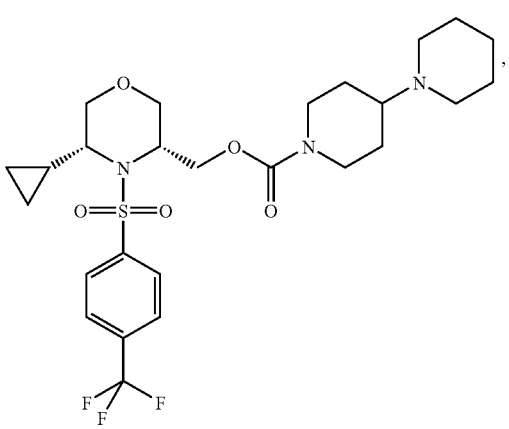
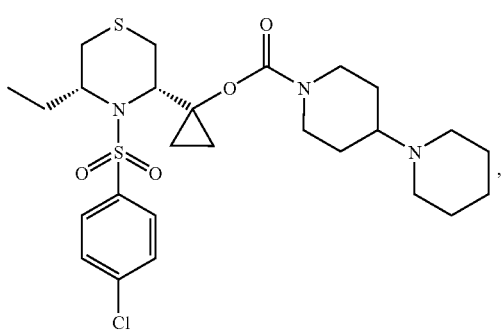
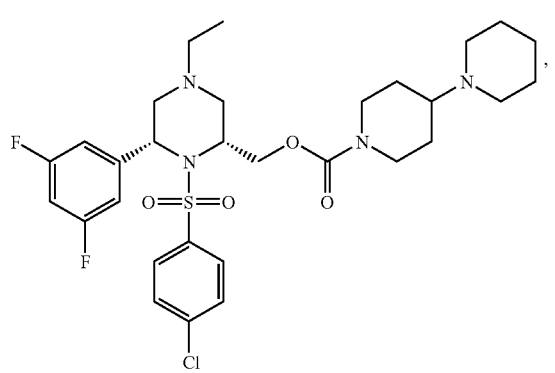
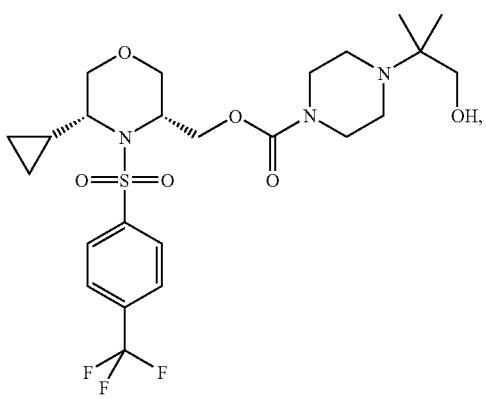

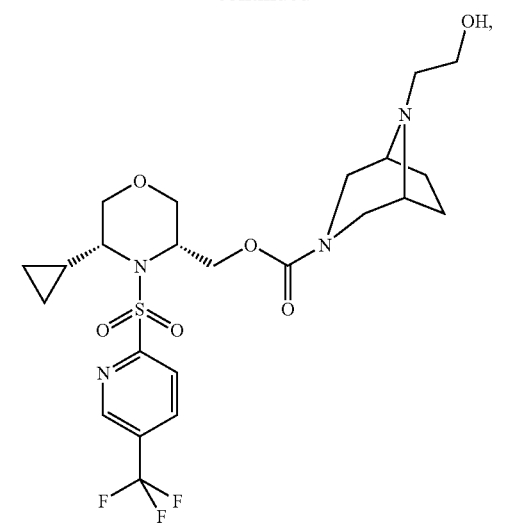
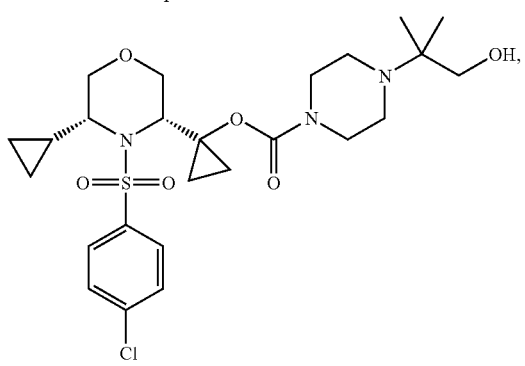
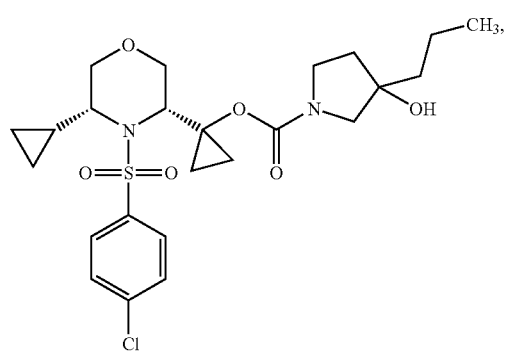
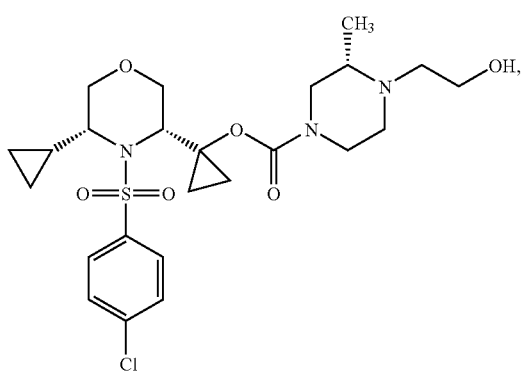
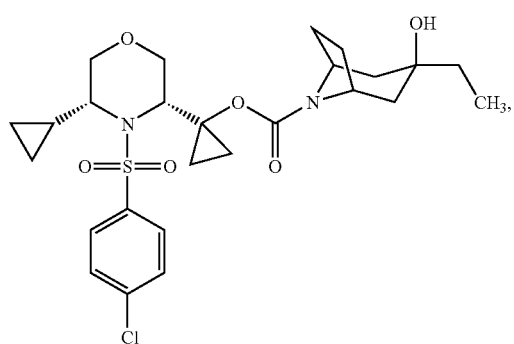
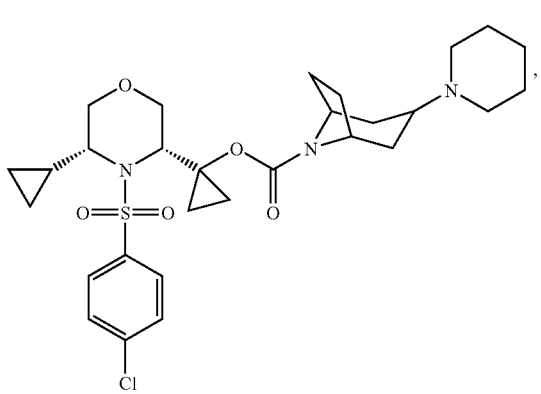
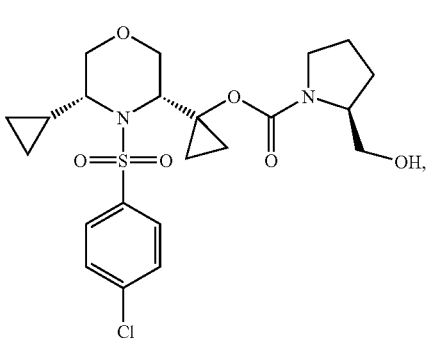
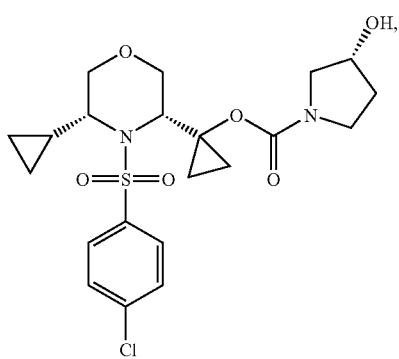

31
-continued
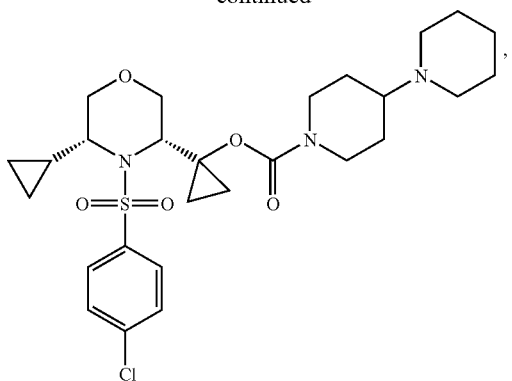
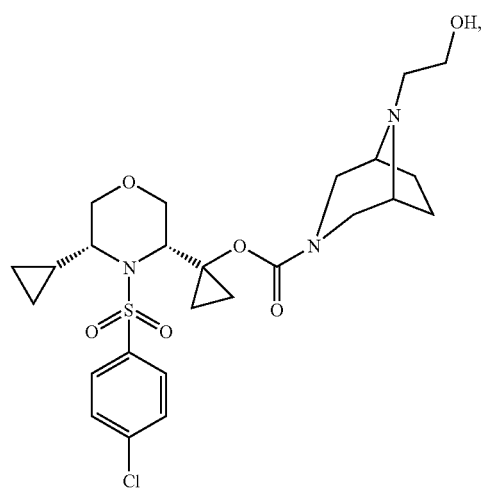
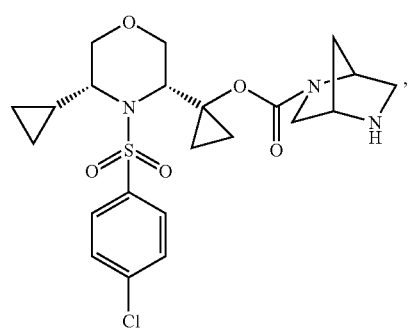
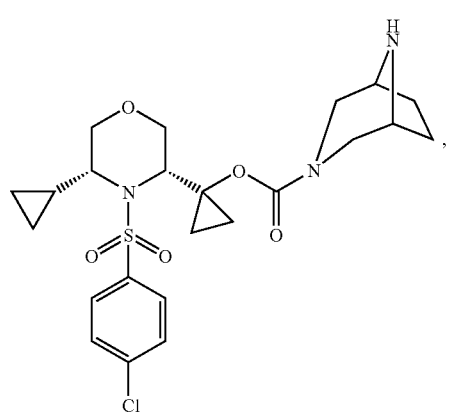
32
-continued
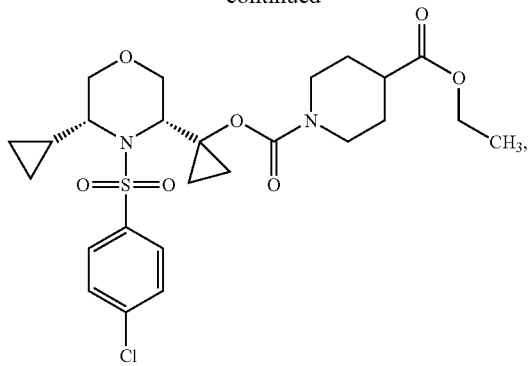
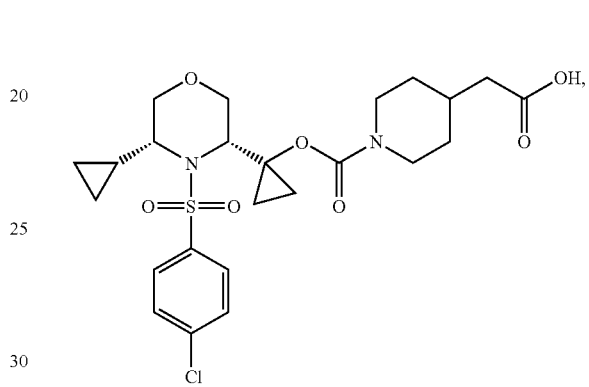
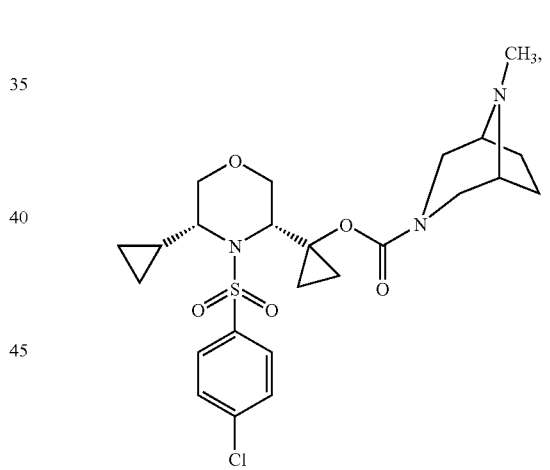
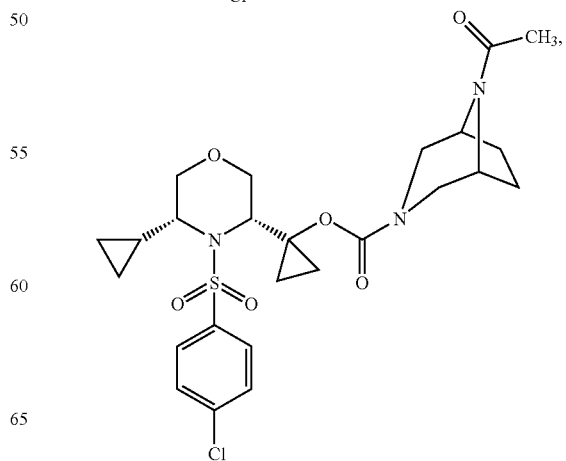

33
-continued
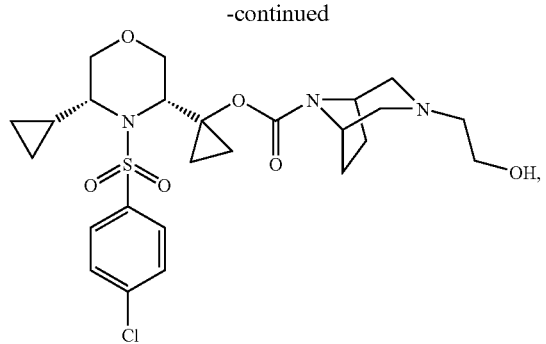
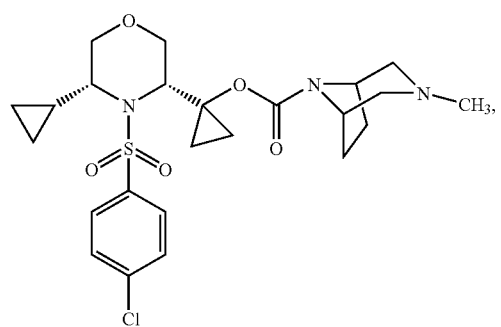
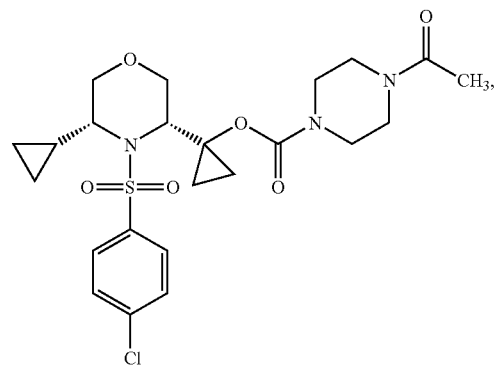
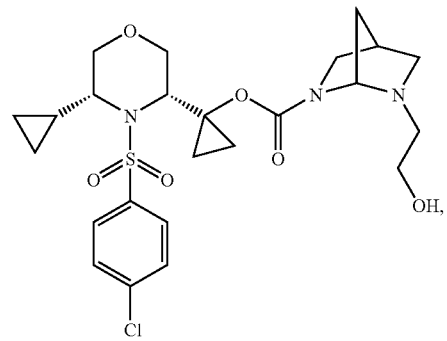
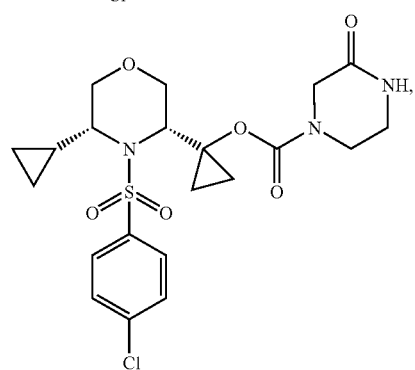
34
-continued
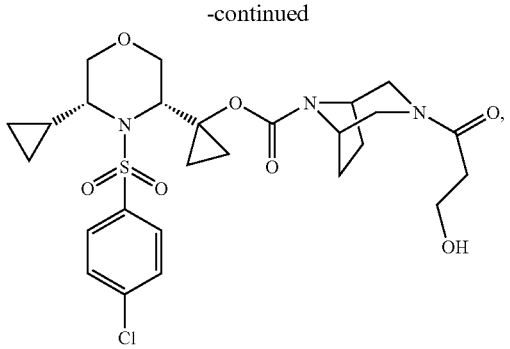
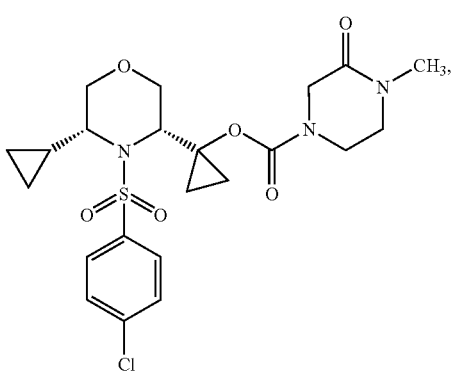
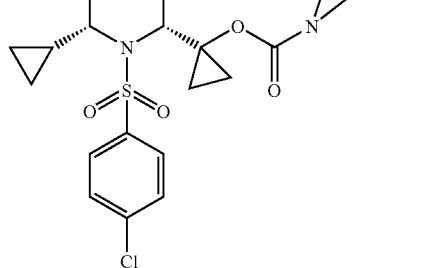

35
-continued
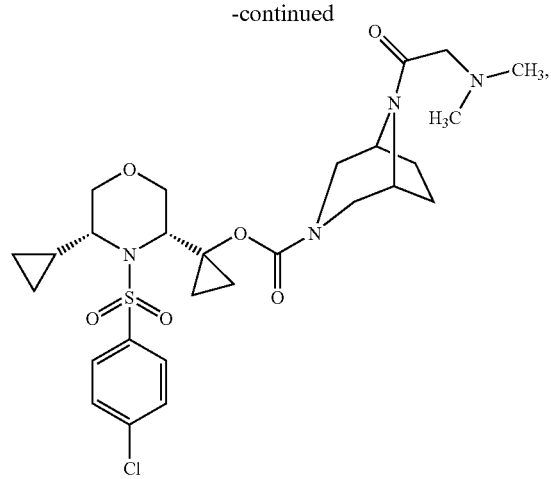
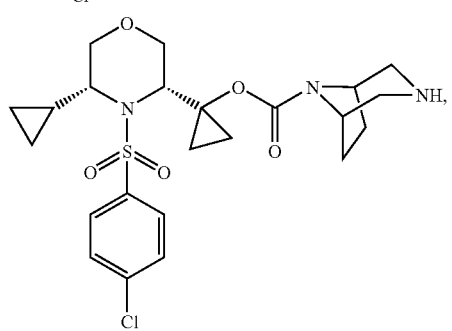
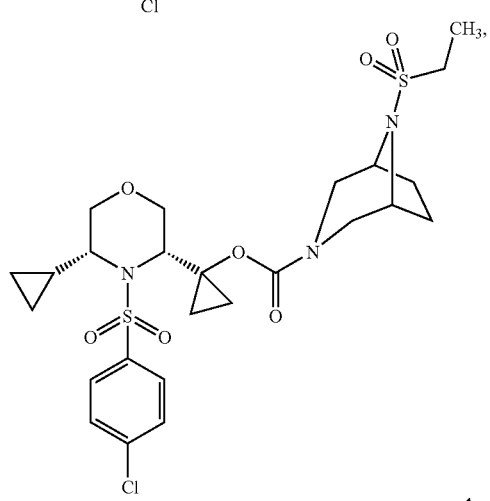
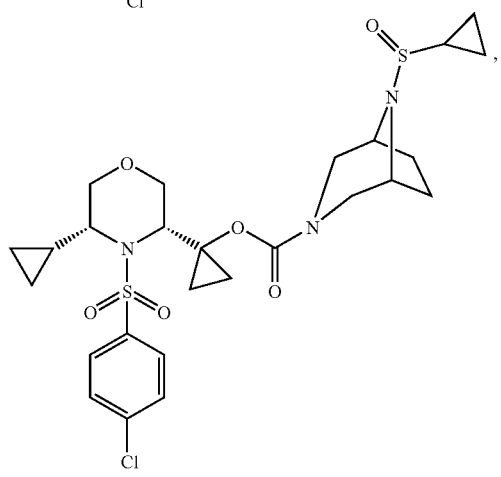
36
-continued
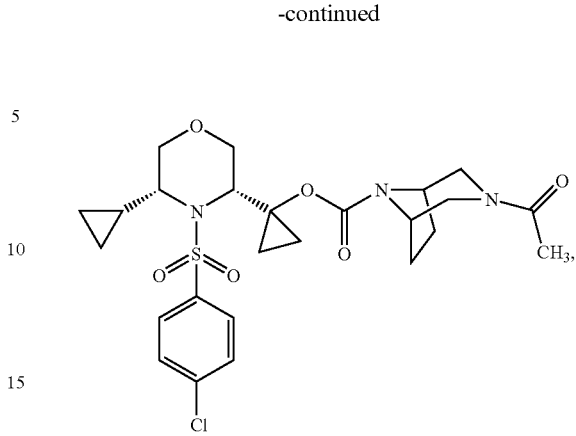
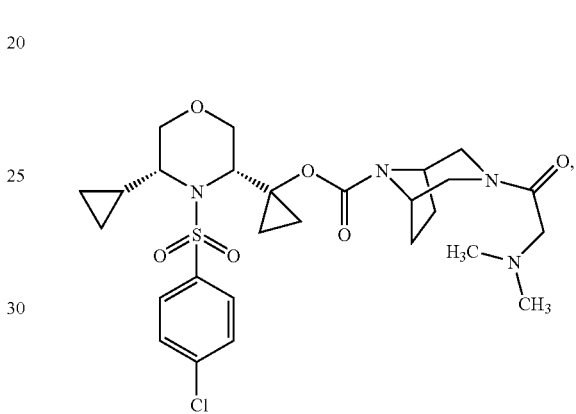
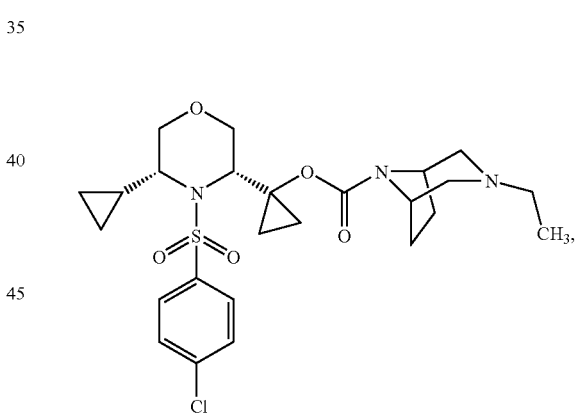
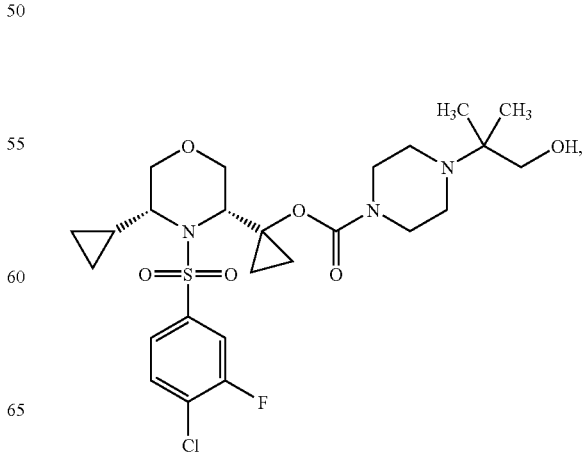

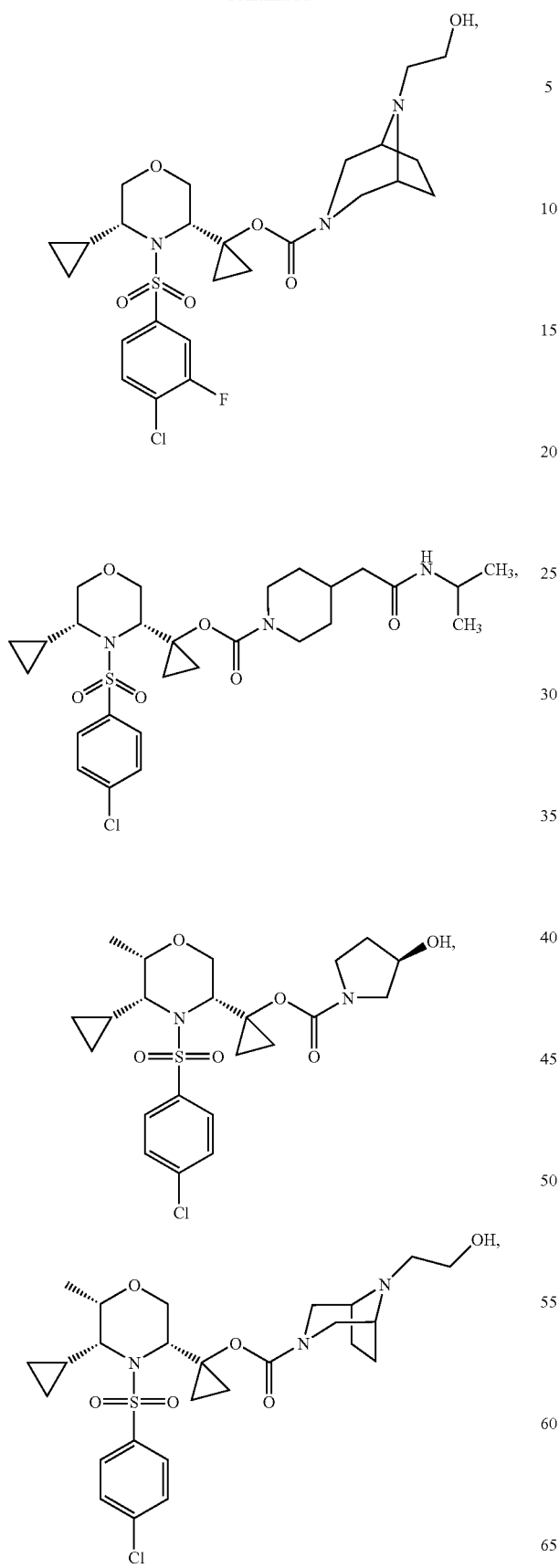
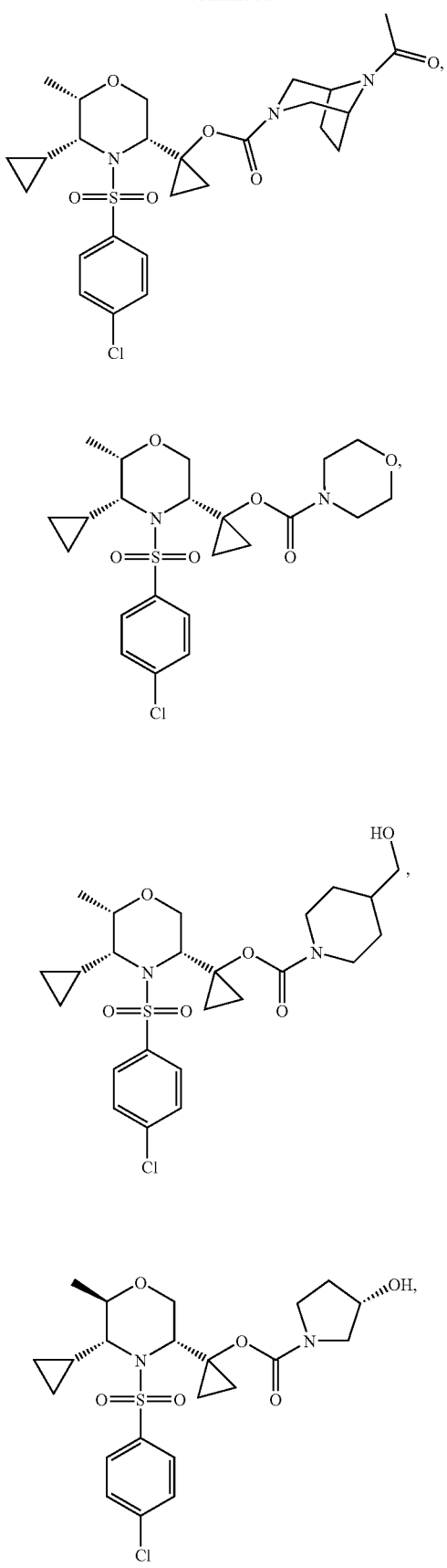

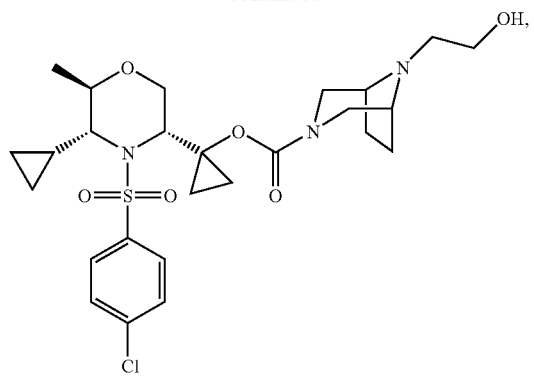
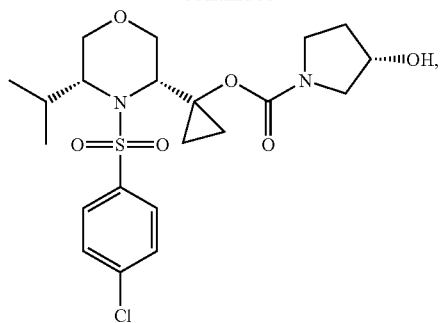
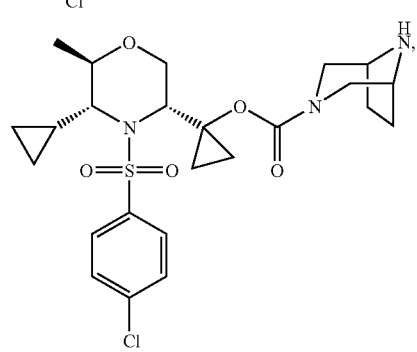
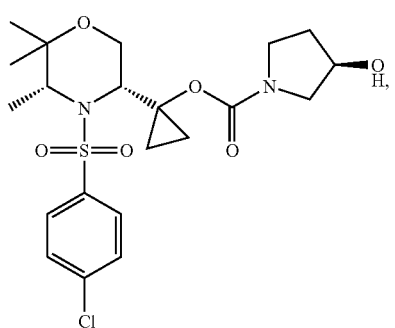
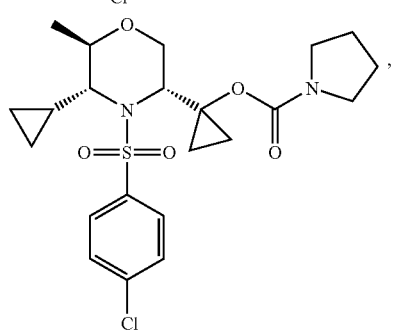
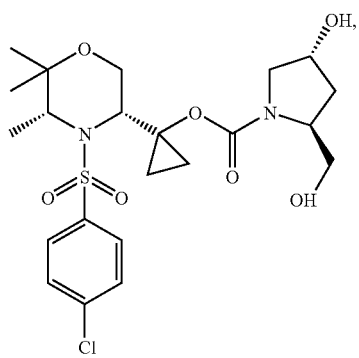
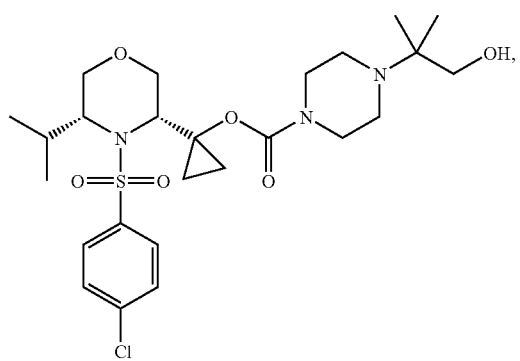
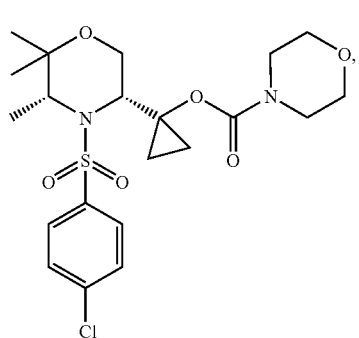
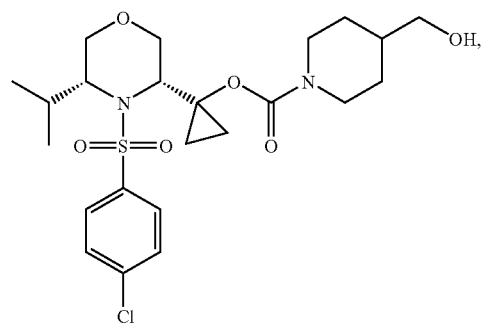
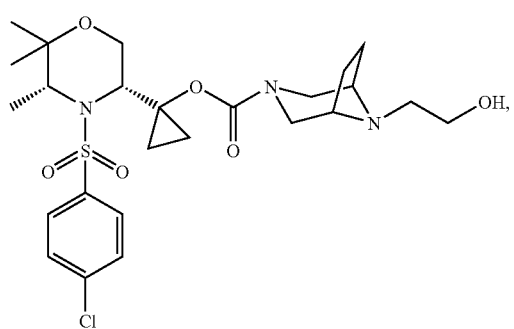

41
-continued
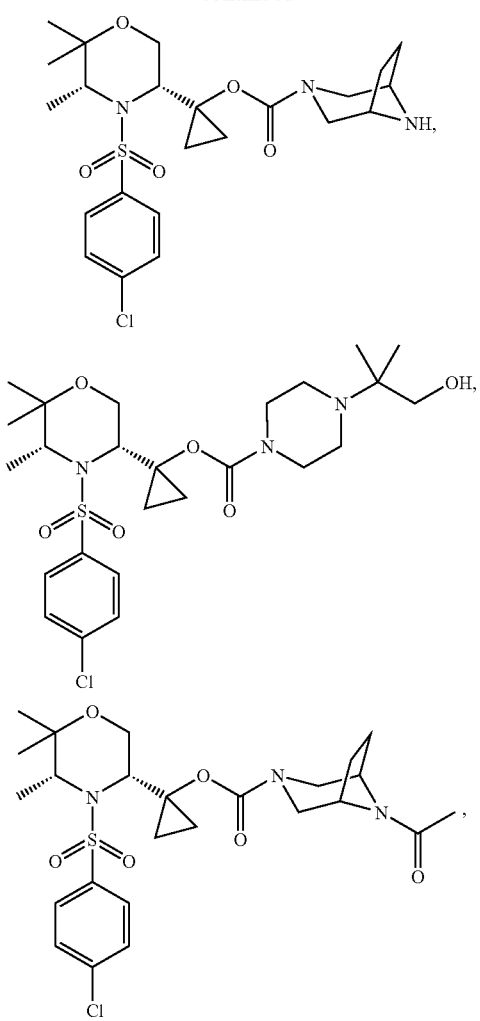
42
-continued
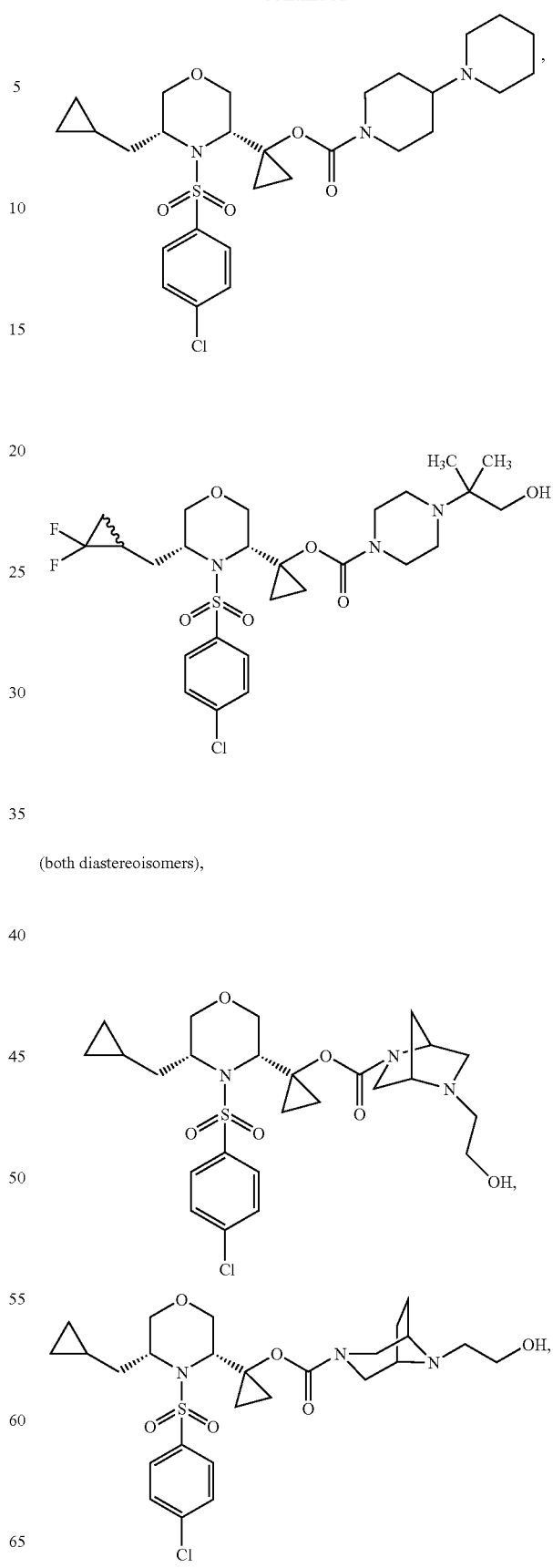
(both diastereoisomers),

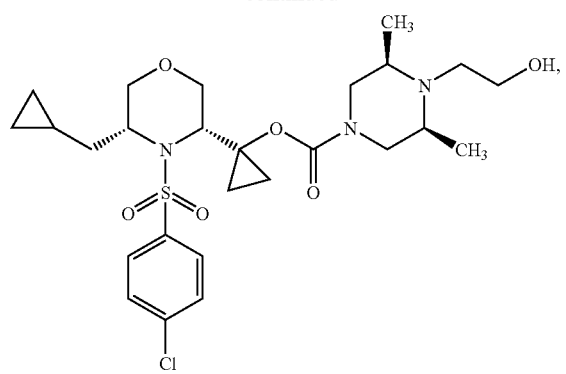
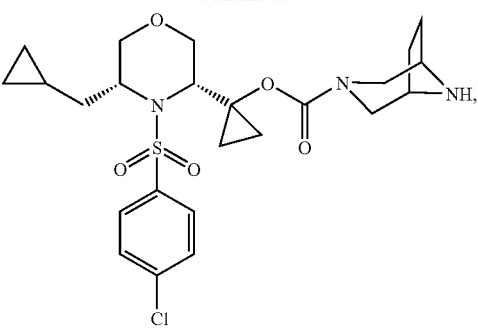
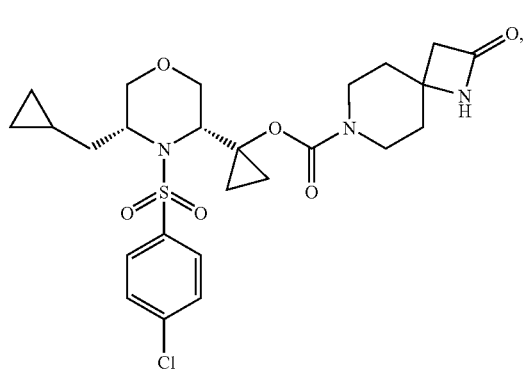
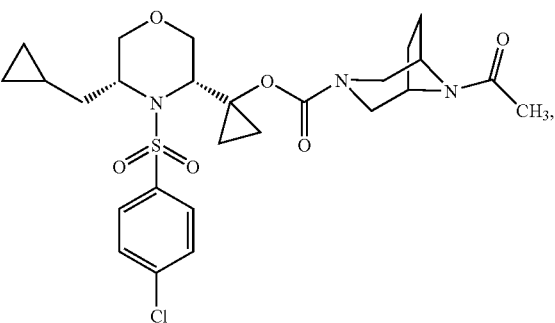
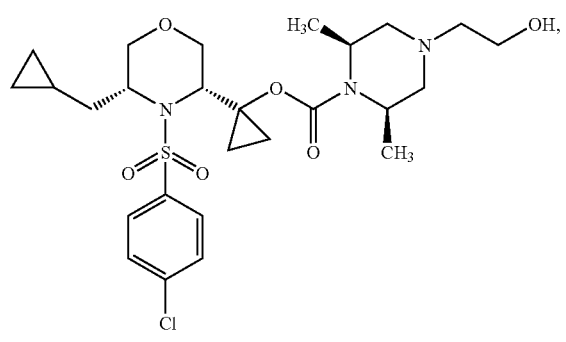
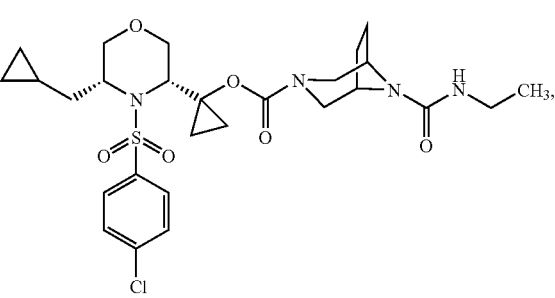
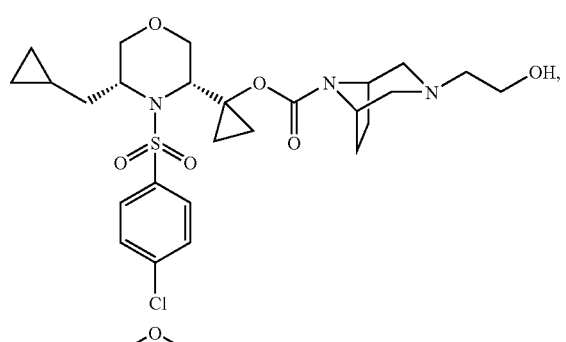
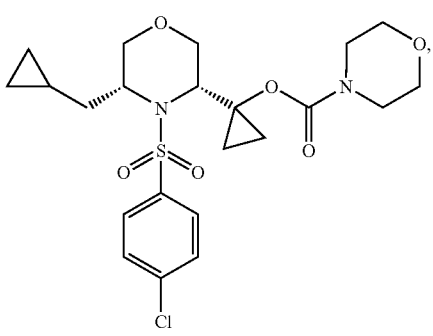
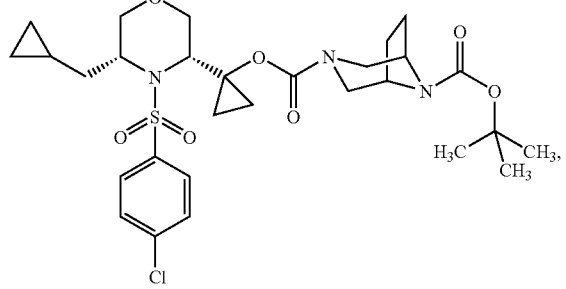
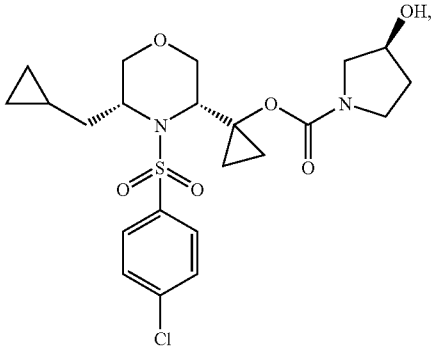

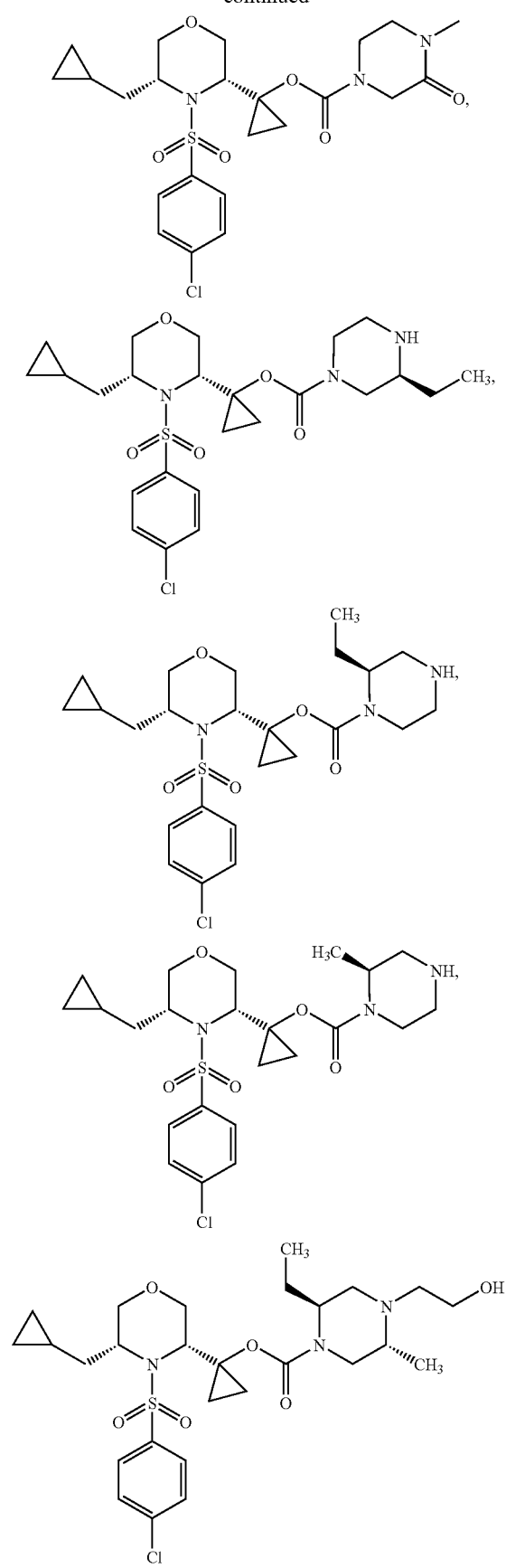
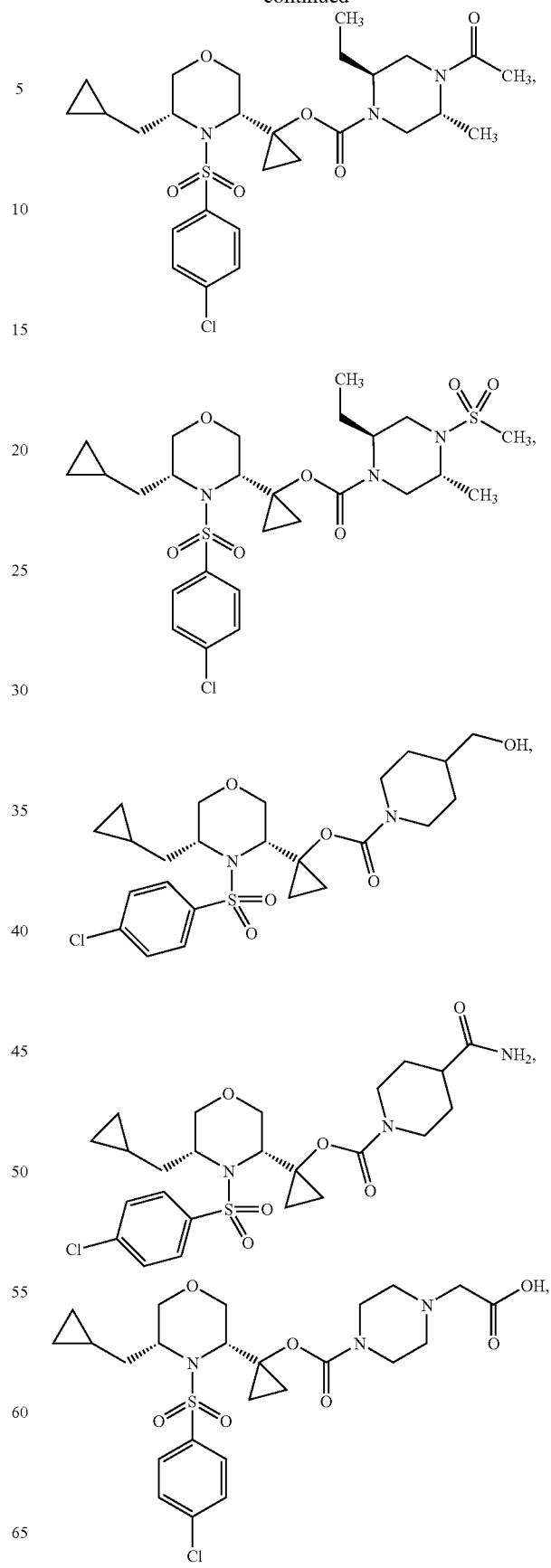

47
-continued
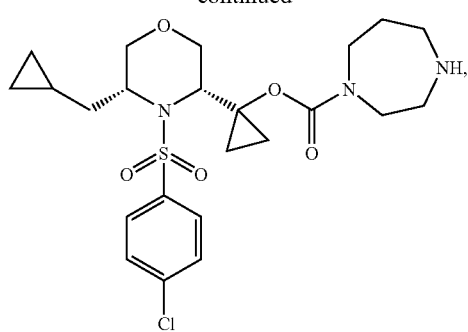
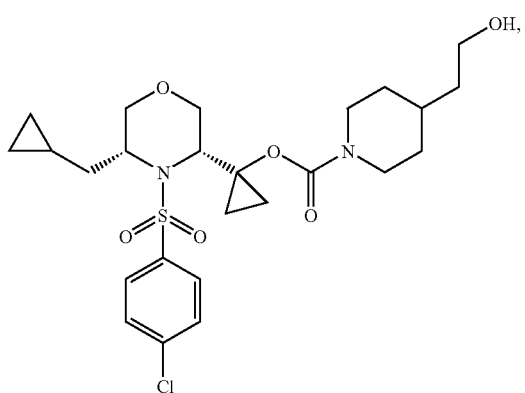
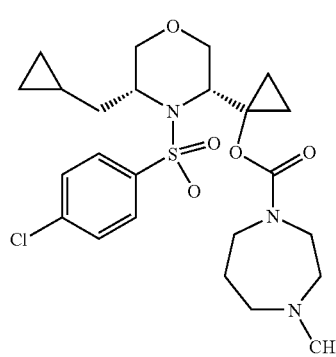
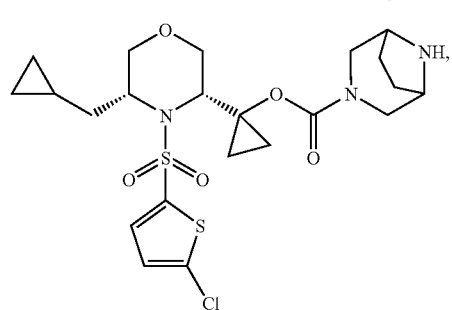
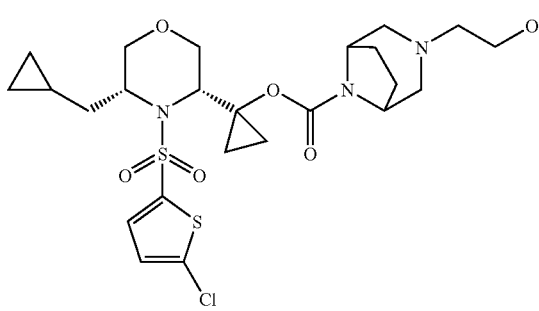
48
-continued
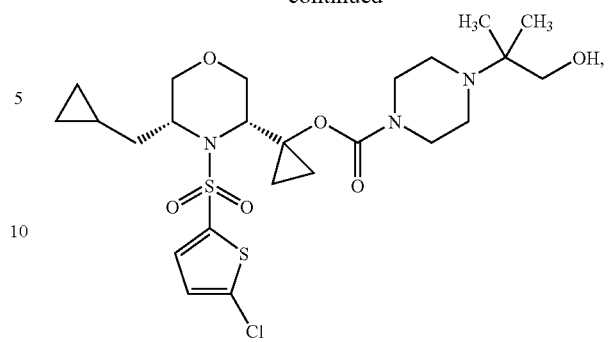
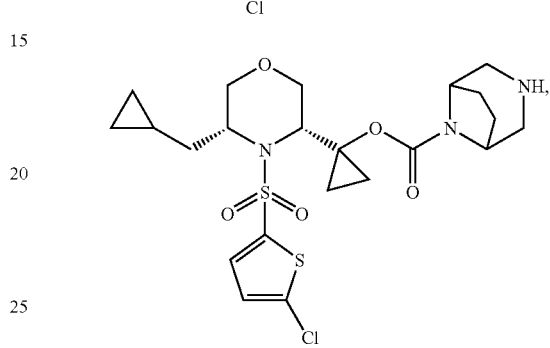
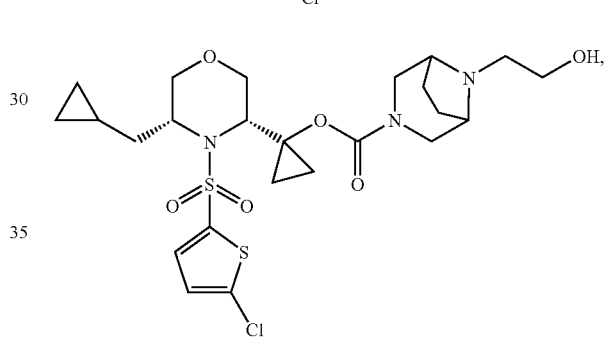
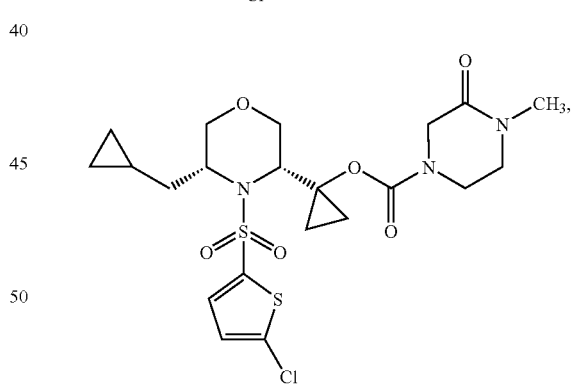
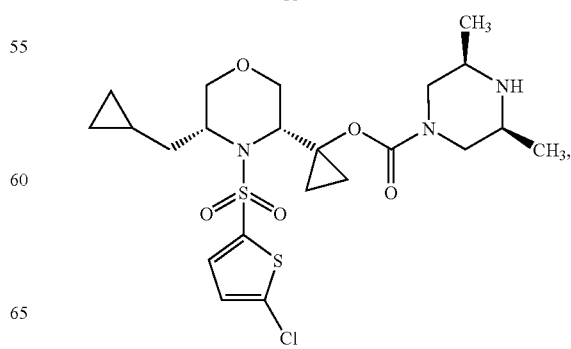

49
-continued
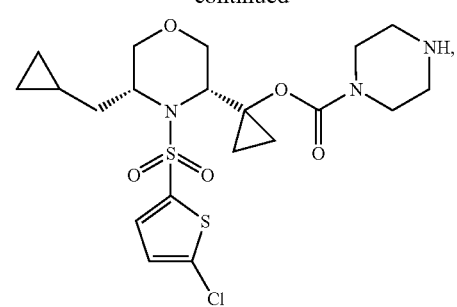
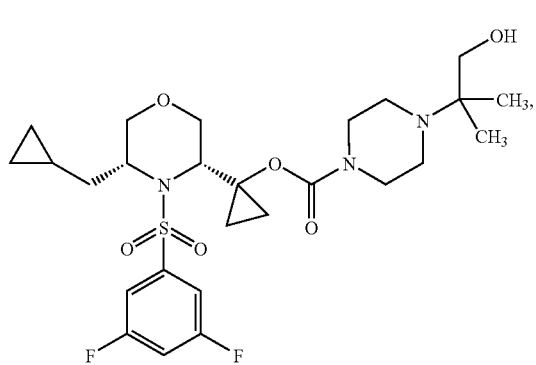
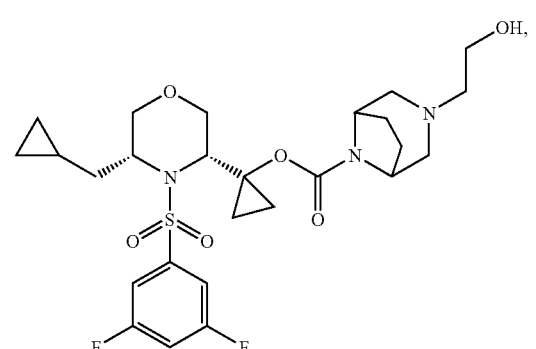
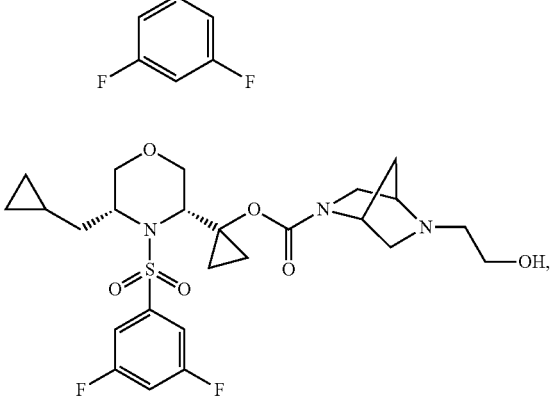
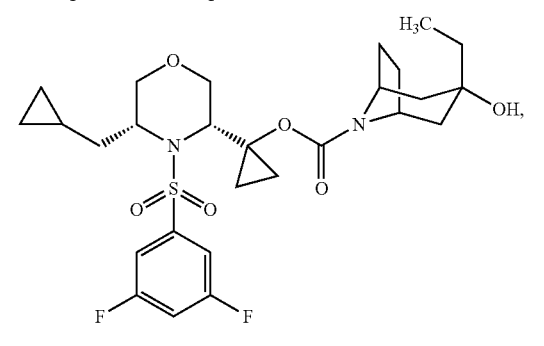
50
-continued
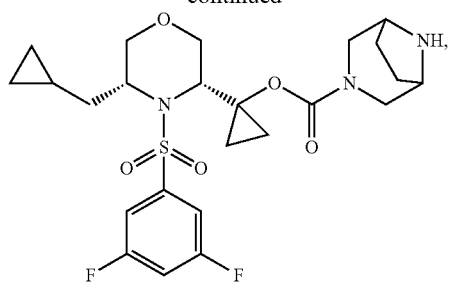
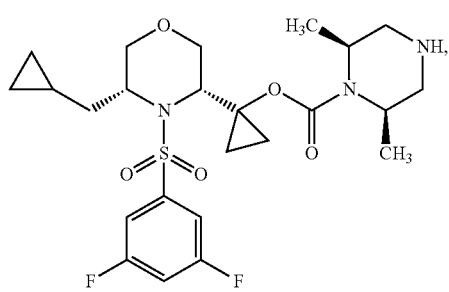
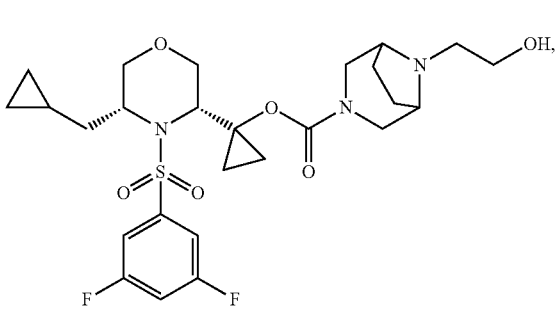
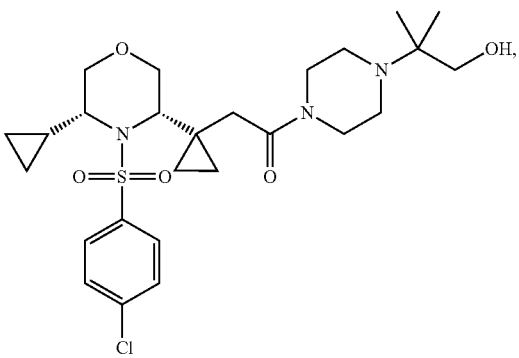
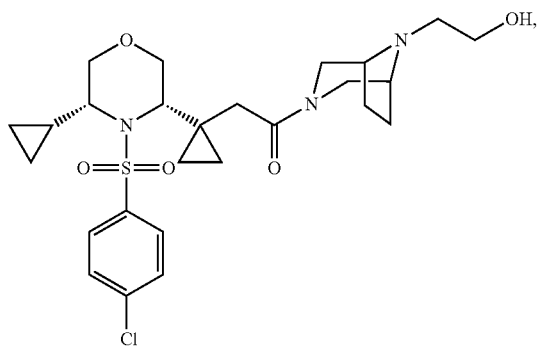

-continued

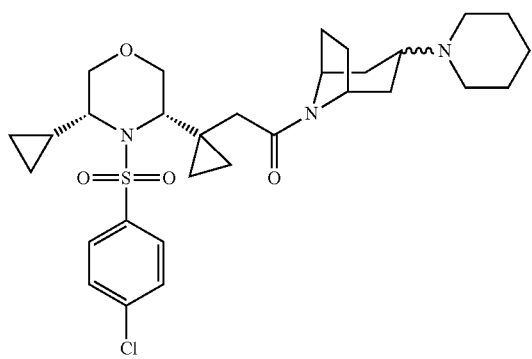

(both diastereoisomers),

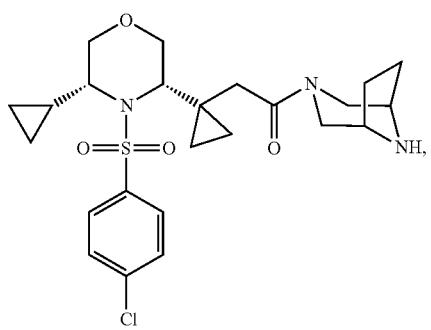

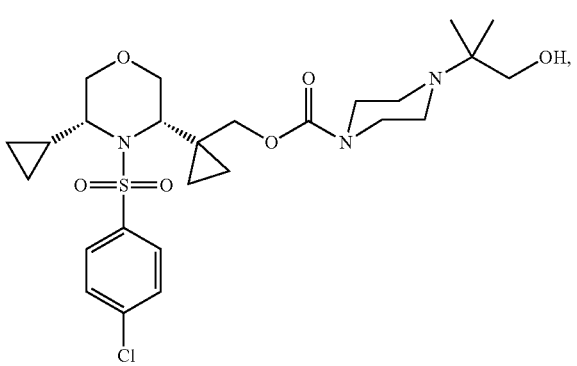

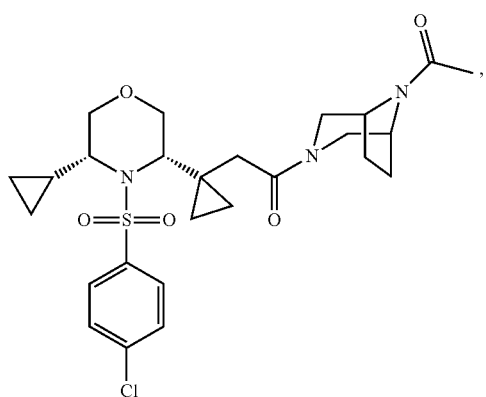

-continued

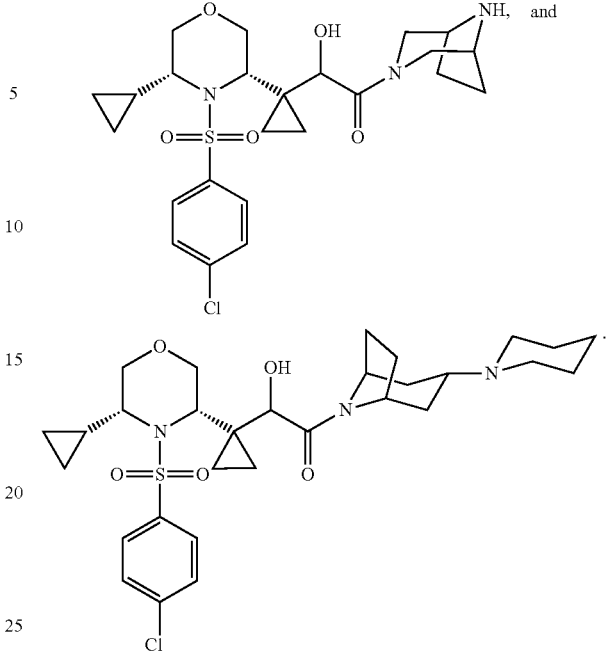

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl (unless expressly defined otherwise). Non-limiting examples of suitable alkyl groups include methyl, ethyl, n-propyl, isopropyl and t-butyl.

"Alkylene" means a divalent aliphatic hydrocarbon radical derived from an alkyl group, as defined above. Both "open" valences may be on the same carbon atom, or on different carbon atoms. Non-limiting examples of alkylene groups include —CH$_2$—, —CH$_2$—CH$_2$—, —CH(CH$_3$)—, etc.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain, which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Arylalkyl" (or "aralkyl") means an aryl-alkyl-group in which the aryl and alkyl are as previously described. Preferred arylalkyls comprise a lower alkyl group. Non-limiting examples of suitable arylalkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable saturated monocyclic cycloalkyls include cyclopropyl, cyclopentyl, cyclohexyl, cycloheptyl and the like, and non-limiting examples of non-aromatic, unsaturated monocyclic cycloalkyls include cyclopentenyl, cyclohexenyl, etc. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkylene" means a divalent cycloalkyl radical derived from a cycloalkyl group, as defined above. Both open valences may be on the same ring carbon atom, or may be on different ring carbon atoms. Non-limiting examples of cycloalkylenes include

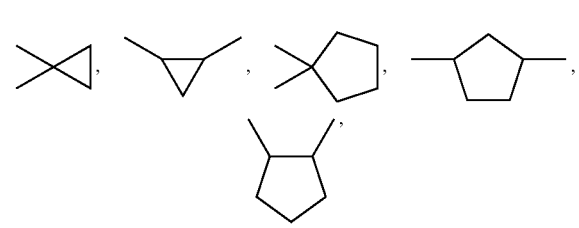

etc.

"Arylcycloalkyl means an aryl-cycloalkyl-group in which the aryl and cycloalkyl are as previously described. Non-limiting examples of suitable arylcycloalkyl groups include phenylcyclopentyl and indanyl.

"Heteroarylalkyl" means a heteroaryl-alkyl-group in which the heteroaryl and alkyl are as previously described. Preferred heteroarylalkyls comprise a lower alkyl group. The bond to the parent moiety is through the alkyl group.

"Heteroarylcycloalkyl" means a heteroaryl-cycloalkyl-group in which the heteroaryl and cycloalkyl are as previously described. Non-limiting examples of suitable heteroarylcycloalkyl groups include

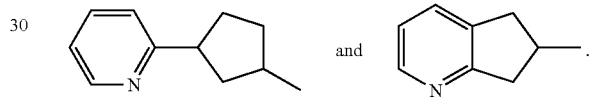

The bond to the parent moiety is through the cycloalkyl group.

"Arylheterocycloalkyl" means an aryl-heterocycloalkyl-group in which the aryl and heterocycloalkyl are a previously described. Non-limiting examples of suitable arylheterocloalkyls include

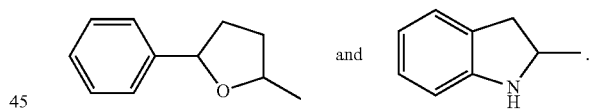

The bond to the parent moiety is through the heterocycloalkyl group.

"Benzo-fused heterocycloalkyl" means an arylheterocloalkyl group as previously defined in which a benzene ring of the aryl group is fused (i.e., shares two ring carbon atoms) with the heterocycloalkyl group. Suitable benzo-fused heterocycloalkyls include

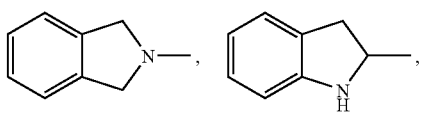

etc.

"Halogen" or "halo" means fluorine, chlorine, bromine, or iodine. Fluorine, chlorine and bromine are preferred.

"Ring system substituent" means a substituent attached to an aromatic or non-aromatic ring system, which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, arylalkoxycarbonyl, alkylsulfonyl, arylsulfonyl, heteroarylsulfonyl, alkylthio, arylthio, heteroarylthio, arylalkylthio, heteroarylalkylthio, cycloalkyl, heterocycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl (unless expressly defined otherwise). The term "ring system substituent" may also mean a single moiety in which two available hydrogens on two adjacent carbon atoms are simultaneously replaced (e.g., one H on each carbon) on a ring system. Examples of such moiety are methylenedioxy, ethylenedioxy, —C(CH$_3$)$_2$— and the like which form moieties such as, for example:

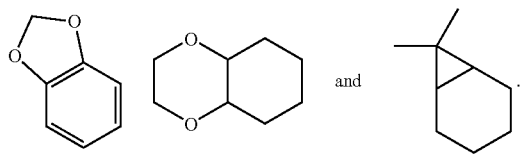

"Heterocycloalkyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may exist in protected form, for example, as an —N(Boc), —N(CBz), —N(Tos) group and the like; such protected forms are also considered part of this invention. The heterocycloalkyl can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of non-aromatic, unsaturated monocyclic heterocycloalkyl rings include thiazolinyl, 2,3-dihydrofuranyl, 2,3-dihydrothiophenyl, etc.

It should be noted that in the hetero-atom containing ring systems of this invention, there are no hydroxyl groups on carbon atoms adjacent to a N, O or S, as well as there are no N or S groups on carbon atoms adjacent to another heteroatom. Thus, for example, in the ring:

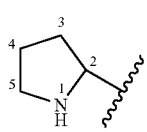

there is no —OH attached directly to carbons marked 2 and 5.

It should also be noted that tautomeric forms such as, for example, the moieties:

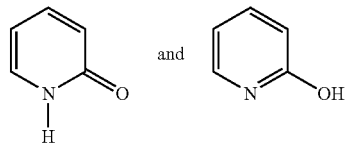

are considered equivalent in this invention.

"Heteroaralkyl" means a heteroaryl-alkyl-group in which the heteroaryl and alkyl moieties are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Arylalkylthio" means an aralkyl-S— group in which the arylalkyl group is as previously described. Non-limiting example of a suitable arylalkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylalkoxycarbonyl" means an arylalkyl-O—C(O)— group. A non-limiting example of a suitable arylalkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is a lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When a group is substituted with "one or more" substituents, the indicated group may be substituted with one substituent, two substituents, etc., provided that the resulting substituted group forms a stable structure, as described above.

The term "optionally substituted" means optional substitution with the specified groups, radicals or moieties. For example, an aryl optionally substituted with an indicated group of substituents includes unsubstituted aryl as well as aryl substituted with any of the indicated substituents.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon atom as well as any heteroatom with unsatisfied valences in the text, schemes, examples, Tables, etc. herein is assumed to have the sufficient number of hydrogen atom(s) to satisfy the valences.

When a functional group in a compound is termed "protected", this means that the group is present in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York, herein incorporated by reference in its entirety.

When any variable (e.g., aryl, heterocycloalkyl, R$^2$, etc.) occurs more than one time in any constituent or in Formula I, its definition on each occurrence is independent of its definition at every other occurrence (unless otherwise expressly indicated).

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are H$_2$O.

"Effective amount" or "therapeutically effective amount" is meant to describe an amount of compound or a composition of the present invention effective in preventing the formation and/or deposition of amyloid protein, and thus producing the desired therapeutic, ameliorative, inhibitory or preventative effect.

The compounds of Formula I can form salts, which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates and prodrugs of the compounds of Formula I, are intended to be included in the present invention.

The compounds according to the invention have pharmacological properties; in particular, the compounds of Formula I can inhibit gamma-secretase, and are therefore useful in the treatment or prevention of neurodegenerative diseases, e.g., Alzheimer's Disease.

Representative compounds of the invention include but are not limited to the compounds of Examples 1-35.

Pharmaceutical compositions can comprise one or more of the compounds of formula I. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., herein incorporated by reference in its entirety.

Liquid form preparations include solutions, suspensions and emulsions. Water or water-propylene glycol solutions for parenteral injection or addition of sweeteners and opacifiers for oral solutions, suspensions and emulsions are examples. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

EXAMPLES

The invention disclosed herein is exemplified by the following preparations and examples, which should not be construed to limit the scope of the disclosure. Alternative mechanistic pathways and analogous structures will be apparent to those skilled in the art.

Where NMR data are presented, $^1$H spectra were obtained on either a Varian Gemini-300 (300 MHz) or XL-400 (400 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Alltech platinum C18, 3 micron, 33 mm×7 mm ID; gradient flow: 0 min—10% $CH_3CN$ in water, 5 min—95% $CH_3CN$ in water, 7 min—95% $CH_3CN$ in water, 7.5 min—10% $CH_3CN$ in water, 9 min. The retention time and observed parent ion are given.

The following solvents and reagents may be referred to by their abbreviations in parenthesis:

"AcOH" means acetic acid.
"Boc" means tert-butoxycarbonyl.
"BOP reagent" means benzotriazole-1-yl-oxy-tris-(dimethylamino)-phosphoniumhexafluorophosphate.
"CBz" means the protecting group carbobenzyloxy.
"DCM" means dichloromethane.
"DCE" means 1,2-dichloroethylene.
"DDQ" means 2,3-dichloro-5,6-dicyano-1,4-benzoquinone.
"DIBAH" means diisobutylaluminum hydride.
"DEAD" means diethylazodicarboxylate.
"DMF" means dimethylformamide.
"EDCI" means 1-(3-dimethylaminopropyl)-3-ethylcarbodiimide.
"Et$_2$O" means diethyl ether.
"EtOAc" means ethyl acetate.
"EtOH" means ethyl alcohol.
"HOBT" means 1-hydroxybenzotriazole.
"LAH" or "LiAlH$_4$" means lithium aluminum hydride.

"LCMS" means liquid chromatography with low resolution mass spectrometry.
"mCPBA" means meta-chloroperbenzoic acid.
"Me" means methyl.
"MeOH" means methanol.
"MS" means mass spectrometry.
"NaOH" means sodium hydroxide.
"NMR" means nuclear magnetic resonance.
"HRMS" means high resolution mass spectrometry.
"OTBDMS" means t-butyldimethylsilyloxy (or t-butyldimethylsilyl ether).
"OTBDPS" means t-butyldiphenylsilyloxy (or t-butyldiphenylsilyl ether).
"P" means a protecting group (except as otherwise noted, e.g., when P refers to a phosphorous atom, as in PPh$_3$).
"Ph" means phenyl.
"PMBCl" means 4-methoxybenzylchloride,
"PPh$_3$" means triphenylphosphine.
"RT" means room temperature.
"TBAF" means tetrabutylammonium fluoride.
"TBDMS" means represent t-butyldimethylsilyl.
"TBDMSCl" means t-butyldimethylsilyl chloride.
"TBDMSOTf" means t-butyldimethylsilyl triflate.
"TBDPSCl" means t-butyldiphenylsilylchloride.
"TBDMS" or "TBS" means represent t-butyldimethylsilyl.
"TFA" means trifluoroacetic acid.
"THF" means tetrahydrofuran.
"TMS" means trimethylsilane.
"TMSCl" means trimethylsilyl chloride.
"Tos" or "tosyl" means toluene sulfonyl.

Compounds of Formula I can be prepared by various methods well known to those skilled in the art, and by the methods described below. The following methods are typical:

Method 1

In Method 1, compounds of Formula I having the structure A are prepared.

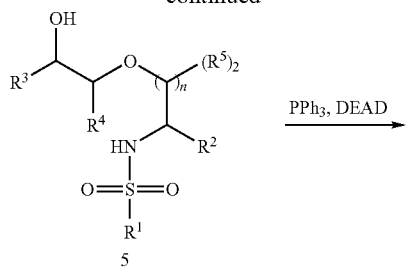

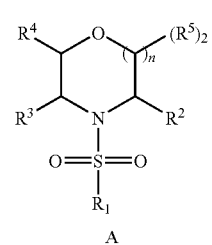

An aminoalcohol 1 is converted to a sulfonamide 2 by reaction with a sulfonyl halide in the presence of a base such as triethylamine or potassium carbonate. The sulfonamide 2 is then reacted with a diazoketone 3 in the presence of a catalyst such as indium (III) triflate. The resulting ketone 4 is then reduced using a reducing agent such as sodium borohydride, and the intermediate sulfonamide alcohol 5 is cyclized to the final compound of structure A using a phosphine such as triphenylphosphine and a diazoester such as DEAD or a diazoamide.

Method 2

In Method 2, compounds of Formula I having the structure B are prepared.

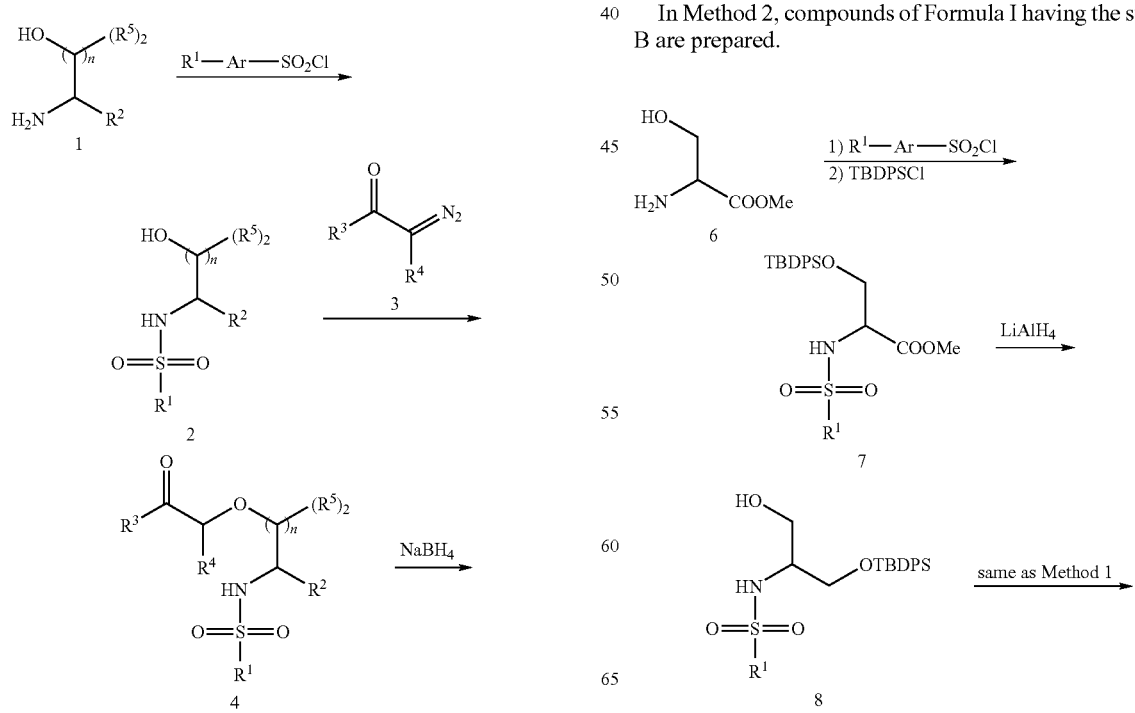

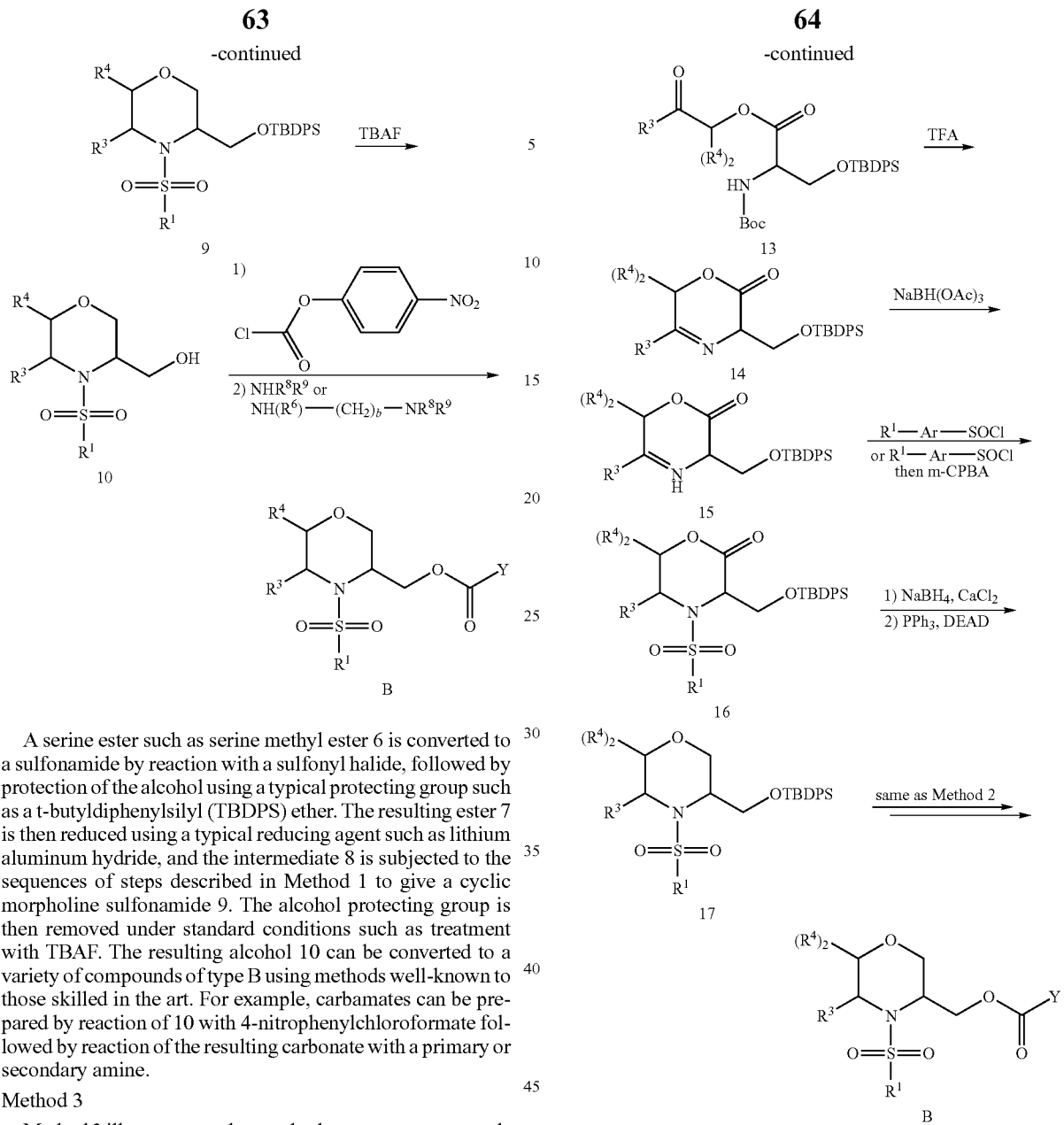

A serine ester such as serine methyl ester 6 is converted to a sulfonamide by reaction with a sulfonyl halide, followed by protection of the alcohol using a typical protecting group such as a t-butyldiphenylsilyl (TBDPS) ether. The resulting ester 7 is then reduced using a typical reducing agent such as lithium aluminum hydride, and the intermediate 8 is subjected to the sequences of steps described in Method 1 to give a cyclic morpholine sulfonamide 9. The alcohol protecting group is then removed under standard conditions such as treatment with TBAF. The resulting alcohol 10 can be converted to a variety of compounds of type B using methods well-known to those skilled in the art. For example, carbamates can be prepared by reaction of 10 with 4-nitrophenylchloroformate followed by reaction of the resulting carbonate with a primary or secondary amine.

Method 3

Method 3 illustrates another method to prepare compounds of Formula I having the structure B.

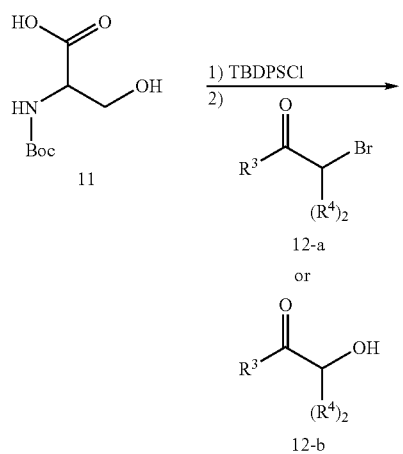

A serine protected at its nitrogen with a protecting group such as Boc is protected at the alcohol with a typical protecting group such as a t-butyldiphenylsilyl ether, and the resulting acid is reacted with either a haloalkylketone (such as 12-a) in the presence of a base such as potassium hydroxide, or alternatively with a hydroxyalkylketone (such as 12-b) in the presence of activating agents such as N,N'-dicyclohexycarbodiimide and 4-dimethylaminopyridine, to give ketoester 13. The serine N-protecting group is then removed under standard conditions such as TFA in case of a Boc-protecting group followed optionally by neutralization with a base such as potassium carbonate, and the intermediate 14 is reduced with a typical reducing agent such as sodium triacetoxy borohydride, with or without the help of an activation agent such as TMSCl to provide an amine 15. The amine 15 is then converted to a sulfonamide 16 by reacting with a sulfonyl halide, or alternatively by reacting with a sulfinyl halide followed by oxidation with an oxidizing agent such as mCPBA. The ester part of the sulfonamide 16 is then opened and reduced with a typical reducing agent such as sodium borohydride with calcium chloride, and the resulting diol is cyclized back to a morpholine 17 using a variety of methods known to those skilled in the art, for example using triphenylphosphine and DEAD (Mitsunobu-type procedure), or tosylchloride and pyridine. Morpholine 9 can then be converted into compounds of structure B using procedures described in Method 2.

Method 4

In Method 4, compounds of Formula I having the structure C are prepared.

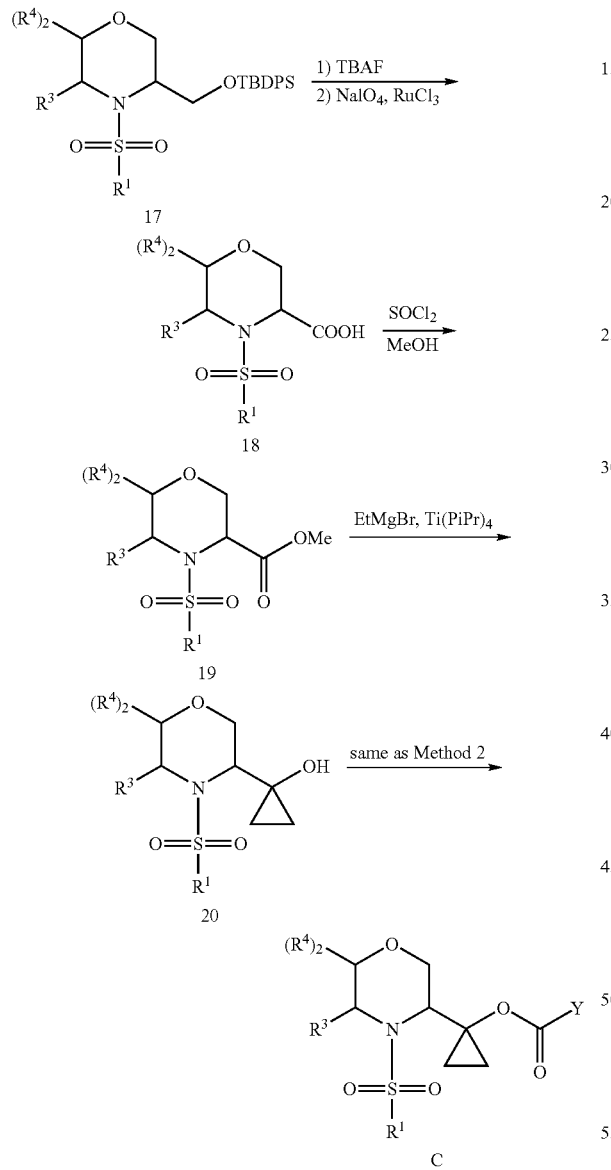

Protected alcohol intermediate 17 is deprotected with a typical deprotection agent such as TBAF, then oxidized to an acid 18 using a standard procedure such as sodium periodate and ruthenium chloride. The acid is then converted to an ester such as methyl ester 19 using a standard esterification procedure such as thionyl chloride and methanol. The ester 19 is then converted to a cyclopropanol 20 using standard procedures such as the Kulinkovich reaction using conditions such as ethylmagnesium bromide and titanium IV isopropoxide.

This alcohol 20 is finally converted into compounds of structure C using procedures described in Method 2.

Method 5

In Method 5, compounds of Formula I having the structure D are prepared.

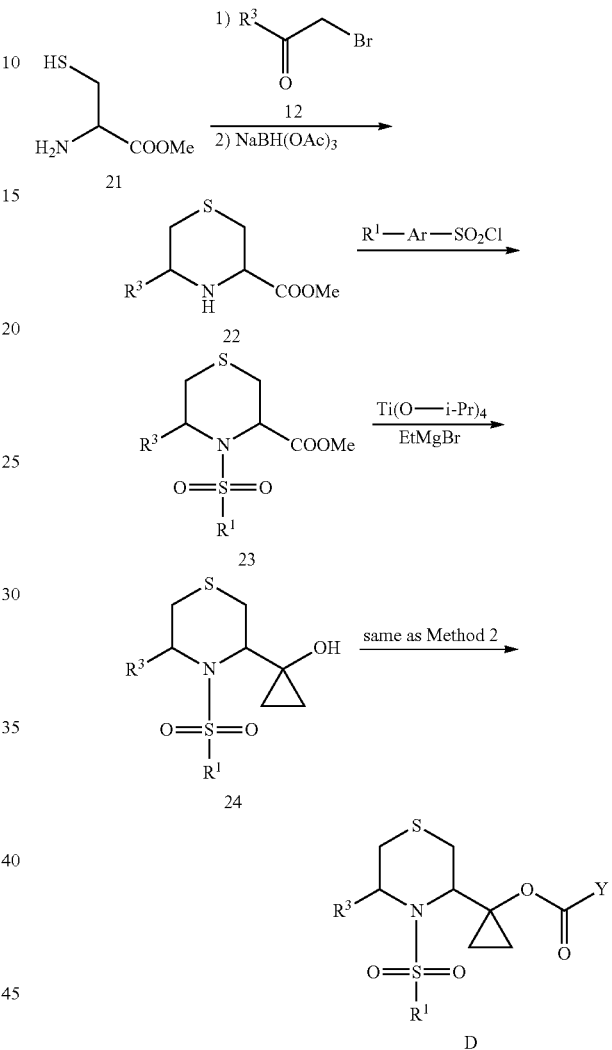

A cysteine ester such as cysteine methyl ester 21 is reacted with a halomethylketone such as bromoketone 12 in the presence of a base such as potassium hydroxide and the intermediate imine is reduced with a typical reducing agent such as sodium triacetoxyborohydride to give a thiomorpholine 22. This thiomorpholine 22 is then converted to a sulfonamide 23 by reaction with a sulfonyl halide and the ester part of the molecule is then converted to a cyclopropane alcohol 24 using a Kulinkovich reaction (Kulinkovich, O. G. Chem Review 100 (2000), 2789; incorporated herein by reference in its entirety). Finally, the alcohol 24 is converted into compounds of structure D using procedures described in Method 2.

Chiral compounds of this invention can be resolved using known methods, for example by chromatography over a chiral stationary phase.

The invention disclosed herein is further exemplified by the following examples, which should not be construed as limiting the scope of the invention. Alternative mechanistic pathways and analogous structures within the scope of the invention will be apparent to those skilled in the art.

Example 1

4-(2-Hydroxy-ethyl)-piperazine-1-carboxylic acid 4-(4-chloro-benzenesulfonyl)-5-(3,5-difluoro-phenyl)-morpholin-3-ylmethyl ester

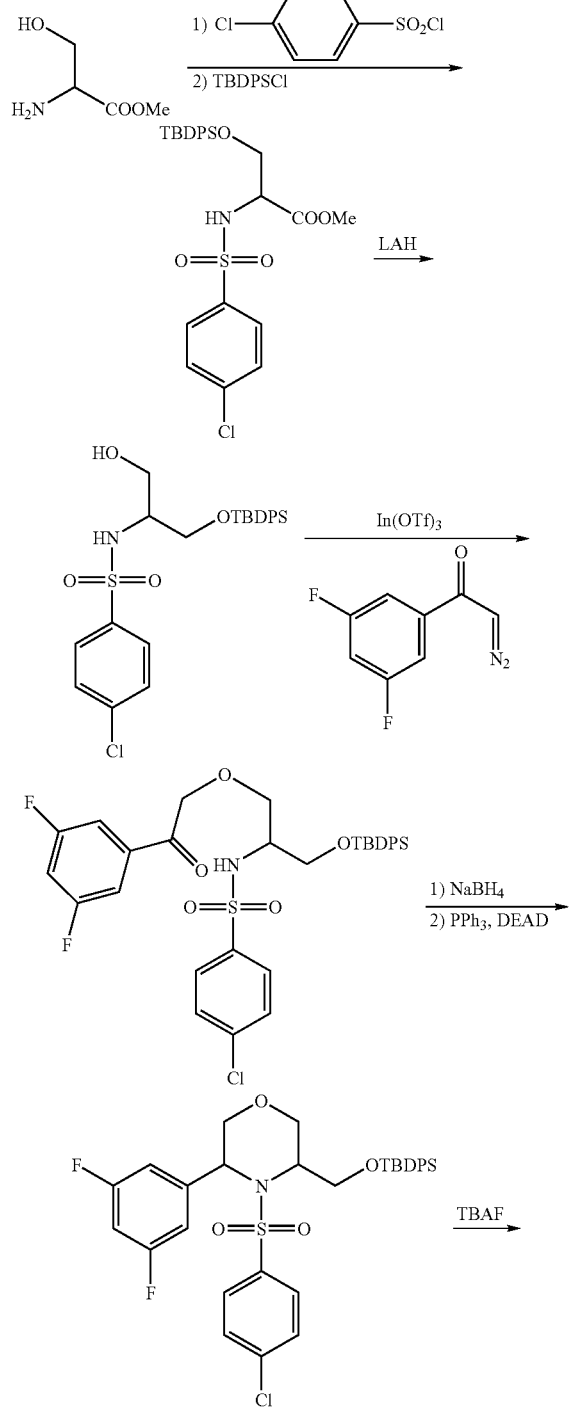

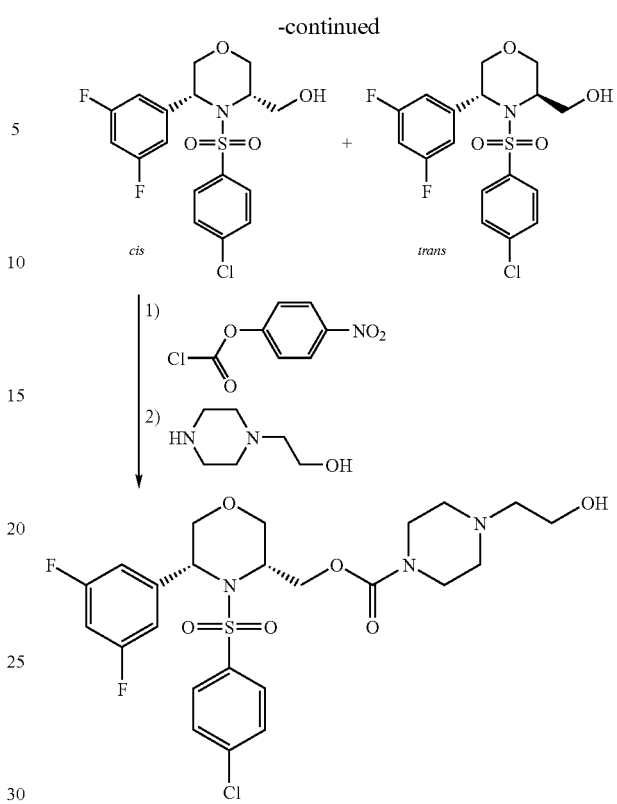

Example 1

Step 1

To a solution of DL-serine methyl ester hydrochloride (30 g, 0.19 mol) in water (150 mL) at 0° C. was added potassium carbonate (79 g, 0.57 mol) then 4-chlorobenzenesulfonyl chloride (44 g, 0.21 mol) in THF (150 mL) and the reaction was allowed to warm to RT for 3 h. The mixture was then diluted with water and extracted with $Et_2O$ and EtOAc. The combined organic layers were washed with 5% citric acid solution, brine, then dried over sodium sulfate and concentrated to give 48.5 g (88%) of sulfonamide.

Step 2

A solution of sulfonamide product from Step 1 (10 g, 34.0 mmol), TBDPSCl (10.3 g, 37.4 mmol) and imidazole (2.8 g, 41 mmol) in DMF (50 mL) was stirred at RT overnight. The mixture was poured into a mixture of water and brine (1:1), extracted with $Et_2O$, washed with brine, dried over sodium sulfate and concentrated. The residue was purified by flash-chromatography over silica gel (eluted with hexanes/DCM 1:1 to DCM) to obtain 16.0 g (89%) of O-protected sulfonamide.

Step 3

To a solution of O-protected sulfonamide product of Step 2 (55.8 g, 0.10 mol) in THF (600 mL) was added LAH 1N in DCM (100 mL, 0.10 mol) at 0° C. and the solution was allowed to warm to RT for 1 h. The mixture was quenched with excess EtOAc and 0.5 N NaOH, diluted with EtOAc, filtered over Celite, then extracted with EtOAc and DCM, dried over sodium sulfate and concentrated. The residue was purified by flash-chromatography over silica gel (eluted with DCM/EtOAc 100:0 to 70:30) to give 39.5 g (75%) of alcohol.

Step 4

To a solution of alcohol product of Step 3 (28.8 g, 0.057 mol) in DCM (200 mL), was added 2-diazo-1-(3,5-difluorophenyl)-ethanone (9.6 g, 0.052 mol) and the reaction mixture was stirred at RT for 15 minutes. Indium (III) triflate (5.7 g, 0.012 mol) was then added in four equal portions every hour over 4 hr and the mixture was stirred at RT overnight. Additional Indium (III) triflate (1.4 g, 0.0028 mol) was again added to the reaction in four portions, as before, and the mixture was stirred at room temperature overnight. After concentration of the solvent, the residue was purified by flash-chromatography over silica gel (eluted with hexanes/EtOAc 100:0 to 1:1) to provide 4.0 g of ketone product as well as 23.5 g of recovered alcohol starting material (from Step 3). This alcohol (23.5 g) was then subjected to the same conditions described above to provide another 3.30 g of ketone product as well as 18.5 g of recovered alcohol starting material from Step 3. This alcohol (18.5 g) was finally subjected to the same conditions described above to provide another 2.60 g of ketone product as well as 14.8 g of recovered starting material alcohol from Step 3 (51% recovery). 9.90 g (26%) of the combined ketone product was obtained.

Step 5

To a solution of the ketone product of Step 4 (12.2 g, 18.5 mmol) in MeOH (150 mL) at 0° C. was added sodium borohydride (700 mg, 18.5 mmol) and the reaction mixture was stirred for 1 h. The mixture was then diluted with half-brine, extracted with DCM and EtOAc, dried over sodium sulfate and concentrated. The residue was purified by flash-chromatography over silica gel (eluted with DCM/EtOAc 100:0 to 40:60) to give 8.0 g (67%) of alcohol.

Step 6

To a solution of the alcohol product of Step 5 (9.5 g, 14.4 mmol) and triphenylphosphine (5.7 g, 21.7 mmol) in THF (90 mL) was added DEAD (3.4 mL, 21.7 mmol), and the mixture was stirred at RT overnight then concentrated. The residue was purified by flash-chromatography over silica gel (eluted with a gradient of hexanes/EtOAc) to give 6.0 g (65%) of O-protected morpholine.

Step 7

To a solution of the O-protected morpholine product of Step 6 (9.5 g, 14.4 mmol) in THF (100 mL) was added TBAF 1N in THF (9.3 mL, 9.3 mmol) and the reaction was stirred 1 h at RT. It was then concentrated, diluted with DCM and 50% NaHCO$_3$, then extracted with DCM and EtOAc. The combined organic layers were dried over sodium sulfate, concentrated, and the residue was purified by flash-chromatography over silica gel (eluted with a gradient of DCM/EtOAc) to afford, in order of elution, 1.5 g (41%) of cis-morpholine alcohol, followed by 1.5 g (41%) of trans-morpholine alcohol.

Step 8

To a solution of cis-morpholine alcohol product of Step 7 (52 mg, 0.13 mmol) in acetonitrile/THF (1/1 mL) was added pyridine (50 μL) then 4-nitrophenyl chloroformate (40 mg, 0.2 mmol) and the reaction was heated at 65° C. overnight. The mixture was concentrated, and then purified by flash-chromatography over silica gel (eluted with a gradient of hexanes/DCM) to provide 61 mg of nitrophenylcarbonate.

Step 9

To a solution of nitrophenylcarbonate product of Step 8 (19 mg, 0.033 mmol) in DCE (1 mL) was added N-(2-hydroxyethyl)piperazine (100 mg), and the reaction was stirred at RT overnight. The final mixture was diluted with DCM and 0.5 N NaOH, extracted with EtOAc and DCM, dried over sodium sulfate and concentrated, and the residue was purified over preparative silica gel (eluted with DCM/MeOH 9:1) followed by treatment with 1N HCl in Et$_2$O to obtain 20.2 mg of product, i.e., Example 1, as a hydrochloride salt. $^1$H NMR (CDCl$_3$ 400 MHz) δ 7.82 (d, J=8.8 Hz, 2H), 7.55 (d, J=8.8 Hz, 2H), 7.22 (m, 2H), 6.77 (m, 1H), 4.85 (m, 1H), 4.38 (d, 1H), 4.10 (m, 1H), 3.91 (m, 1H), 3.40-3.75 (m, 10H), 3.15-3.30 (m, 2H), 2.40-2.65 (m, 5H); HRMS (MH$^+$)=560.1434.

Following procedures similar to those of Example 1 and using either cis-morpholine alcohol or trans-morpholine alcohol, i.e., the products of Step 7, the compounds in Table 2 were prepared:

TABLE 2

| Example No. | COMPOUND | Mass Spec (M$^+$); retention time (min) |
|---|---|---|
| 2 | 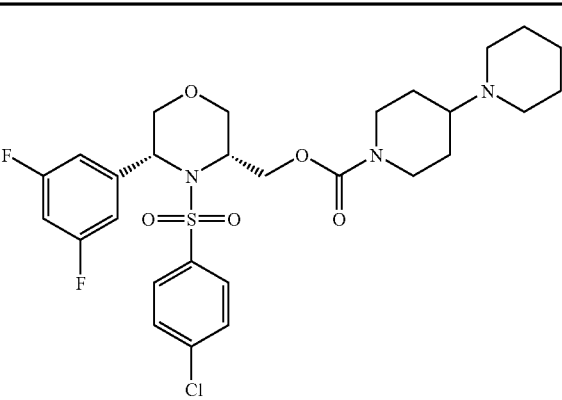 | 598.1; 3.73 |

TABLE 2-continued
| Example No. | COMPOUND | Mass Spec (M+); retention time (min) |
|---|---|---|
| 3 | | 598.1; 3.77 |
| 4 | | 560.1; 3.44 |
| 5 | | 573.1; 4.51 |
Example 6
4-Hydroxy-piperidine-1-carboxylic acid 1-[4-(4-chloro-benzenesulfonyl)-5-propyl-morpholin-3-yl]-cyclopropyl ester
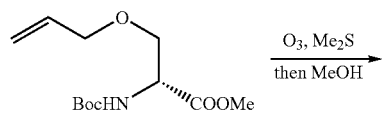
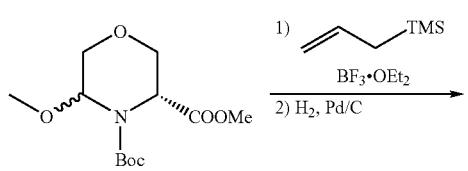
-continued

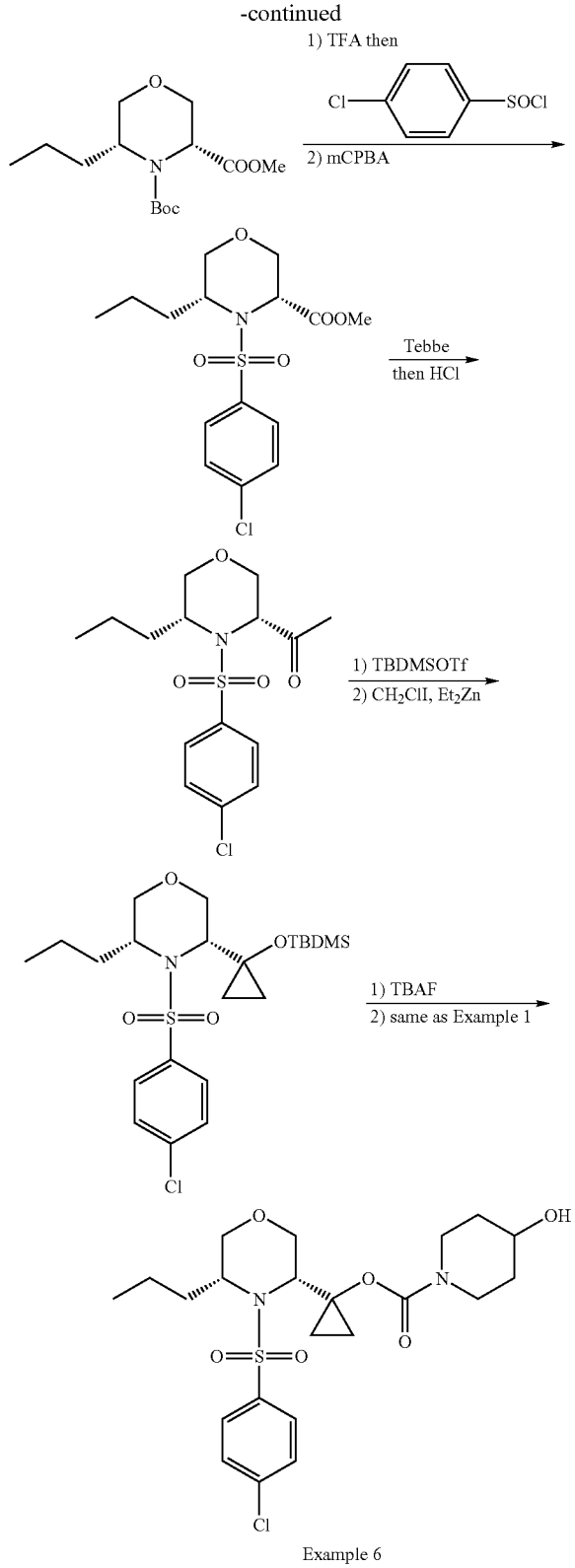

Example 6

5-Methoxy-morpholine-3,4-dicarboxylic acid 4-tert-butyl ester 3-methyl ester (product of Step 1) was prepared according to the procedures described in U.S. Patent Publication Nos. 2003236296 and 2004014753 which are herein incorporated by reference.

Step 1

A solution of N-(tert-butoxycarbonyl)-O-allyl-D-serine methyl ester (9.55 g, 36.8 mmol) in DCM (100 mL) and MeOH (50 mL) was cooled to −78° C. and treated with ozone until the greenish color persisted. The solution was then purged with nitrogen gas, treated with dimethylsulfide (11.2 mL) and allowed to warm to RT overnight. After concentration, the crude product was taken up in MeOH (120 mL) and treated with p-toluenesulfonic acid (150 mg) for 4 h, then concentrated. The residue was purified by flash-chromatography over silica gel (eluted with hexanes/EtOAc 90:10 to 50:50) to afford 5.02 g (50%) of aminal.

Step 2

To a solution of aminal product from Step 1 (5.02 g, 18.2 mmol) in DCM (80 mL) at −78° C. were successively added allyltrimethylsilane (6.00 mL, 37.8 mmol) then boron trifluoride diethyletherate (560 μL) and the reaction was stirred 1 h at −78° C. The solution was then quenched in water, extracted twice with DCM, dried over sodium sulfate and concentrated. The crude product was purified by flash-chromatography over silica gel (eluted with hexanes/EtOAc 90:10 to 60:40) to give 3.16 g (61%) of allyl product.

Step 3

A solution of allyl product from Step 2 (3.00 g, 10.5 mmol) and palladium 10% over charcoal (300 mg) in EtOAc (10 mL) and MeOH (10 mL) was hydrogenated at 1 atm for 6 h, filtered over Celite and concentrated to yield 3.02 g (100%) of n-propyl product.

Step 4

A solution of n-propyl product from Step 3 (1.96 g, 6.82 mmol) in DCM (15 mL) and TFA (5 mL) was stirred at RT for 2 h then concentrated. The residue was taken up in DCM and ice-cooled 0.1 N NaOH, extracted with DCM and EtOAc, dried over sodium sulfate and concentrated. The residue was taken up in DCM (20 mL), treated with triethylamine (2.00 mL, 14.3 mmol) and 4-chlorobenzenesulfonyl chloride (2.07 g, 10.6 mmol), and stirred overnight at RT. It was then diluted with water and extracted with DCM, dried over sodium sulfate and concentrated. The residue was purified by flash-chromatography over silica gel (eluted with hexanes/EtOAc 95:5 to 40:60) to give 712 mg of sulfonamide isomer A and 434 mg of isomer B (total yield 49%).

Step 5

A solution of sulfonamide isomers A and B products of Step 4 (1.15 g, 3.33 mmol) in DCM (20 mL) was treated with mCPBA (1.20 g, 6.96 mmol) and the reaction was stirred at RT overnight. The solution was then poured into 5% sodium carbonate and extracted with DCM, dried over sodium sulfate and concentrated. The residue was purified by flash-chromatography over silica gel (eluted with hexanes/EtOAc 90:10 to 50:50) to give 1.08 g (89%) of ester sulfonamide.

Step 6

To a solution of ester sulfonamide product of Step 5 (653 mg, 1.80 mmol) in THF (22 mL) at 0° C. was slowly added a 1 N solution in toluene of Tebbe's reagent (Aldrich) (14.5 mL) followed, 10 min later, by pyridine (1.20 mL, 14.5 mmol) and the reaction mixture was allowed to warm to RT for 4 h. The reaction mixture was then quenched with EtOAc, and slowly poured onto ice. Celite and brine were then added and the resulting slurry was stirred 30 min at RT. The slurry was then filtered over Celite, rinsed with EtOAc/MeOH (9:1) and brine, then extracted with EtOAc, dried over sodium sulfate and concentrated. The resulting residue was purified by flash-chromatography over silica gel (eluted with hexanes/DCM 75:25 to 0:100) to give 352 mg of an intermediate enol ether. This enol ether (352 mg) was taken up in THF (10 mL) and treated with HCl 1N (10 mL) at RT for 2 h. The crude product was then diluted with water, extracted with DCM and EtOAc, dried over sodium sulfate and concentrated to give 335 mg (54%) of ketone.

Step 7

To a solution of the ketone product of Step 6 (345 mg, 1.00 mmol) and triethylamine (310 µL, 0.22 mmol) in DCM (4 mL) at 0° C. was slowly added t-butydimethysilyl triflate (250 µL, 1.10 mmol) and the reaction was allowed to warm at RT overnight. The final mixture was concentrated and purified by flash-chromatography over silica gel (eluted with hexanes/DCM 7:3 to DCM) to provide 417 mg (91%) of enol silyl ether.

Step 8

To a solution of diethylzinc 1N in hexanes (6.4 mL, 6.4 mmol) in DCM (12 mL) at 0° C. was slowly added chloroiodomethane (465 µL, 6.4 mmol) followed, 10 min later, by the enol silyl ether product of Step 7 (417 mg, 0.91 mmol) in DCM (12 mL). The solution was slowly allowed to warm to RT and stirred 3 h. It was then poured into 20% ammonium chloride solution, extracted with DCM, dried over sodium sulfate and concentrated to give 417 mg (97%) of O-protected cyclopropanol.

Step 9

A solution of the O-protected cyclopropanol product of Step 8 (417 mg, 0.88 mmol) and TBAF 1 N (2.0 mL, 2.0 mmol) in THF (4 mL) was stirred at RT overnight, then concentrated. The residue was directly purified by flash-chromatography over silica gel (eluted with hexanes/EtOAc 85:15 to 0:100) to give 257 mg (81%) of cyclopropanol.

Step 10

The cyclopropanol product of Step 9 was subjected to conditions similar to those described in Example 1, Steps 8 and 9, using 4-hydroxypiperidine instead of N-(2-hydroxyethyl)piperazine in the last step, to give the desired product, i.e., Example 6. $^1$H NMR (CDCl$_3$ 400 MHz) δ 7.76 (d, J=8.8 Hz, 2H), 7.47 (d, J=8.8 Hz, 2H), 4.55 (m, 1H), 3.65-4.10 (m, 3H), 3.50-3.65 (m, 2H), 3.38 (d, 1H), 3.26 (m, 1H), 2.80-3.00 (m, 3H), 1.40-2.20 (m, 9H), 1.20-1.40 (m, 2H), 1.05-1.15 (m, 2H), 0.99 (t, J=7.5 Hz, 3H); HRMS (MH$^+$)=487.1658.

The compounds in Table 3 were prepared following procedures similar to those of Example 6:

TABLE 3

| Example No. | COMPOUND | Mass Spec (M$^+$); retention time (min) |
|---|---|---|
| 7 | | 554.3; 3.37 |
| 8 | | 516.3; 2.95 |

TABLE 3-continued
| Example No. | COMPOUND | Mass Spec (M+); retention time (min) |
|---|---|---|
| 9 | 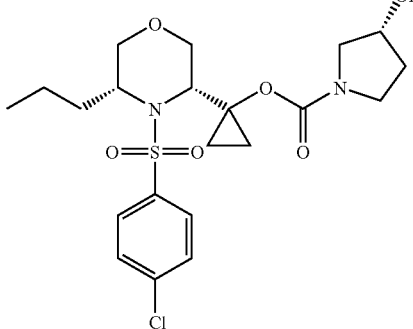 | 473.3; 3.69 |
| 10 | 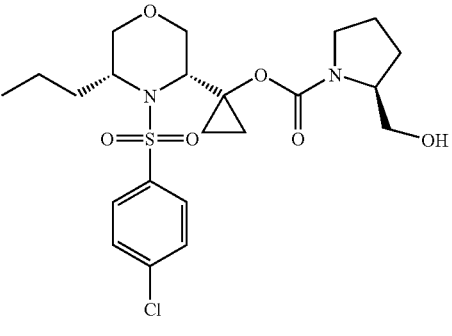 | 487.3; 4.12 |
| 11 | 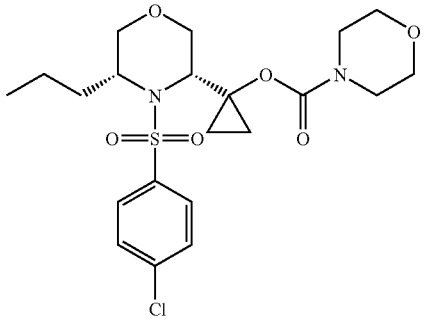 | 473.3; 4.29 |
| 12 | 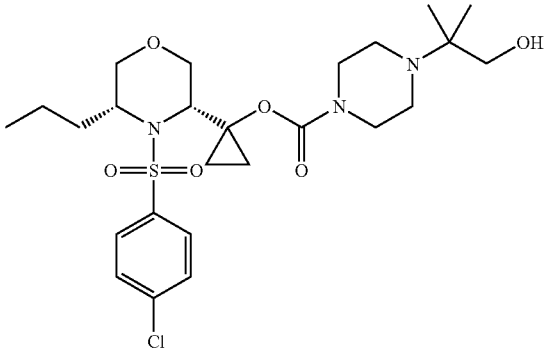 | 544.3; 3.12 |

TABLE 3-continued

| Example No. | COMPOUND | Mass Spec (M+); retention time (min) |
|---|---|---|
| 13 | | 529.3; 5.18 |
| 14 | | 545.3; 3.88 |
| 15 | | 542.1; 3.06 |

Example 16

4-(2-Hydroxy-1,1-dimethyl-ethyl)-piperazine-1-carboxylic acid 1-[4-(4-chloro-benzenesulfonyl)-5-(3,5-difluoro-phenyl)-morpholin-3-yl]-cyclopropyl ester

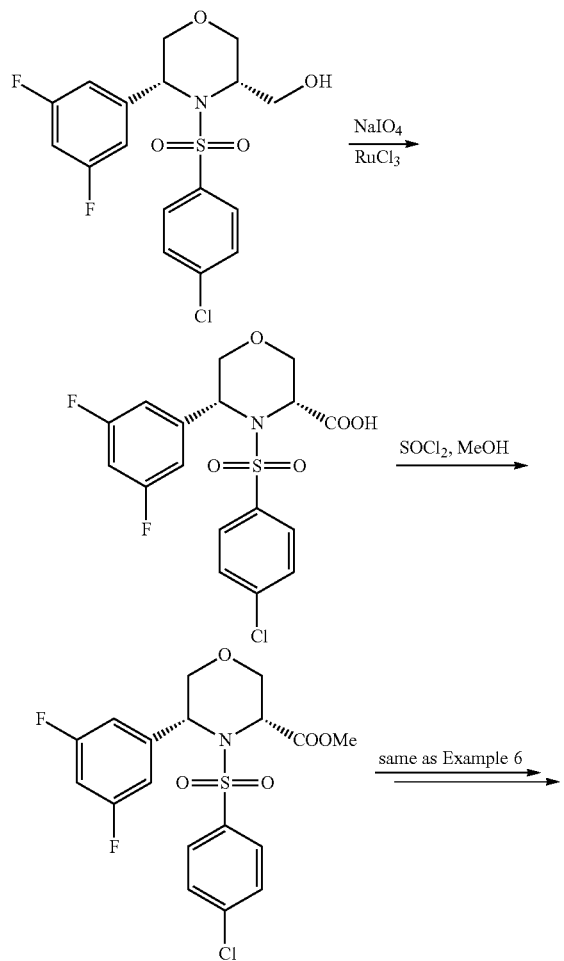

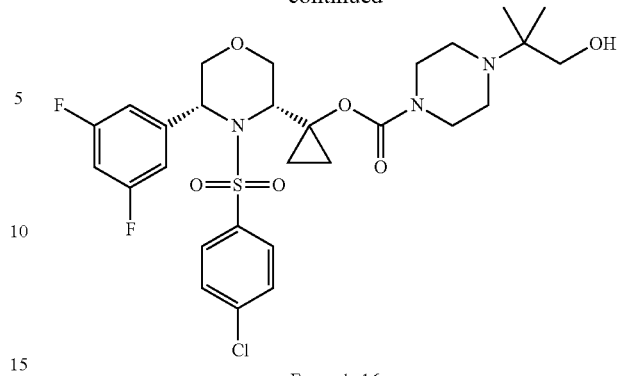

Example 16

Step 1

To a solution of the cis-morpholine alcohol product of Example 1, Step 7 (520 mg, 1.3 mmol) in EtOAc (4 mL), acetonitrile (4 mL) and water (8 mL), was added sodium periodate (770 mg, 3.6 mmol) then ruthenium (III)chloride hydrate (50 mg) and the mixture was stirred at RT overnight. The reaction was filtered over Celite, and the filtrate was extracted with EtOAc, dried over sodium sulfate and concentrated to provide 580 mg of crude acid.

Step 2

To a solution of the crude acid from Step 1 (477 mg, 1.15 mmol) in MeOH (10 mL) was added thionyl chloride (0.25 ml, 3.5 mmol), and then the reaction was heated at 60° C. for 2 h. The mixture was then concentrated, neutralized with saturated sodium bicarbonate, extracted with DCM and EtOAc, dried over sodium sulfate and concentrated to give 453 mg (92%) of ester.

Step 3

The ester product of Step 2 was subjected to conditions similar to those described in Example 6, Steps 6 to 10, using 2-methyl-2-piperazin-1-yl-propan-1-ol instead of N-(2-hydroxyethyl)piperazine in the last step, to give the desired product, i.e., Example 16. $^1$H NMR (CDCl$_3$ 400 MHz) δ 7.84 (d, J=8.7 Hz, 2H), 7.55 (d, J=8.7 Hz, 2H), 4.90 (m, 1H), 4.76 (m, 1H), 4.36 (m, 1H), 3.20-3.70 (m, 4H), 2.95-3.15 (m, 2H), 2.40-2.80 (m, 2H), 1.40-1.80 (m, 6H), 1.08 (s, 6H), 0.70-0.90 (m, 2H), 0.84 (m, 1H), −0.10 (m, 1H); HRMS (MH$^+$)= 614.1892.

The compounds in Table 4 were prepared following procedures similar to those of Example 16:

TABLE 4

| Example No. | COMPOUND | Mass Spec (M$^+$); retention time (min) |
|---|---|---|
| 17 | | 624.1; 3.84 |

TABLE 4-continued

| Example No. | COMPOUND | Mass Spec (M⁺); retention time (min) |
|---|---|---|
| 18 | | 586.1; 3.42 |
| 19 | | 557.1; 4.25 |
| 20 | | 543.1; 4.15 |
| 21 | | 557.1; 4.55 |

TABLE 4-continued

| Example No. | COMPOUND | Mass Spec (M+); retention time (min) |
|---|---|---|
| 22 | | 543.1; 4.78 |
| 23 | | 585.1; 4.69 |
| 24 | | 599.1; 5.52 |
| 25 | | 611.1; 4.81 |

TABLE 4-continued

| Example No. | COMPOUND | Mass Spec (M+); retention time (min) |
|---|---|---|
| 26 | | 625.1; 5.76 |
| 27 | | 650.2; 4.02 |
| 28 | | 583.3; 4.00 |

Example 29

3-Hydroxy-pyrrolidine-1-carboxylic acid 4-(4-chloro-benzenesulfonyl)-5-cyclopropyl-morpholin-3-ylmethyl ester

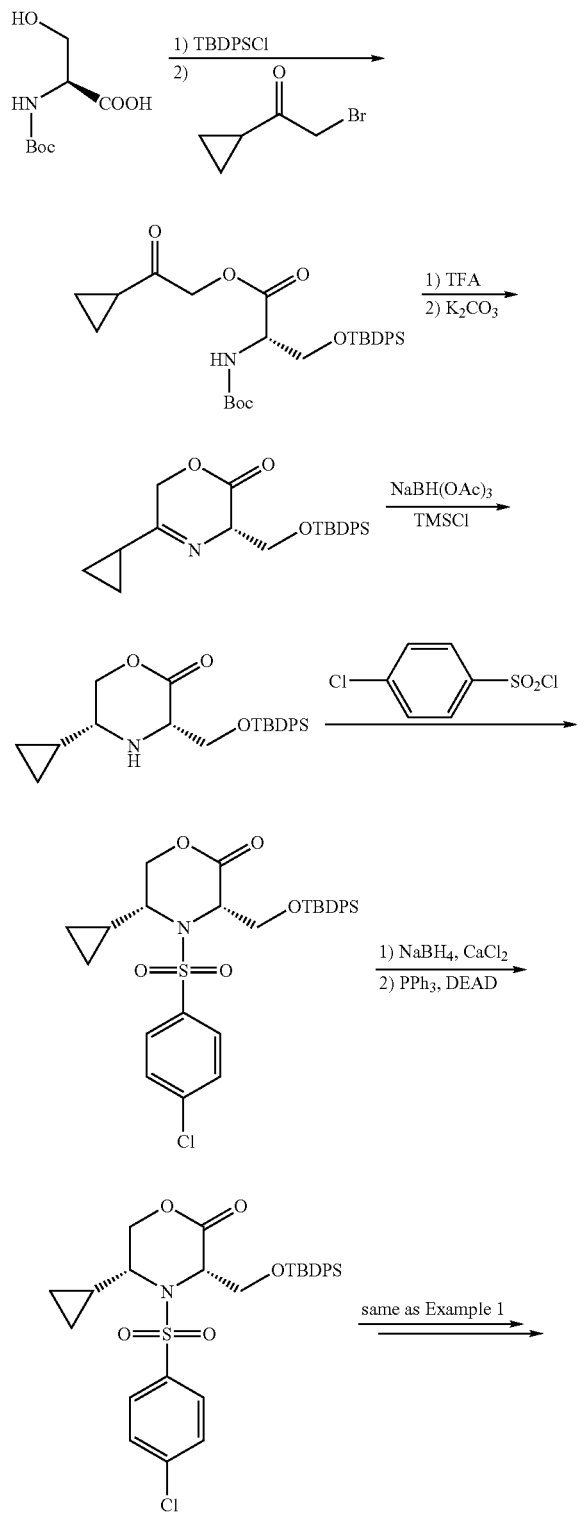

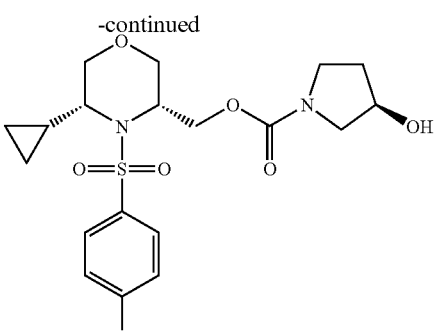

Example 29

Step 1

To a solution of Boc-L-serine (12.95 g, 63.1 mmol) in DCM (150 mL) was added triethylamine (19.7 mL, 140 mmol) followed by TBDPSCl (16.7 mL, 65 mmol) and the reaction mixture was stirred at RT over 2 days. The mixture was then treated with ice-cooled 5% citric acid, extracted with DCM, EtOAc, dried over sodium sulfate and concentrated to provide 28.0 g (100%) of O-protected serine.

Step 2

To a solution of the O-protected serine product of Step 1 (18.71 g, 42.2 mmol) in MeOH (100 mL) and DCM (30 mL) was slowly added potassium hydroxide (2.37 g, 42.2 mmol) in MeOH (100 mL), then the reaction mixture was concentrated. The resulting solid and potassium iodide (700 mg, 4.2 mmol) was taken up in DMF (70 mL) and a solution of 2-bromo-1-cyclopropyl-ethanone (6.88 g, 42.2 mmol) in DMF (30 mL) was slowly added. The reaction was stirred at RT over 2 days. It was then concentrated, diluted with DCM and washed twice with water, dried over sodium sulfate and concentrated. The residue was purified by flash-chromatography over silica gel (eluted with hexanes/EtOAc 85:15 to 50:50) to provide 22.3 g (100%) of ketone.

Step 3

A solution of the ketone product of Step 2 (22.3 g, 42.2 mmol) was stirred in TFA (30 mL) and DCM (100 mL) for 2 h then concentrated. The resulting residue was taken up in DCM (250 mL), excess potassium carbonate was added, and the reaction was stirred at RT overnight. The mixture was then filtered over Celite and concentrated to provide 16.7 g (97%) of imine.

Step 4

To a mixture of the imine product of Step 3 (16.7 g, 41.0 mmol) and sodium triacetoxyborohydride (12.2 g, 57.5 mmol) in acetonitrile (200 mL) at 0° C. was slowly added TMSCl (5.6 mL, 44.0 mmol), then the reaction mixture was allowed to warm to RT and stirred for 3 h. The reaction mixture was then filtered over Celite, concentrated, and the residue was taken up in saturated sodium bicarbonate solution, extracted with EtOAc and DCM, dried over sodium sulfate and concentrated to provide 16.3 g (97%) of amine.

Step 5

To a mixture of the amine product of Step 4 (18.07 g, 44.1 mmol) in pyridine (100 mL) was added 4-chlorobenzenesulfonyl chloride (11.60 g, 55 mmol) and the reaction was stirred at RT for 6 h then concentrated. The residue was purified by flash-chromatography over silica gel (eluted with hexanes/EtOAc 90:10 to 70:30) to provide 19.50 g (76%) of sulfonamide.

Step 6

To a solution of the sulfonamide product of Step 5 (4.50 g, 7.7 mmol) and calcium chloride (5.10 g, 46.2 mmol) in THF (45 mL) and EtOH (65 mL) was added sodium borohydride (0.87 g, 23.1 mmol) in one portion. The reaction was stirred at 0° C. for 20 min then heated to 60° C. for 1 h. The final mixture was diluted with EtOAc, treated with ice-cooled aqueous 5% citric acid solution, extracted with EtOAc and DCM, dried over sodium sulfate and concentrated. The residue was purified by flash-chromatography over silica gel (eluted with hexanes/EtOAc 98:2 to AcOEt) to afford 3.21 g (71%) of diol.

Step 7

To a solution of the diol product of Step 6 (1.68 g, 2.86 mmol) and triphenylphosphine (1.57 g, 6.00 mmol) in toluene (20 mL) was added DEAD (1.05 g, 6.00 mmol), and the solution was stirred overnight at RT. The reaction mixture was then concentrated and subjected to flash-chromatography over silica gel (eluted with hexanes/DCM 75:25 to 0:100) to provide 1.03 g (63%) of morpholine protected alcohol.

Step 8

The morpholine protected alcohol product of Step 7 was subjected to conditions similar to those described in Example 1, Step 7 to Step 9, using (R)-3-hydroxypyrrolidine instead of N-(2-hydroxyethyl)piperazine in the last step, to afford the desired product, i.e., Example 28. $^1$H NMR (CDCl$_3$ 400 MHz) δ 7.72 (d, J=8.8 Hz, 2H), 7.47 (d, J=8.8 Hz, 2H), 4.40-4.55 (m, 2H), 4.31 (m, 1H), 3.97 (m, 1H), 3.70-3.85 (m, 2H), 3.40-3.70 (m, 4H), 3.05-3.20 (m, 2H), 2.99 (m, 1H), 1.90-2.05 (m, 2H), 1.68 (m, 1H), 1.39 (m, 1H), 0.60-0.75 (m, 3H), 0.36 (m, 1H). LCMS (MH$^+$)=445.2, purity >99%.

The compounds in Table 5 were prepared following procedures similar to those of Example 29:

TABLE 5

| Example No. | COMPOUND | Mass Spec (M$^+$); retention time (min) |
|---|---|---|
| 30 | | 526.3; 2.88 |
| 31 | | 459.3; 3.70 |
| 32 | | 560.1; 3.27 |

TABLE 5-continued
| Example No. | COMPOUND | Mass Spec (M+); retention time (min) |
|---|---|---|
| 33 | 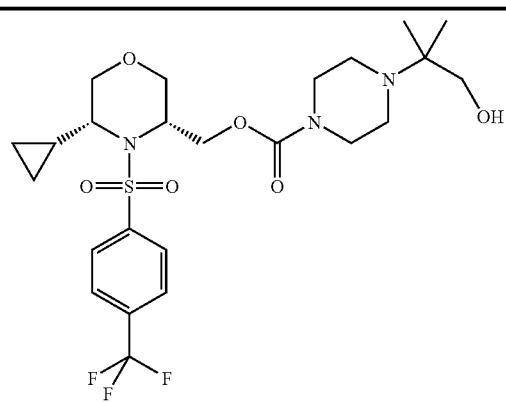 | 549.6; 3.04 |
| 34 | 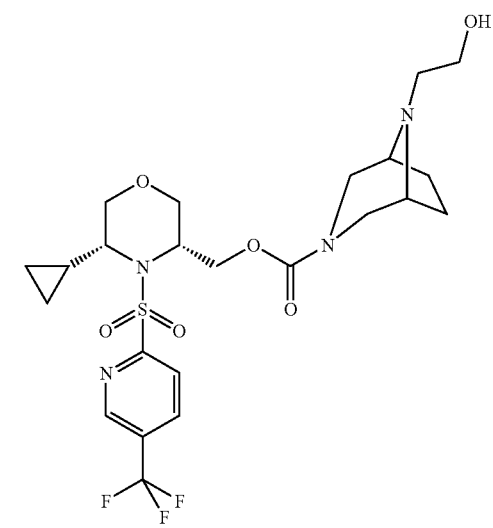 | 549.3; 2.86 |
Example 35
4-(2-Hydroxy-1,1-dimethyl-ethyl)-piperazine-1-carboxylic acid 1-[4-(4-chloro-benzenesulfonyl)-5-cyclopropyl-morpholin-3-yl]-cyclopropyl ester
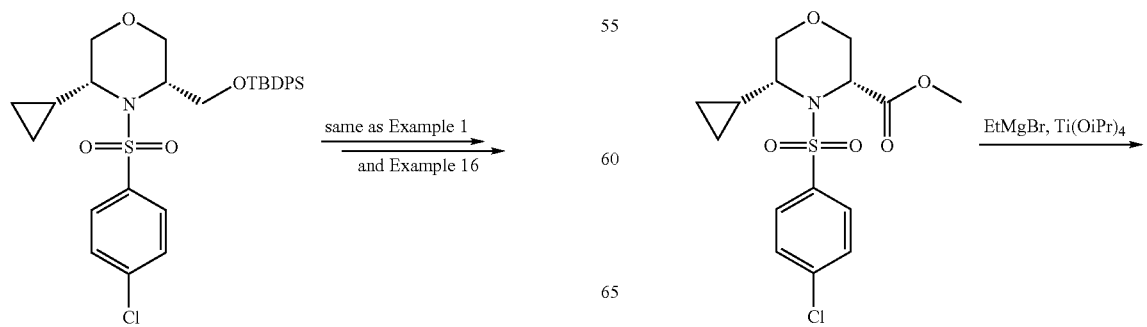

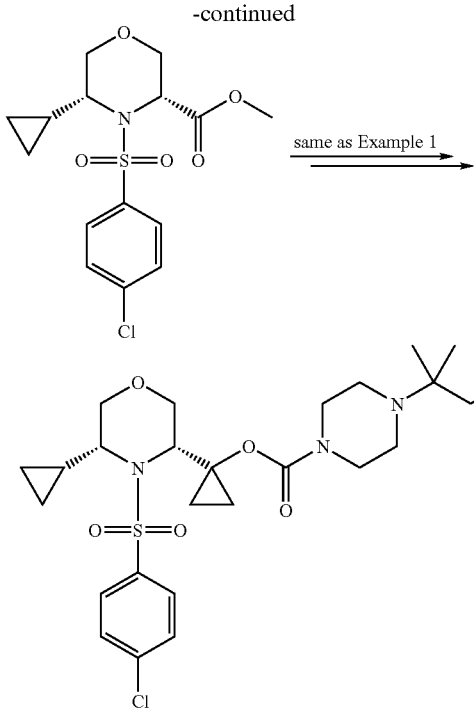

Example 35

Step 1

The morpholine protected alcohol product of Example 29, Step 7 was deprotected following conditions similar to those described in Example 1, Step 7 and the resulting alcohol was subjected to conditions similar to those described in Example 16, Steps 1 to 2, to give an ester.

Step 2

To a solution of ester product of Step 1 (1.90 g, 5.3 mmol) in THF (100 mL) was added titanium(IV)isopropoxide (1.50 g, 5.3 mmol) and the solution was cooled to 0° C. Ethylmagnesium bromide 3N in ether (9.0 mL, 26.5 mmol) was then added via syringe pump over 1 hr period and the reaction was stirred for an additional 30 min at this temperature. The final mixture was diluted with EtOAc, treated with saturated sodium bicarbonate solution, extracted with EtOAc and DCM, dried over sodium sulfate and concentrated. The residue was purified by flash-chromatography over silica gel (eluted with hexanes/EtOAc 95:5 to AcOEt) to give 1.16 g (61%) of morpholine cyclopropanol.

Step 3

The morpholine cyclopropanol product of Step 2 was subjected to conditions similar to those described in Example 1, Steps 8 and 9, using 2-methyl-2-piperazin-1-yl-propan-1-ol instead of N-(2-hydroxyethyl)piperazine in the last step, to give the desired product, i.e., Example 35. $^1$H NMR (CDCl$_3$ 400 MHz) δ 7.71 (d, J=8.4 Hz, 2H), 7.46 (d, J=8.4 Hz, 2H), 4.56 (m, 1H), 3.60-3.75 (m, 3H), 3.30-3.50 (m, 4H), 2.85-3.00 (m, 2H), 2.45-2.85 (m, 5H), 1.60-1.85 (m, 3H), 1.38 (m, 1H), 0.90-1.25 (m, 3H), 1.05 (s, 6H), 0.88 (m, 1H), 0.55-0.70 (m, 2H), 0.30 (m, 1H); HRMS (MH$^+$)=542.2079.

The compounds in Table 6 were prepared following procedures similar to those of Example 35:

TABLE 6

| Example No. | COMPOUND | Mass Spec (M$^+$); retention time (min) |
|---|---|---|
| 36 | | 513.1; 3.85 |
| 37 | | 528.1; 2.95 |

TABLE 6-continued
| Example No. | COMPOUND | Mass Spec (M+); retention time (min) |
|---|---|---|
| 38 | 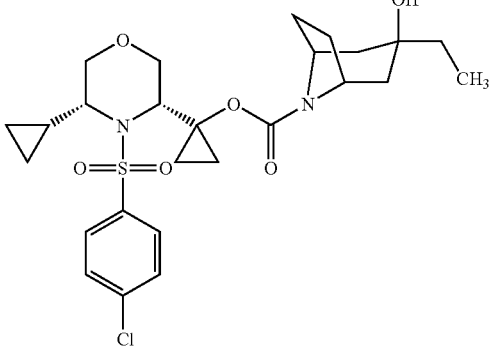 | 539.1; 3.88 |
| 39 | 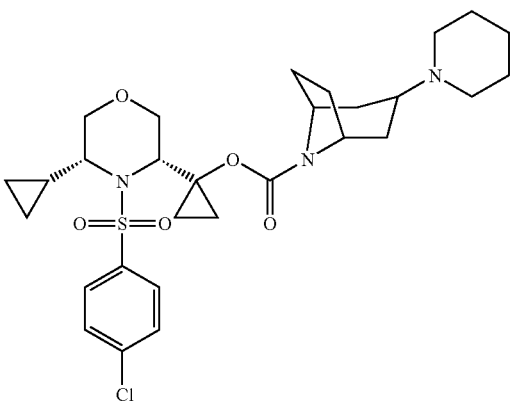 | 578.1; 3.43 |
| 40 | 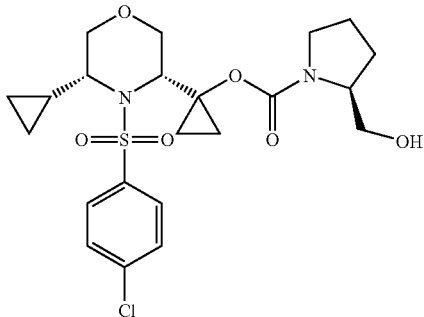 | 485.1; 3.64 |
| 41 | 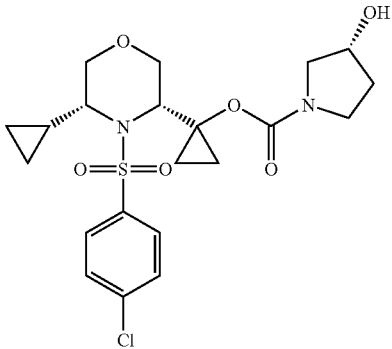 | 471.1; 3.36 |

TABLE 6-continued
| Example No. | COMPOUND | Mass Spec (M+); retention time (min) |
|---|---|---|
| 42 | 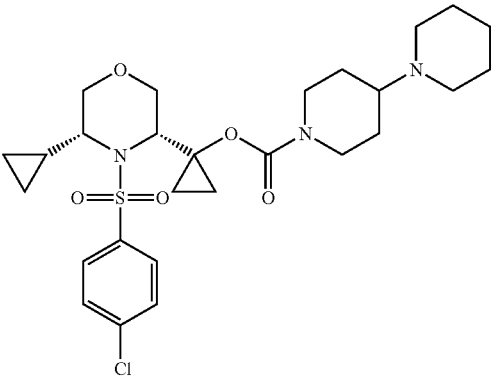 | 552.1; 3.30 |
| 43 | 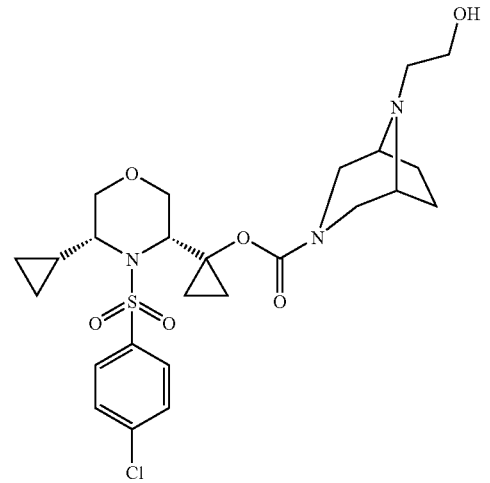 | 540.1; 2.97 |
| 44 | 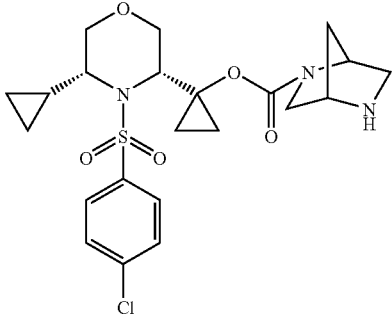 | 482.1; 2.89 |

TABLE 6-continued
| Example No. | COMPOUND | Mass Spec (M+); retention time (min) |
|---|---|---|
| 45 | 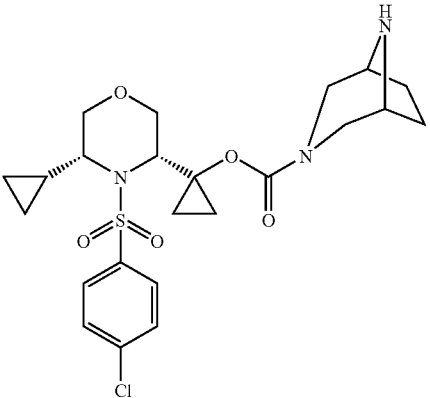 | 496.3; 2.95 |
| 46 | 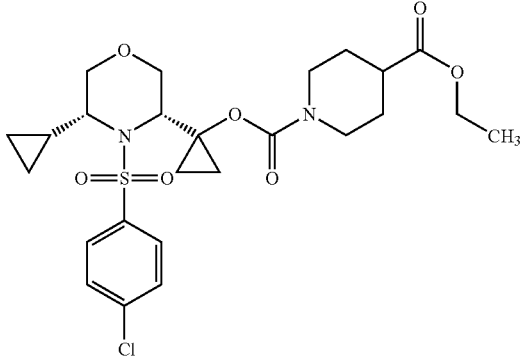 | 541.3; 4.77 |
| 47 | 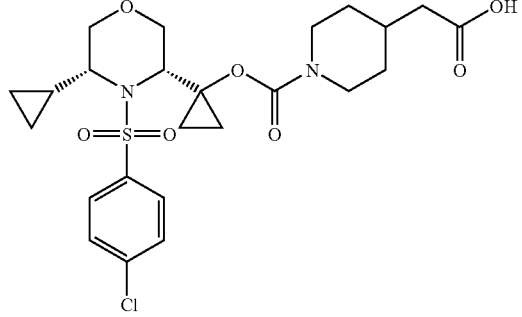 | 527.3; 3.89 |
| 48 | 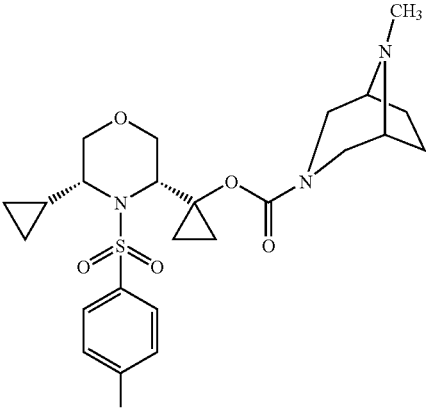 | 510.1; 3.21 |

TABLE 6-continued
| Example No. | COMPOUND | Mass Spec (M+); retention time (min) |
|---|---|---|
| 49 | 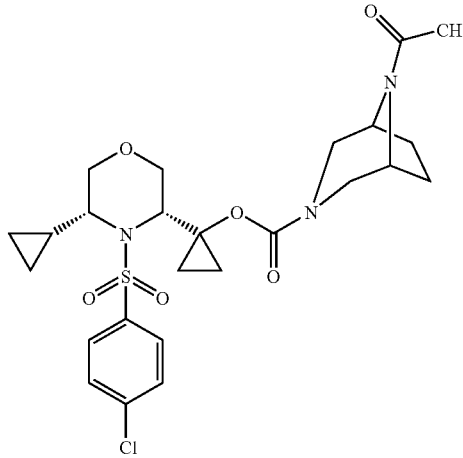 | 538.1; 3.91 |
| 50 | 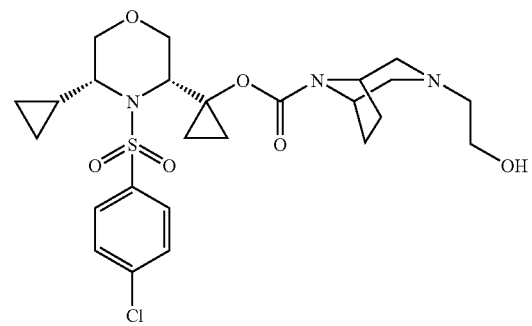 | 540.1; 3.10 |
| 51 | 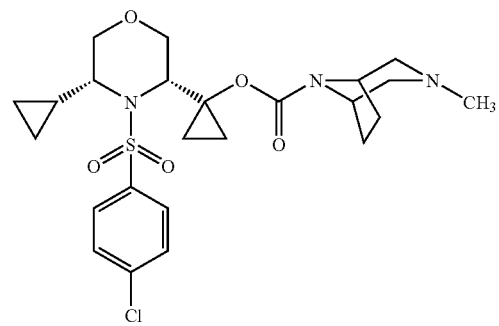 | 510.1; 3.15 |
| 52 | 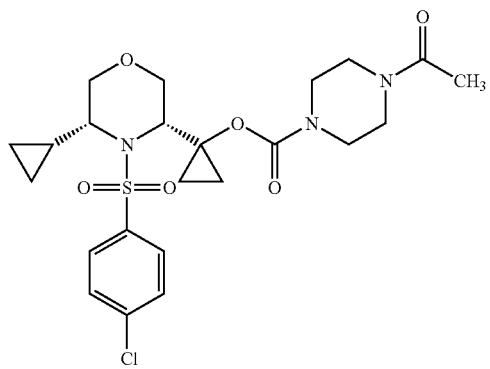 | 512.1; 3.84 |

TABLE 6-continued

| Example No. | COMPOUND | Mass Spec (M$^+$); retention time (min) |
|---|---|---|
| 53 | | 526.1; 2.99 |
| 54 | | 484.3; 3.28 |
| 55 | | 568.3; 3.42 |
| 56 | | 498.1; 3.81 |

TABLE 6-continued
| Example No. | COMPOUND | Mass Spec (M+); retention time (min) |
|---|---|---|
| 57 | 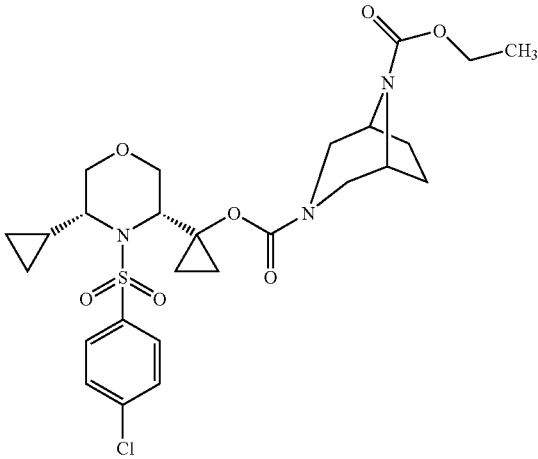 | 568.3; 4.69 |
| 58 | 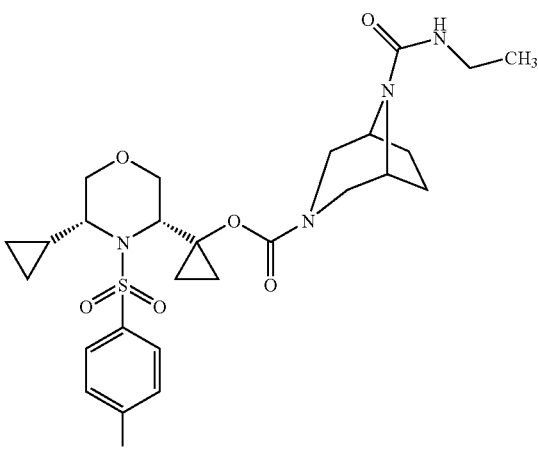 | 588.3; 4.41 |
| 59 | 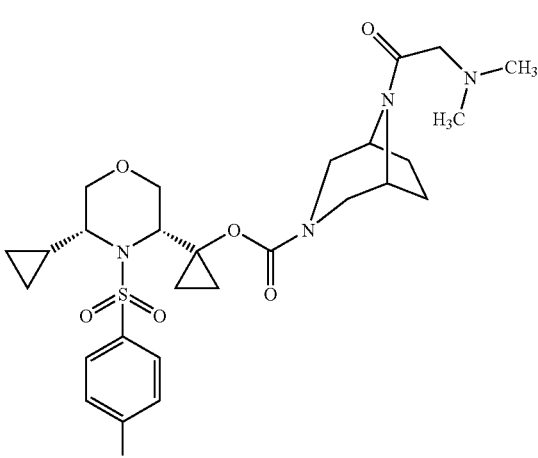 | 581.3; 3.06 |

TABLE 6-continued

| Example No. | COMPOUND | Mass Spec (M+); retention time (min) |
|---|---|---|
| 60 | | 496.3; 3.00 |
| 61 | | 588.3; 4.41 |
| 62 | | 564.3; 4.17 |

TABLE 6-continued

| Example No. | COMPOUND | Mass Spec (M+); retention time (min) |
| --- | --- | --- |
| 63 | | 538.1; 4.29 |
| 64 | | 581.3; 3.43 |
| 65 | | 524.3; 3.39 |
| 66 | | 560.3; 3.15 |

TABLE 6-continued
| Example No. | COMPOUND | Mass Spec (M+); retention time (min) |
|---|---|---|
| 67 | 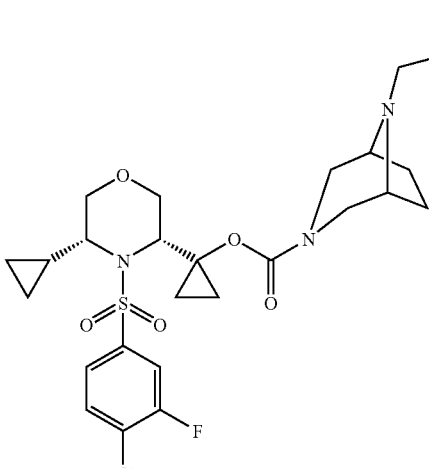 | 558.3; 3.09 |
| 68 | 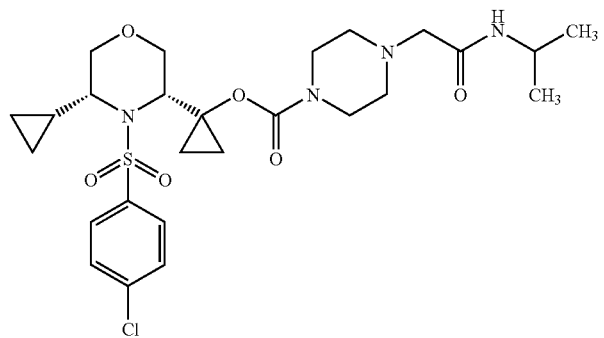 | 568.3; 4.20 |
| 69 | 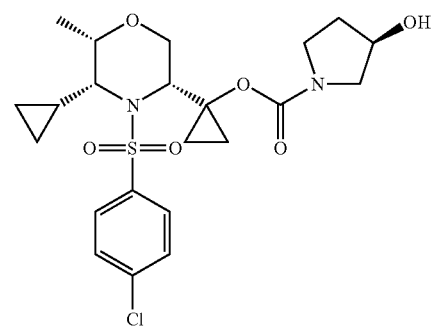 | 485.1; 4.13 |
| 70 | 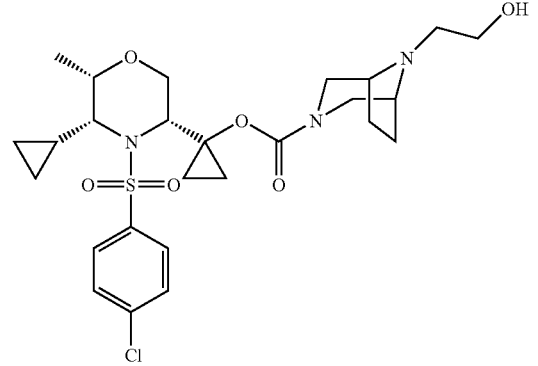 | 554.1; 3.01 |

TABLE 6-continued
| Example No. | COMPOUND | Mass Spec (M+); retention time (min) |
|---|---|---|
| 71 | 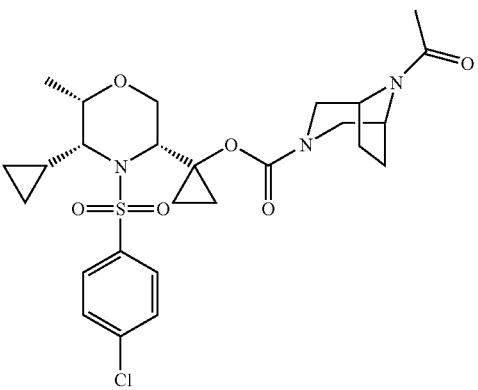 | 552.3; 4.01 |
| 72 | 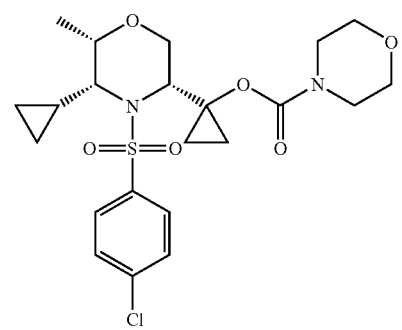 | 485.3; 4.57 |
| 73 | 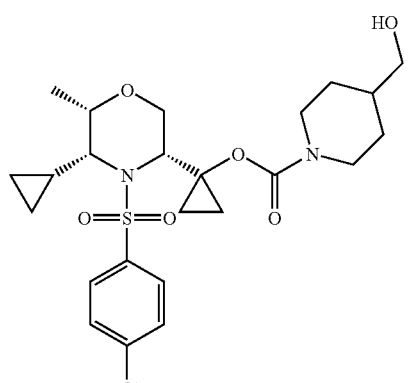 | 513.3; 4.35 |
| 74 | 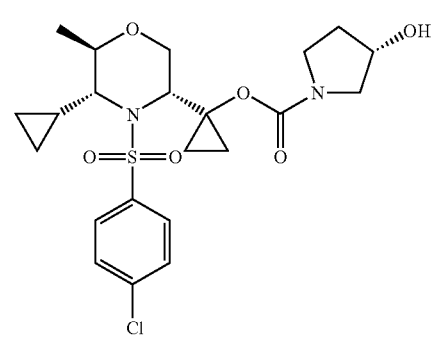 | 485.1; 4.02 |

TABLE 6-continued
| Example No. | COMPOUND | Mass Spec (M⁺); retention time (min) |
|---|---|---|
| 75 | 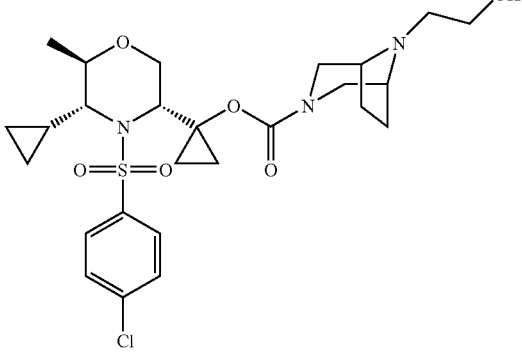 | 554.1; 2.95 |
| 76 | 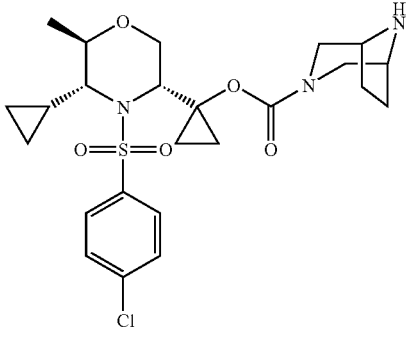 | 510.1; 3.17 |
| 77 | 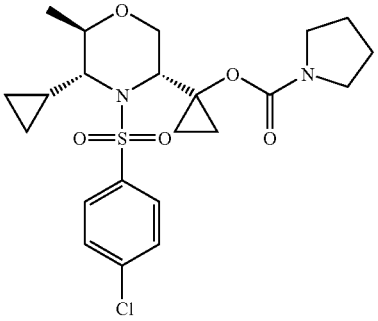 | 469.3; 4.94 |
| 78 | 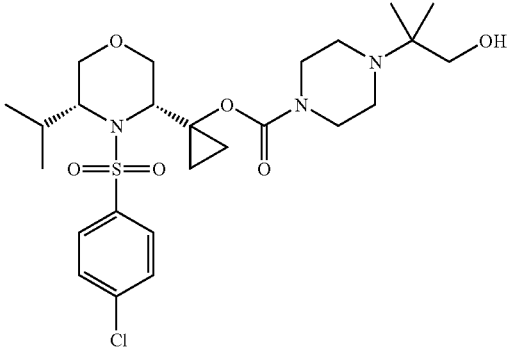 | 544.1; 2.93 |

TABLE 6-continued

| Example No. | COMPOUND | Mass Spec (M+); retention time (min) |
|---|---|---|
| 79 | | 501.3; 4.12 |
| 80 | | 473.3; 3.85 |

Example 81

3-Hydroxy-pyrrolidine-1-carboxylic acid 1-[4-(4-chloro-benzenesulfonyl)-5,6,6-trimethyl-morpholin-3-yl]-cyclopropyl ester

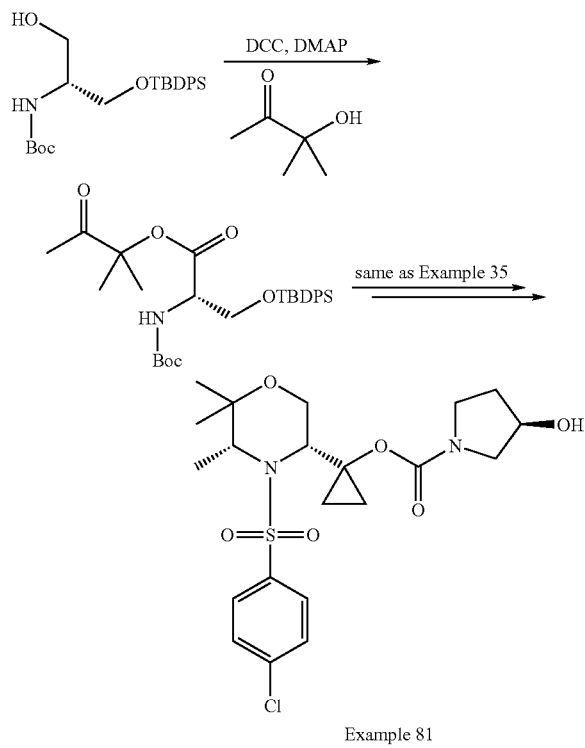

Example 81

Step 1

A solution of O-protected L-serine product of Example 29, Step 1 (37.8 g, 85.2 mmol), 3-hydroxy-3-methyl-2-butanone (9.05 mL, 86 mmol), DCC (17.8 g, 86 mmol) and DMAP (10.5 g, 86 mmol) in DCM (200 mL) was stirred at RT overnight. The reaction mixture was then diluted with water, extracted with DCM, dried and concentrated. The residue was filtered with a fritted disk and purified by flash-chromatography over silica gel (eluted with Hexanes/EtOAc 95:5 to 80:20) to give 29.95 g (67%) of ketone.

Step 2

The ketone product of Step 1 was subjected to conditions similar to those described in Example 29, Steps 3 to 7, and the resulting protected morpholine alcohol was subjected to conditions similar to those described in Example 35, Steps 1 to 3, using (R)-3-hydroxypyrrolidine in the last step, to give the desired product, i.e., Example 81. $^1$H NMR (CDCl$_3$ 400 MHz) δ 7.76 (d, J=8.4 Hz, 2H), 7.45 (d, J=8.4 Hz, 2H), 4.55-4.70 (m, 1H), 4.20-4.50 (m, 1H), 3.20-3.90 (m, 6H), 3.05-3.20 (m, 1H), 1.80-2.10 (m, 2H), 1.54 (d, J=7.2 Hz, 3H), 0.80-1.65 (m, 5H), 1.06 (br s, 3H), 0.56 (m, 3H); LCMS (MH$^+$)=473.3, purity >99%.

The compounds in Table 7 were prepared following procedures similar to those of Example 81:

TABLE 7

| Example No. | COMPOUND | Mass Spec (M+); retention time (min) |
|---|---|---|
| 82 | | 503.3; 3.58 |
| 83 | | 473.3; 4.50 |
| 84 | | 542.3; 3.29 |
| 85 | | 498.3; 3.38 |

TABLE 7-continued
| Example No. | COMPOUND | Mass Spec (M+); retention time (min) |
|---|---|---|
| 86 | 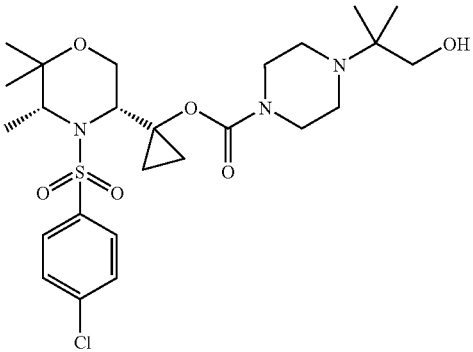 | 544.3; 3.38 |
| 87 | 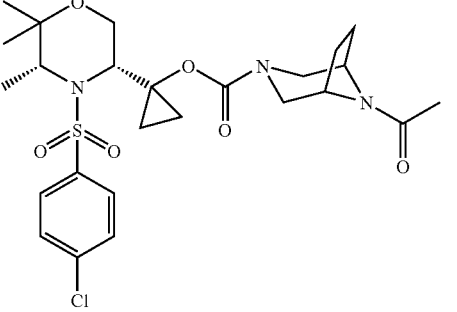 | 540.1; 4.02 |
| 88 | 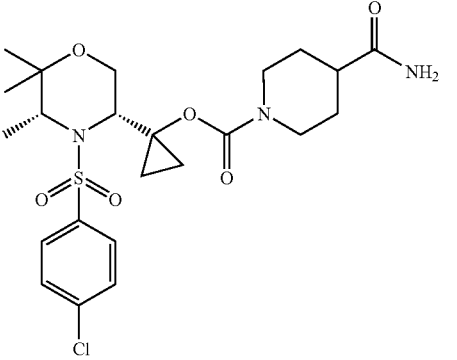 | 514.3; 3.59 |

Examples 89

3-Hydroxy-pyrrolidine-1-carboxylic acid 1-[4-(4-chloro-benzenesulfonyl)-5-ethyl-thiomorpholin-3-yl]-cyclopropyl ester and

Example 90

3-Hydroxy-pyrrolidine-1-carboxylic acid 1-[4-(4-chloro-benzenesulfonyl)-5-ethyl-1-oxo-1l4-thiomorpholin-3-yl]-cyclopropyl ester

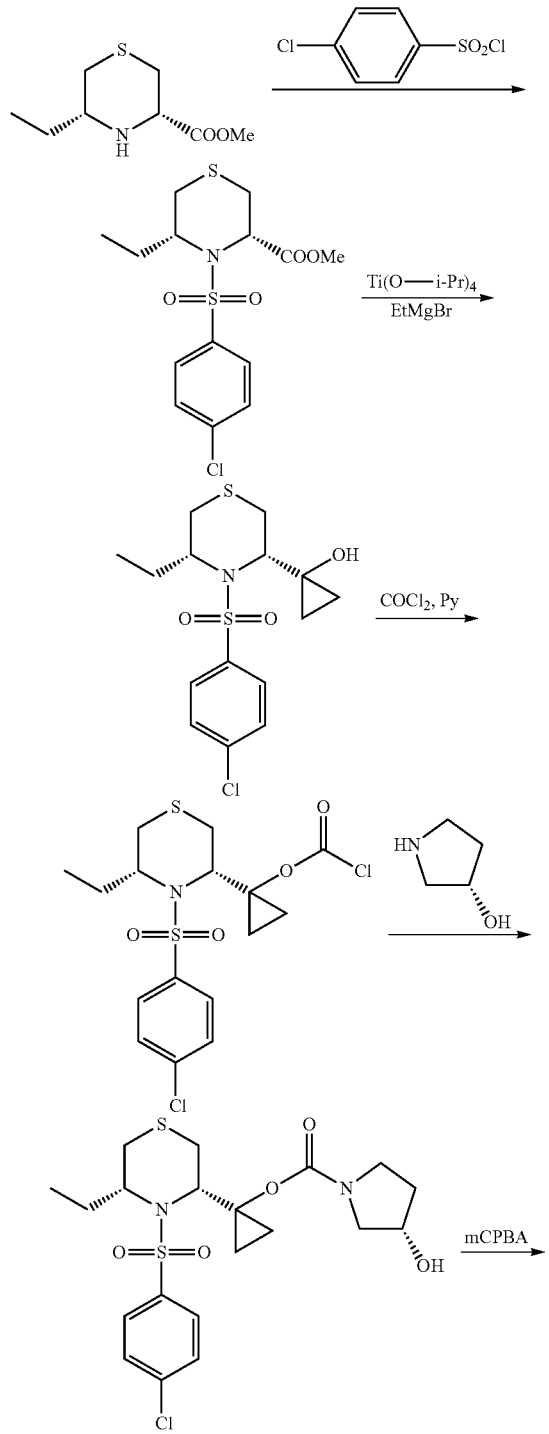

Example 89

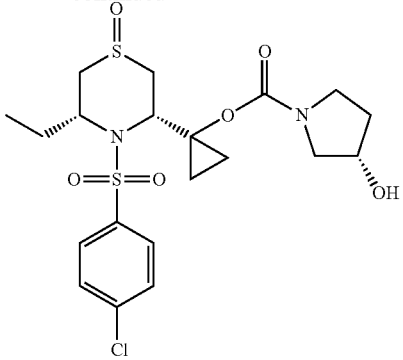

Example 90

5(R)-Ethyl-1,4-thiomopholinyl-3(S)-carboxylic acid methyl ester was synthesized according to Sakai's method (Kazuo Sakai and Naoto Yoneda, Chem. Pharm. Bull. 29 (1981), 1554; herein incorporated by reference in its entirety).

Step 1

5(R)-Ethyl-1,4-thiomopholinyl-3(S)-carboxylic acid methyl ester (2.6 g, 13.7 mmol), 4-chlorobenzenesulfonyl chloride (3.5 g, 16.5 mmol) and pyridine (100 mL) were heated to 80° C. overnight. Pyridine was removed and EtOAc (100 mL) was added. The organic layer was washed with saturated sodium carbonate solution (100 mL), 1N HCl solution (100 mL), brine (100 mL) and then dried over sodium sulfate. After the solvent was removed, the resulting residue was purified by flash-chromatography (eluted with hexanes/EtOAc 100:0 to 75:25). The product was further purified by recrystallization from a hexanes/EtOAc mixture to give 1.75 g (35%) of sulfonamide.

Step 2

The sulfonamide product of Step 1 (1.0 g, 2.75 mmol) and titanium(IV) isopropoxide (234 mg, 0.8 mmol) were dissolved in THF (30 mL), and the solution was cooled to 0° C. Ethyl magnesium bromide (3.0 M in ether, 2.8 mL, 8.3 mmol) was then added via a syringe pump over 30 minutes. After stirring for additional 30 minutes, the reaction mixture was quenched by adding EtOAc (50 mL), and then the mixture was poured into a saturated sodium bicarbonate solution (50 mL). The precipitate was filtered though a pad of Celite. The organic layer was washed with brine (50 mL) and dried over sodium sulfate. After the solvent was removed, the resulting residue was purified by flash-chromatography over silica gel (eluted with hexanes/EtOAc 100:0 to 75:25) to give 0.60 g (60%) of cyclopropanol.

Step 3

The cyclopropanol product of Step 2 (1.0 g, 2.75 mmol) and titanium (IV) (450 mg, 1.25 mmol) was dissolved in DCM (10 mL). Pyridine (4 mL) and 20% phosgene in toluene (3 mL) were added and the reaction mixture was stirred for an additional 3 h. DCM (50 mL) was added and the organic layer was washed with 1N hydrogen chloride solution (50 mL), and dried over sodium sulfate. After the solvent was removed, the resulting residue was purified by flash-chromatography over silica gel (eluted with hexanes/EtOAc 100:0 to 75:25) to give 0.20 g of carbonyl chloride product and 70 mg of unreacted starting material (cyclopropanol product of Step 2).

Step 4

The carbonyl chloride product of Step 3 (70 mg, 0.16 mmol) was dissolved in DCM (5 mL) and 3(S)-hydroxypyrrolidine (28 mg, 0.32 mmol) was then added. After stirring at room temperature for ten minutes, DCM (50 mL) was added and the organic layer was washed with brine (25 mL), dried over sodium sulfate and concentrated. The product, i.e., Example 89, was purified by flash-chromatography over silica gel (eluted with hexanes/EtOAc 100:0 to 50:50). $^1$H NMR (CDCl$_3$ 400 MHz) δ 7.74 (d, J=8.4 Hz, 2H), 7.47 (d, J=8.4 Hz, 2H), 4.8-4.9 (m, 1H), 4.3-4.5 (m, 1H), 3.9-4.05 (m, 1H), 3.2-3.8 (m, 4H), 1.7-2.5 (m, 8H), 1.0-1.2 (m, 7H). HRMS (MH$^+$)=475.1128.

Step 5

The product of Step 4 (34 mg, 0.072 mmol) was dissolved in DCM (5 mL), and mCPBA (77%, 16.1 mg, 0.72 mmol) was added. The mixture was stirred at room temperature for 10 minutes. DCM (40 mL) and 1N sodium hydroxide solution (40 mL) were then added. The organic and aqueous layers were separated, and the organic layer was dried over sodium sulfate and concentrated. The product, i.e., Example 90, was purified by flash-chromatography over silica gel (eluted with EtOAc). $^1$H NMR (CDCl$_3$ 400 MHz) δ 7.76 (dd, J=8.8 Hz and 2 Hz, 2H), 7.52 (dd, J=8.8 Hz and 2 Hz, 2H), 4.86 (dd, J=6.4 Hz and 5.2 Hz, 1H), 4.3-4.5 (m, 2H), 3.2-3.8 (m, 6H), 1.75-2.1 (m, 6H), 1.05-1.3 (m, 7H). LCMS (MH$^+$)=491.3, purity=99%.

The compounds in Table 8 were prepared following procedures similar to those of Examples 89 and 90:

TABLE 8

| Example No. | COMPOUND | Mass Spec (M$^+$); retention time (min) |
|---|---|---|
| 91 | 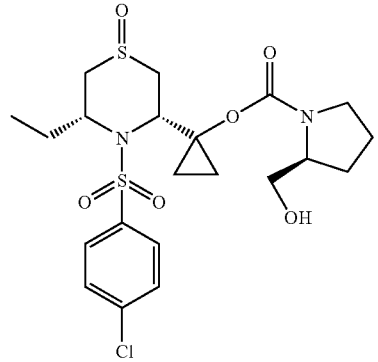 | 505.3; 3.21 |
| 92 | 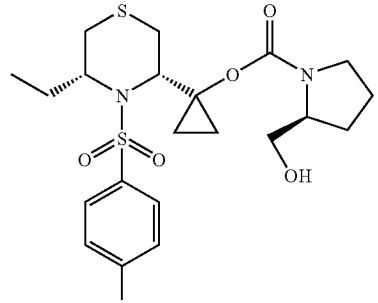 | 489.3; 4.28 |
| 93 | 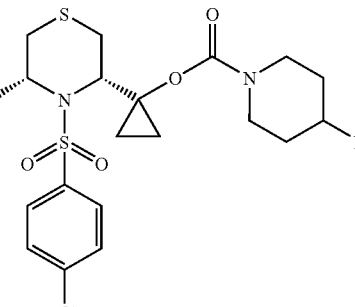 | 556.3; 3.58 |

Example 94

4-(2-Hydroxy-1,1-dimethyl-ethyl)-piperazine-1-carboxylic acid 1-[4-(4-chloro-benzenesulfonyl)-5-cyclopropylmethyl-morpholin-3-yl]-cyclopropyl ester

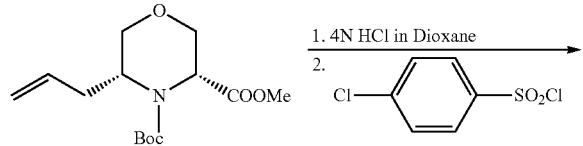

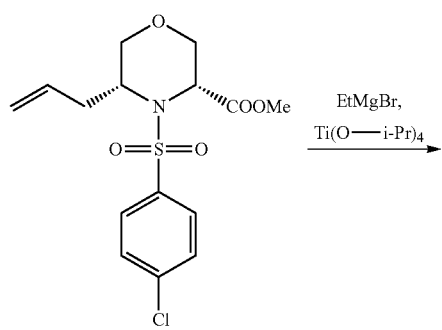

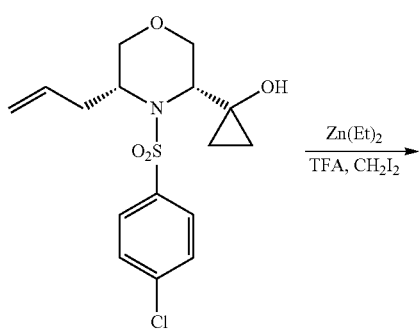

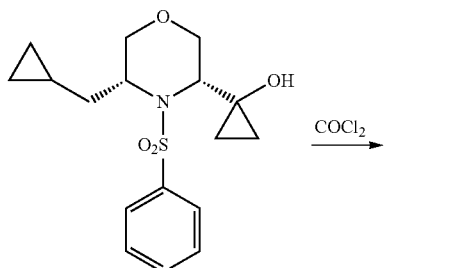

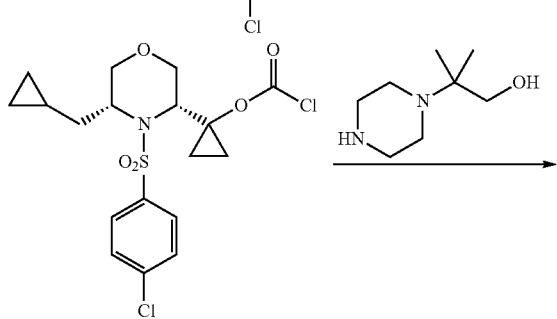

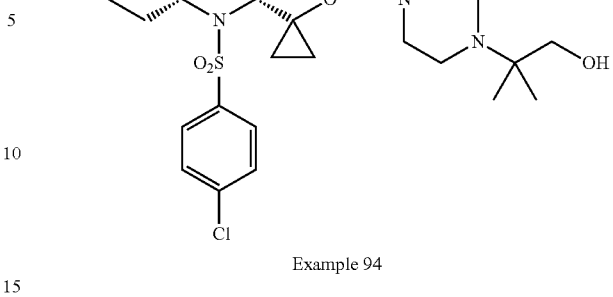

Example 94

Step 1

The product of Example 6, Step 2 (6.9 g, 24.2 mmol) and 4 N HCl in dioxane (50 mL) were stirred at room temperature for 1 hour. The solvent was removed and the residue was partitioned between EtOAc (200 mL) and saturated sodium carbonate solution (200 mL). The organic layer was washed with water (100 mL) and dried over sodium sulfate. The solvent was removed and the residue was dried under vacuum for 2 hours. 4-chlorobenzenesulfonyl chloride (7.6 g, 36.3 mmol) and pyridine (100 mL) were added and the reaction was heated to 80° C. overnight. The solvent was removed and the residue was partitioned between EtOAc (100 mL) and 1 N HCl aqueous solution (100 mL). The organic layer was washed with brine (100 mL), dried over sodium sulfate and concentrated. The product was purified by flash chromatography over silica gel (eluted with a gradient EtOAc/hexanes 0:100 to 25:75) to give 5.3 g (61%) of sulfonamide.

Step 2

Diethyl zinc 1 N in hexanes (44.2 mL, 44.2 mmol) was added to DCM (200 mL) at 0° C. TFA (5.0 g, 44.2 mmol) in DCM (20 mL) was added slowly in one minute and the reaction was stirred for 5 minutes. Diiodomethane (11.8 g, 44.2 mmol) in DCM (20 mL) was then added and the reaction was stirred for 5 more minutes. The sulfonamide product of Step 1 (5.3 g, 14.8 mmol) in DCM (50 mL) was then added and the reaction was slowly allowed to warm to RT overnight. Saturated ammonium chloride solution (100 mL) was added to quench the reaction and the organic layer was washed with brine (100 mL), dried over sodium sulfate and concentrated. The residue was purified by flash chromatography over silica gel (eluted with a gradient EtOAc/hexanes 0:100 to 25:75) to give 5.2 g (94%) of cyclopropylmethyl product.

Step 3

The cyclopropylmethyl product of Step 2 (4.5 g, 12 mmol) was subjected to conditions similar to those described in Example 35, Step 2 to give 2.7 g (60%) of cyclopropanol.

Step 4

The cyclopropanol product of Step 3 (2.7 g, 7.3 mmol) was dissolved in DCM (30 mL) and pyridine (2 mL) and phosgene (20% in toluene) were added and the reaction was stirred at room temperature for 10 minutes. DCM (20 mL) was added and the reaction was quenched by slowly adding water (10 mL). The reaction was further diluted with DCM (50 mL) and the organic layer was washed with 1 N aqueous HCl solution (50 mL) and dried over sodium sulfate. After evaporation of the solvent, the residue was purified by flash chromatography over silica gel (eluted with a gradient EtOAc/hexanes 0:100 to 25:75) to give 2.4 g (76%) of carbonyl chloride.

Step 5

The carbonyl chloride product from Step 4 (40 mg, 0.092 mmole) was dissolved in DCM (5 mL) and 4-(2-hydroxy-1, 1-dimethylethyl)-1-piperazine dihydrochloride (23 mg, 0.1 mmole) and a few drops of diisopropylethylamine were added. The mixture was stirred at room temperature for 30 minutes then diluted with DCM (40 mL) and saturated sodium carbonate solution (40 mL). The organic layer was separated, dried over sodium sulfate and concentrated. The product was purified by chromatography over silica gel (eluted with a gradient EtOAc/hexanes 50:50 to 100:0) to furnish the desired product, e.g. Example 94. $^1$H NMR (400 MHz, CDCl$_3$) δ 7.77 (d, J=8.06 Hz, 2H), 7.47 (d, J=8.06 Hz, 2H), 4.55 (d, J=4.39 Hz, 1H), 3.76 (d, J=11.7 Hz, 1H), 3.60 (m, 1H), 3.50 (m, 2H), 3.41 (d, J=12.4 Hz, 1H), 3.40 (m, 2H), 3.30 (s, 2H), 2.99 (dd, J=12.4, 4.4 Hz, 1H), 2.89 (dd, J=12.4, 4.4 Hz, 1H), 2.63 (m, 2H), 2.42 (m, 2H), 1.88 (m, 2H), 1.23 (m, 2H), 1.10 (m, 2H), 1.00 (s, 6H), 0.99 (m, 2H), 0.72 (m, 1H), 0.50 (m, 2H), 0.15 (m, 2H). HRMS (MH$^+$)=556.2250.

Following procedures similar to those of Examples 94, the compounds in Table 9 were prepared:

TABLE 9

| Example No. | COMPOUND | Mass Spec (M$^+$); retention time (min) |
|---|---|---|
| 95 | 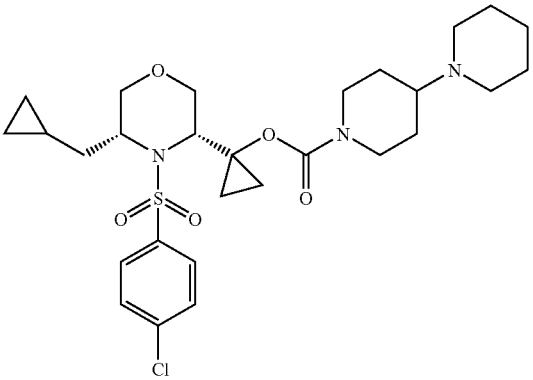 | 566.1; 3.51 |
| 96 (diastereoisomer 1) | 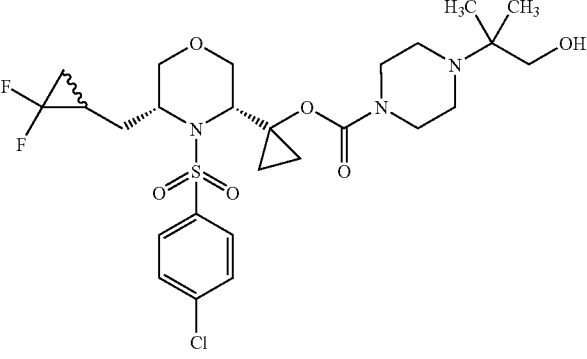 | 592.1; 3.26 |
| 97 (diastereoisomer 2) | 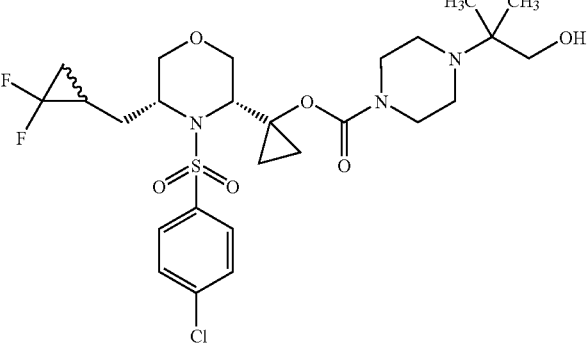 | 592.1; 3.25 |

TABLE 9-continued

| Example No. | COMPOUND | Mass Spec (M+); retention time (min) |
|---|---|---|
| 98 | | 540.1; 3.47 |
| 99 | | 554.1; 1.25 |
| 100 | | 556.1; 3.14 |
| 101 | | 538.1; 4.02 |

TABLE 9-continued

| Example No. | COMPOUND | Mass Spec (M⁺); retention time (min) |
|---|---|---|
| 102 | | 556.1; 3.40 |
| 103 | | 554.1; 3.36 |
| 104 | | 610.3; 5.33 |
| 105 | | 510.3; 3.22 |

TABLE 9-continued

| Example No. | COMPOUND | Mass Spec (M+); retention time (min) |
|---|---|---|
| 106 | | 552.1; 3.97 |
| 107 | | 581.1; 3.97 |
| 108 | | 485.3; 5.18 |
| 109 | | 485.3; 3.77 |

TABLE 9-continued

| Example No. | COMPOUND | Mass Spec (M+); retention time (min) |
|---|---|---|
| 110 | | 512.1; 4.15 |
| 111 | | 512.3; 3.33 |
| 112 | | 512.3; 3.38 |
| 113 | | 498.1; 3.07 |

TABLE 9-continued

| Example No. | COMPOUND | Mass Spec (M⁺); retention time (min) |
|---|---|---|
| 114 | | 570.1; 3.16 |
| 115 | | 568.1; 4.62 |
| 116 | | 604.1; 4.98 |
| 117 | | 513.3; 4.19 |

TABLE 9-continued

| Example No. | COMPOUND | Mass Spec (M+); retention time (min) |
|---|---|---|
| 118 | | 526.3; 3.78 |
| 119 | | 542.3; 3.21 |
| 120 | | 498.3; 3.25 |
| 121 | | 527.3; 4.34 |

TABLE 9-continued

| Example No. | COMPOUND | Mass Spec (M⁺); retention time (min) |
|---|---|---|
| 122 | | 512.3; 3.25 |
| 123 | | 516.1; 3.01 |
| 124 | | 560.3; 3.16 |
| 125 | | 562.3; 3.22 |

TABLE 9-continued

| Example No. | COMPOUND | Mass Spec (M⁺); retention time (min) |
|---|---|---|
| 126 | | 516.3; 3.56 |
| 127 | | 560.3; 3.59 |
| 128 | | 518.3; 4.24 |
| 129 | | 520.3; 3.65 |

TABLE 9-continued
| Example No. | COMPOUND | Mass Spec (M+); retention time (min) |
|---|---|---|
| 130 | 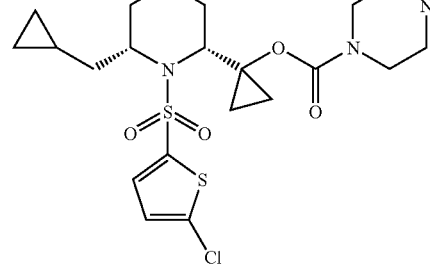 | 490.3; 3.23 |
| 131 | 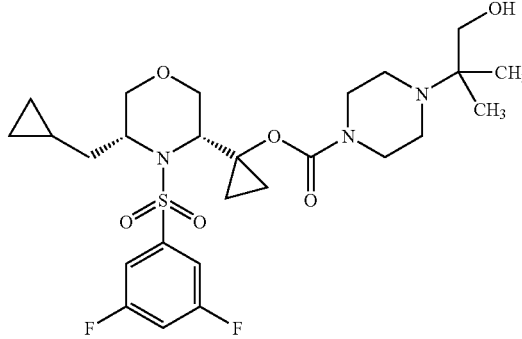 | 558.1; 3.30 |
| 132 | 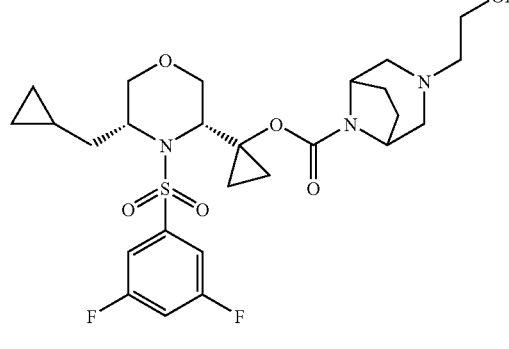 | 556.1; 3.24 |
| 133 | 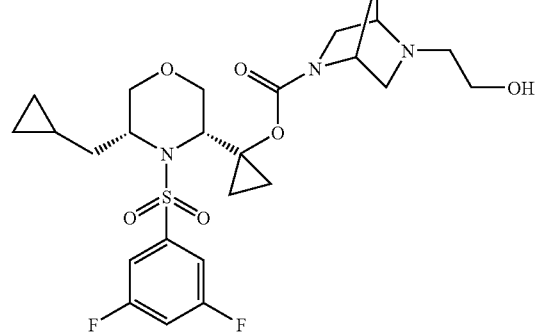 | 542.1; 3.13 |

TABLE 9-continued

| Example No. | COMPOUND | Mass Spec (M+); retention time (min) |
|---|---|---|
| 134 | | 555.1; 4.64 |
| 135 | | 512.1; 3.24 |
| 136 | | 514.1; 3.33 |
| 137 | | 556.3; 3.11 |

Example 138

[1,4']Bipiperidinyl-1'-carboxylic acid 1-(4-chloro-benzenesulfonyl)-6-(3,5-difluoro-phenyl)-4-ethyl-piperazin-2-yl methyl ester

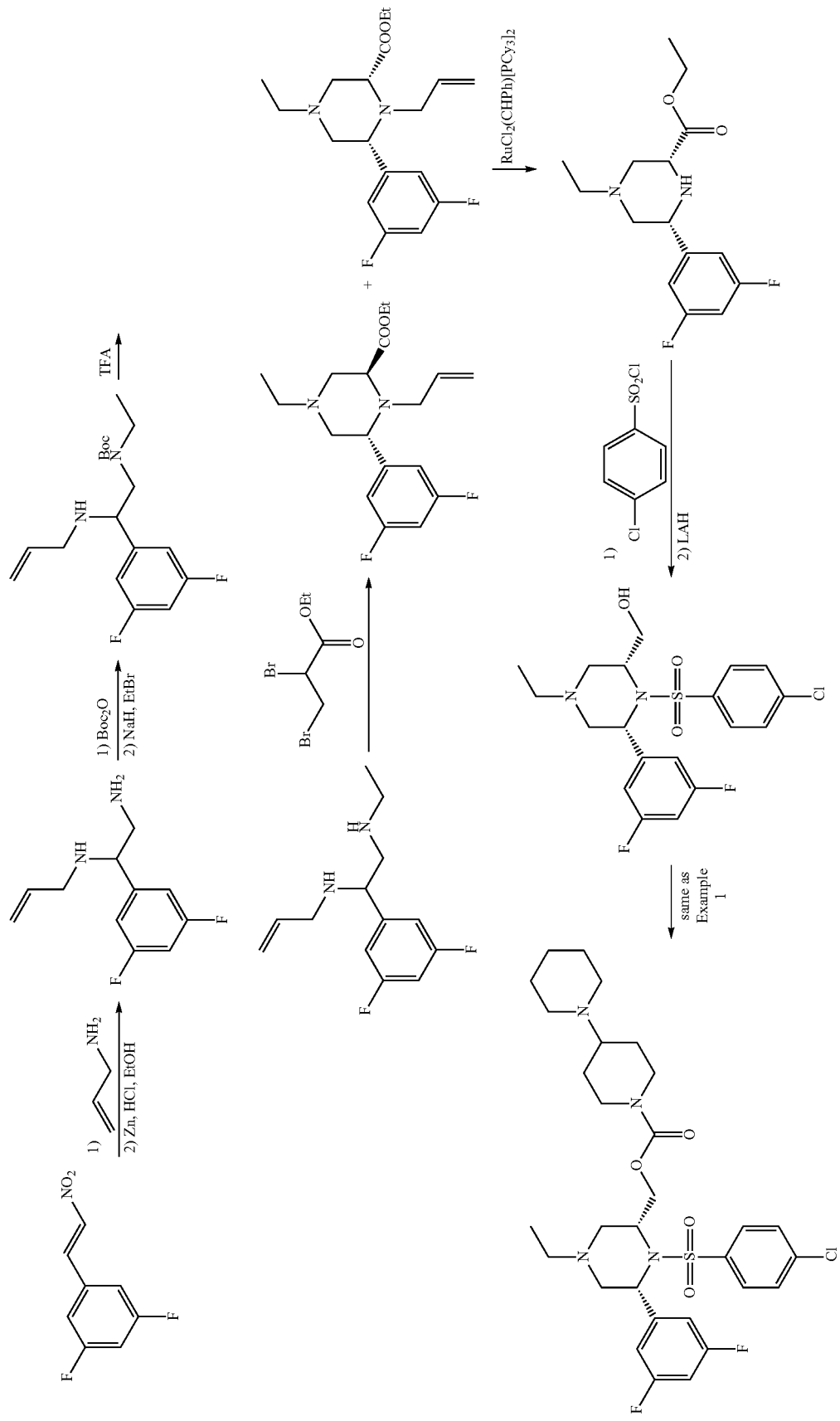

Step 1

A solution of 1,3-difluoro-5-(2-nitro-vinyl)-benzene (11.3 g, 61 mmol) in THF (100 mL) was treated with allylamine (18.3 mL, 240 mmol) at RT for 2 h. The reaction mixture was then concentrated, diluted with water and treated with an excess of concentrated HCl, then concentrated to yield 16.02 g (100%) of crude nitroamine hydrochloride.

Step 2

To a suspension of the nitroamine hydrochloride product of Step 1 (16.02 g, 61 mmol) in EtOH (120 mL) and concentrated HCl (120 mL) at 0° C. was slowly added zinc (20.0 g) and the reaction mixture was stirred 5 min at 0° C. then 2 h at RT. The reaction mixture was then filtered over Celite and concentrated. The residue was diluted with water, treated with an excess of concentrated ammonium hydroxide, extracted with DCM, dried over sodium sulfate and concentrated to give 11.08 g (86%) of diamine.

Step 3

To a solution of the diamine product of Step 2 (10.31 g, 48.6 mmol) in DCM (100 mL) was added di-tert-butyldicarbonate (11.2 g, 51 mmol) and the reaction was stirred at RT for 90 min then concentrated. The residue was purified by flash-chromatography over silica gel (eluted with hexanes/EtOAc 85:15 to 60:40) to afford 9.12 g (60%) of allyl mono-protected diamine.

Step 4

To a suspension of NaH (60% in hexanes, 1.28 g, 32 mmol) in DMF (30 mL) was added the allyl mono-protected diamine product of Step 3 (9.10 g, 29.1 mmol) in DMF (10 mL), and the reaction mixture was stirred 30 min at RT. Then bromoethane (2.45 mL, 33 mmol) was added and the mixture was stirred 30 min at RT and 2 h at 70° C. The final mixture was poured into EtOAc and water, extracted with EtOAc, washed with water, dried over sodium sulfate and concentrated. The residue was purified by flash-chromatography over silica gel (eluted with hexanes/EtOAc 90:10 to 70:30) to afford 7.31 g (74%) of allylethyl mono-protected diamine.

Step 5

A solution of the allylethyl mono-protected diamine product of Step 4 (7.31 g, 21.44 mmol) in DCM (20 mL) and TFA (10 mL) was stirred at RT for 2 h then concentrated. The resulting crude residue was treated with diluted NaOH, extracted with EtOAc, dried over sodium sulfate and concentrated to give 5.35 g (100%) of allylethyl diamine.

Step 6

To a solution of allylethyl diamine product of Step 5 (5.35 g, 21.44 mmol) and diisopropylethylamine (9.75 mL, 54 mmol) in DCE (25 mL) at 0° C. was slowly added ethyl-2,3-dibromopropionate (3.44 mL, 23.6 mmol) in DCE (25 mL), and the reaction was stirred at RT overnight. After workup, the residue was purified by flash-chromatography over silica gel (eluted with hexanes/ether 90:10 to 10:90) to provide, in order of elution, 2.68 g (37%) of trans-allylpiperazine ester and 1.69 g (23%) of cis-allylpiperazine ester.

Step 7

A solution of the cis-allylpiperazine ester product of Step 6 (1.80 g, 5.32 mmol) and chlorotris(triphenylphosphine) rhodium(I) (700 mg) in EtOH (20 mL) and water (2 mL) was stirred at 100° C. for 3 days. After filtration and concentration, the residue was purified by flash-chromatography over silica gel (eluted with hexanes/EtOAc 85:15 to 40:60) to provide 1.29 g (75%) of cis-piperazine ester.

Step 8

A solution of cis-piperazine ester product of Step 7 (1.28 g, 4.29 mmol), 4-chlorobenzenesulfonyl chloride (1.10 g, 5.2 mmol) and pyridine (865 µL, 10.7 mmol) in DCE (15 mL) was heated at 40° C. for 6 h then cooled down. The mixture was poured into saturated sodium bicarbonate solution, extracted with DCM and EtOAc, dried over sodium sulfate and concentrated. The residue was purified by flash-chromatography over silica gel (eluted with DCM/hexanes 50:50 to DCM) to give 674 mg (33%) of cis-piperazinesulfonamide ester.

Step 9

A solution of the cis-piperazinesulfonamide ester product of Step 8 (307 mg, 0.65 mmol) in THF (3 mL) at 0° C. was treated with LAH (1N in THF, 0.65 mL, 0.65 mmol), and the reaction mixture was allowed to warm to RT for 30 min. It was then quenched with EtOAc, diluted with water, filtered over Celite, and extracted with EtOAc, dried over sodium sulfate and concentrated. The residue was purified by flash-chromatography over silica gel (eluted with DCM to DCM/EtOAc 1:1) to afford 257.7 mg (92%) of cis-piperazinesulfonamide alcohol.

Step 10

The cis-piperazinesulfonamide alcohol product of Step 9 was subjected to conditions similar to those described in Example 1, Step 8 and Step 9, using 4-(N-piperidino)piperidine instead of N-(2-hydroxyethyl)piperazine in the last step, to afford the desired product, e.g. Example 138. $^1$H NMR (CDCl$_3$ 400 MHz) δ 7.80 (d, J=8.7 Hz, 2H), 7.52 (d, J=8.7 Hz, 2H), 7.22 (m, 2H), 6.72 (m, 1H), 4.99 (br s, 1H), 4.10-4.35 (m, 3H), 3.88 (m, 1H), 3.57 (t, 1H), 3.30 (d, 1H), 2.40-2.90 (m, 8H), 2.20-2.35 (m, 2H), 1.40-1.95 (m, 10H) 1.20-1.35 (m, 2H), 1.06 (t, J=7.2 Hz, 3H). LCMS (MH$^+$)=625.1, purity >99%.

Example 139

4-[[1-[cis-4-[(4-chlorophenyl)sulfonyl]-5-cyclopropyl-3-morpholinyl]cyclopropyl]acetyl]-beta,beta-dimethyl-1-piperazineethanol

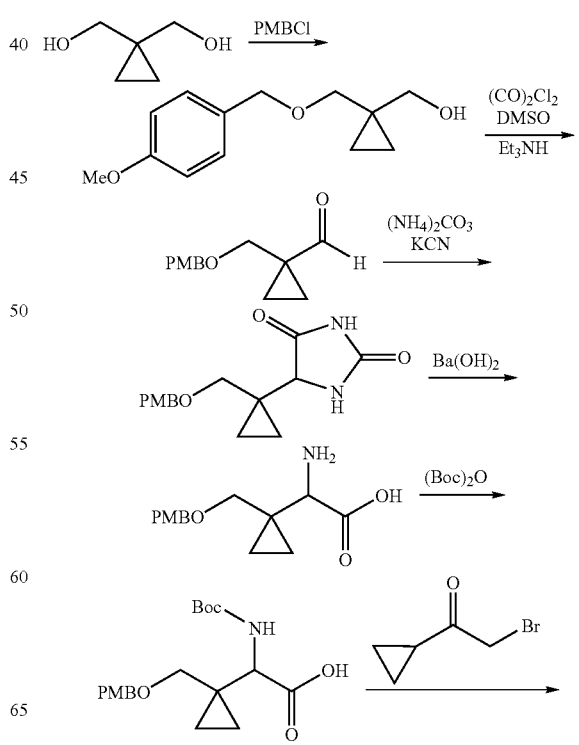

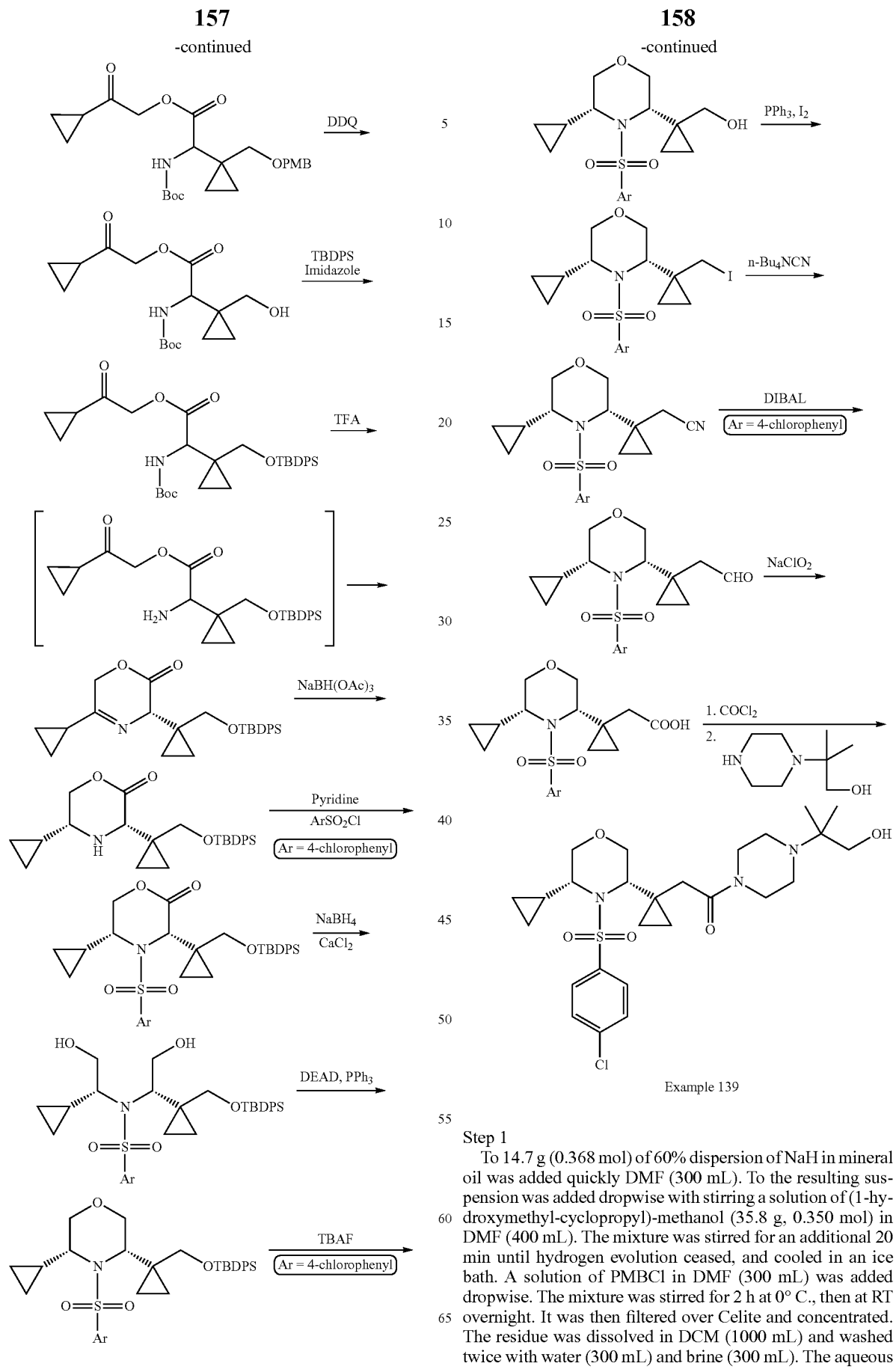

Example 139

Step 1

To 14.7 g (0.368 mol) of 60% dispersion of NaH in mineral oil was added quickly DMF (300 mL). To the resulting suspension was added dropwise with stirring a solution of (1-hydroxymethyl-cyclopropyl)-methanol (35.8 g, 0.350 mol) in DMF (400 mL). The mixture was stirred for an additional 20 min until hydrogen evolution ceased, and cooled in an ice bath. A solution of PMBCl in DMF (300 mL) was added dropwise. The mixture was stirred for 2 h at 0° C., then at RT overnight. It was then filtered over Celite and concentrated. The residue was dissolved in DCM (1000 mL) and washed twice with water (300 mL) and brine (300 mL). The aqueous washes were then extracted twice with DCM. Combined organic phases were dried over sodium sulfate and concentrated. The product was isolated by flash-chromatography over silica gel, eluted with 10-30% EtOAc/hexanes first to elute the bis-alkylated by-product of the reaction, and then 43.96 g of the desired monoprotected alcohol.

Step 2

To a solution of 23.3 mL of oxalyl chloride in DCM (750 mL) cooled to −65° C. to −70° C. was added a solution of DMSO (23.6 mL) in DCM (106 mL) dropwise. The reaction mixture was stirred for an additional 1 hr prior to the addition of a solution of the mono-protected alcohol product from Step 1 (29.6 g) in DCM (372 mL), maintaining the internal temperature below −60° C. The mixture was stirred 20 more min followed by the rapid addition of triethylamine (186 mL) while maintaining the internal temperature between −55 and −60° C. The reaction was allowed to warm to 0° C. over 1 h then worked up and purified by flash-chromatography over silica gel, eluted using a mixture of 20% EtOAc in hexanes to give 23.65 g of aldehyde.

Step 3

A mixture of the aldehyde product of Step 2 (18.2 g, 0.083 mol), potassium cyanide (8.1 g, 0.124 mol), ammonium carbonate (23.9 g, 0.249 mol), triethylamine (50 mL) and 50% aqueous ethanol (100 mL) was placed in a 350 mL glass pressure vessel. After 2 min of ultrasonication, the mixture was stirred at 60° C. overnight, followed by cooling and DCM/water workup. A second reaction batch starting from freshly prepared aldehyde product of Step 2 was processed similarly. The crude product of the two combined batches was recrystallized from solvent containing MeOH, DCM and hexanes to furnish 32.99 g of hydantoin.

Step 4

A mixture of hydantoin product of Step 3 (21.4 g, 73.7 mmol), barium hydroxide (20.82 g, 147.4 mmol) and 275 mL of water was refluxed overnight. The resulting precipitate was filtered out through glass filter while the mixture was hot. The filtrate was allowed to cool to 60° C. and treated with ammonium carbonate (16.4 g, 171 mmol). The mixture was boiled for 1 h and the formed precipitate of barium hydroxide was filtered out through glass filter while the mixture was hot. The filtrate was boiled for 1 hr in an open flask in fume hood to destroy the excess of ammonium carbonate, while the volume of solution was maintained at 300 mL by adding water to account for evaporation. The desired product precipitated upon cooling the mixture to 5° C. and was collected by filtration to afford 11.6 g of amino acid.

Step 5

To a suspension of amino acid from Step 4 (26.3 g, 99.2 mmol) in a mixture of dioxane (80 mL) and water (80 mL) was added Boc$_2$O (38.98 g, 179 mmol) and triethylamine (27.9 mL). After overnight stirring, the volatiles were evaporated, the resulting residue was dissolved in DCM, washed with 20% citric acid, and the aqueous phase was back-extracted with DCM. The organic phase was dried over sodium sulfate and concentrated. The residue was purified by flash-chromatography over silica gel, eluted with hexanes to 20% EtOAc/hexanes to elute non-polar admixtures, and then 5-10% MeOH/DCM to elute the desired Boc-protected amino acid.

Step 6

To a mixture of Boc-protected amino acid from Step 5 (113.5 g, 0.391 mol) in DCM (250 mL) and MeOH (750 mL) at 0° C. was added a solution of KOH (22.0 g, 0.39 mol) in MeOH (500 mL). After concentration of the solvents, the residue was dissolved in DMF (250 mL) and was added with ice cooling a mixture of 2-bromo-1-cyclopropyl-ethanone (63.8 g, 0.391 mol) in DMF (150 mL). The mixture was stirred at RT overnight. After standard aqueous workup (DCM/water) the product was isolated by flash-chromatography over silica gel, eluted with 30% ethyl acetate/hexanes, to furnish 114.7 g of ester.

Step 7

To a mixture of ester product from Step 6 (15.2 g, 33.96 mmol) in DCM (240 mL) and water (4.8 mL) was added DDQ (8.4 g, 37.0 mmol). The reaction was stirred overnight, solids were filtered out, and the solution was concentrated. Two more batches were prepared in a similar manner, each containing 50 g of ester product from Step 6. The crude products were combined and purified by flash-chromatography over silica gel, eluted with 0-30% gradient of EtOAc/hexanes, followed by 40% EtOAc/hexanes, and the final product was recrystallized in DCM, EtOAc and hexanes to give 61.88 g of alcohol.

Step 8

To a solution of alcohol product from Step 7 (61.88 g, 189 mmol) in THF (500 mL) was added imidazole (25.75 g, 378 mmol) followed by TBDPSCl (62.38 g, 227 mmol) in THF (100 mL). The reaction was stirred at RT overnight, the solids were filtered out using Celite and the filtrate was concentrated. The residue was partitioned between EtOAc and water. The aqueous phase was extracted with EtOAc. The combined organic phases were dried over sodium sulfate and concentrated. The residue was recrystallized from EtOAc and hexanes to furnish 83 g of protected alcohol. An additional 12.5 g of protected alcohol was isolated from mother liquor by flash-chromatography over silica gel.

Step 9

To a mixture of protected alcohol from Step 8 (30 g, 53 mmol) in 300 mL of DCM was added TFA (90 mL). After 1 h of stirring the volatiles were evaporated. The product was re-dissolved in 300 mL of DCM, shaken with 250 mL of saturated sodium bicarbonate, and further extracted with DCM. The combined organic phases were dried over sodium sulfate. The solvent was evaporated, the resulting residue co-evaporated 2 times with EtOAc, and was kept on rotovapor on a hot bath (60° C.) for 20 min. The product was recrystallized from EtOAc/hexanes to furnish 17.0 g of imine. Additionally, 4.41 g of imine was isolated from mother liquor by flash-chromatography over silica gel.

Step 10

To a mixture of imine product of Step 9 (4.41 g, 9.86 mmol) and NaHB(OAc)$_3$ (2.19 g, 10.35 mmol) in 50 mL of DCM at 0° C. was slowly added TMSCl (1.37 mL, 10.84 mmol). The mixture was stirred overnight, worked up using saturated sodium bicarbonate and DCM, and the resulting amine (2.90 g) was isolated by flash-chromatography over silica gel (eluted with 20% EtOAc/hexanes).

Step 11

A mixture of amine product from Step 10 (12.3 g, 27.4 mmol) and 4-chlorobenzenesulfonylchloride (28.9 g, 137 mmol) in 230 mL of pyridine was heated at 85° C. overnight in a pressure vessel. Concentration of the solvents followed by flash-chromatography over silica gel (eluted with a gradient from 0 to 30% EtOAc in hexanes) furnished 9.01 g of sulfonamide.

Step 12

To a mixture of sulfonamide product from Step 11 (8.82 g, 14.15 mmol), calcium chloride (9.4 g, 84.9 mmol), 70 mL of THF and 105 mL of ethanol was added in portions sodium borohydride (2.67 g, 70.76 mmol). The reaction was stirred overnight, quenched with 20% aq. citric acid, extracted with DCM, dried (MgSO$_4$) and concentrated. The product was purified by flash-chromatography over silica gel (eluted with a gradient 0 to 30% of EtOAc in hexanes) to furnish 8.2 g of diol.

Step 13

A mixture of diol product from Step 12 (8.2 g, 13.1 mmol), triphenylphosphine (10.3 g, 39.3 mmol) and 1.5 g of molecular sieves (4A) in toluene (120 mL) was stirred for a few minutes prior to slow addition of DEAD. The reaction was stirred at RT overnight. The desired morpholine product (5.44 g) was isolated after flash chromatography over silica gel (eluted with a gradient 0-20% EtOAc/Hexanes).

Step 14

To a mixture of morpholine product from Step 13 (5.44 g, 8.93 mmol) in 75 mL of THF was added 1 N TBAF solution in THF (17.86 mL, 17.86 mmol). The mixture was stirred overnight, quenched with water and extracted with ethyl acetate. The organic phase was washed with brine, dried over $MgSO_4$ and concentrated. The desired morpholine alcohol (3.4 g) was isolated after flash-chromatography over silica gel (eluted with a gradient 0-30% EtOAc/hexanes).

Step 15

To a mixture of morpholine alcohol product from Step 14 (478 mg, 1.29 mmol) in 4.0 mL acetonitrile and 8.0 mL of toluene was added triphenylphosphine (406 mg, 1.55 mmol), iodine (393 mg, 1.55 mmol) and imidazole (263.5, 3.87 mmol). The reaction was stirred at RT for 1 h, quenched with 20% aq. ammonium chloride, extracted twice with diethyl ether. The organic phase was washed with saturated sodium bicarbonate, brine, dried over magnesium sulfate and concentrated. The residue was purified by flash-chromatography over silica gel (eluted with a gradient 0 to 80% DCM/hexanes) to furnish 550 mg of iodide.

Step 16

A suspension of the iodide product from Step 15 (550 mg, 1.14 mmol) and tetrabutylammonium cyanide (371 mg (1.38 mmol) in 10 mL of acetonitrile was stirred for 1.5 h. Water was added to the reaction mixture and it was extracted twice with EtOAc. The organic phase was washed with brine, dried over magnesium sulfate and concentrated. The product was purified by flash-chromatography over silica gel (eluted with a gradient from 0 to 30% EtOAc/hexanes) to furnish 393 mg of nitrile.

Step 17

A solution of nitrile product from Step 16 (393 mg, 1.03 mmol) in DCM (7.0 mL) was treated at −78° C. with a 1 M solution of DIBAL in DCM (1.55 mL). The reaction was stirred at −78° C. for 4 h, quenched with methanol (2.0 mL). After stirring for 10 minutes, 1 M sulfuric acid (2.0 mL) was added, and stirring was continued for 45 min. The product was extracted twice with DCM, washed with water and brine. The organic phase was dried over magnesium sulfate, and concentrated. The product was purified by flash-chromatography over silica gel (eluted with a gradient from 0 to 30% ethyl acetate/hexanes) to furnish 393 mg of aldehyde.

Step 18

To a mixture of aldehyde product from Step 17 (325 mg, 0.85 mmol) in tert-butanol (12.0 mL) and water (3.0 mL), were added 2-methyl-2-butene (0.361 mL, 3.4 mmol) and sodium chlorite (246 mg, 2.72 mmol). The reaction was stirred at RT for 2 h, then quenched with saturated ammonium chloride and extracted with EtOAc. The organic phase was washed with brine, dried over magnesium sulfate, and concentrated to furnish 390 mg of crude carboxylic acid which was used in the next step without further purification.

Step 19

To the carboxylic acid product from Step 18 (60 mg, 0.15 mmol) in 2.0 mL of DCM was added oxalyl chloride (0.105 mL, 1.2 mmol). The mixture was stirred for 20 min. The solvent was removed in vacuum. The residue was transferred to a vial containing 70 mg (0.30 mmol) of hydrochloride salt of 2-methyl-2-piperazin-1-yl-propan-1-ol and triethylamine (0.126 mL) in 1.0 mL of DCM. The mixture was stirred overnight, diluted with DCM, washed with saturated sodium bicarbonate, water and brine. The organic phase was dried over magnesium sulfate, concentrated, and the product was purified by prep. silica gel TLC plate using 7% MeOH/DCM as solvent to furnish 62 mg of Example 139. $^1$H NMR (CDCl$_3$, 400 MHz) δ 7.70 (d, J=8.8 Hz, 2H), 7.46 (d, J=8.8 Hz, 2H), 4.31 (m, 1H), 3.74-3.30 (ser m, 9H), 2.91 (m, 1H), 2.81-2.45 (ser m, 6H), 2.20 (br, 1H), 1.78 (m, 1H), 1.70 (m, 1H), 1.28 (m, 1H), 1.03 (s, 3H), 1.02 (s, 3H), 0.85-0.61 (ser m, 5H), 0.48 (m, 1H), 0.28 (m, 1H); LCMS (M+H$^+$) m/z=540.3, retention time 2.91 min.

The compounds in Table 9 were prepared following procedures similar to those used to prepare Example 139:

TABLE 10

| Example No. | COMPOUND | Mass Spec (M$^+$); retention time (min) |
|---|---|---|
| 140 | [structure] | 538.1; 2.91 |

TABLE 10-continued

| Example No. | COMPOUND | Mass Spec (M$^+$); retention time (min) |
| --- | --- | --- |
| 141 (diastereoisomer 1) | | 576.1; 3.35 |
| 142 (diastereoisomer 2) | | 576.1; 3.31 |
| 143 | | 494.3; 2.89 |
| 144 | | 556.3; 3.89 |

TABLE 10-continued
| Example No. | COMPOUND | Mass Spec (M+); retention time (min) |
| --- | --- | --- |
| 145 | | 536.3; 3.68 |
Example 146
alpha-[1-[4-[(4-chlorophenyl)sulfonyl]-5(r)-cyclopropyl-3(s)-morpholinyl]cyclopropyl]-beta-oxo-3,8-diazabicyclo[3.2.1]octane-3-ethanol
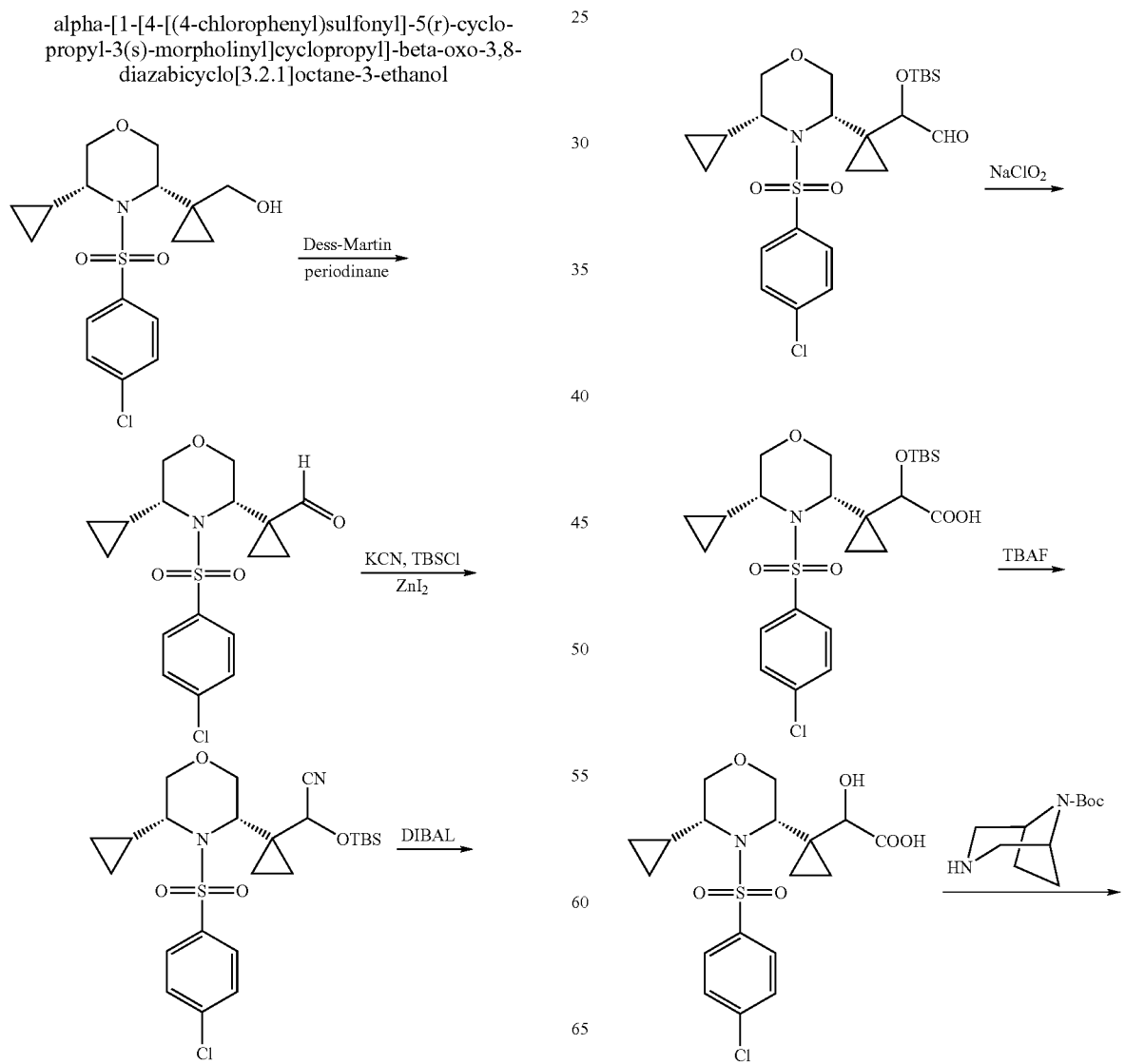

-continued

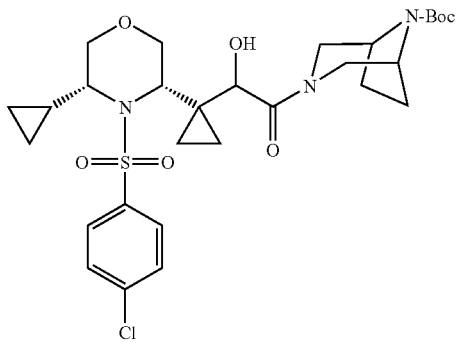

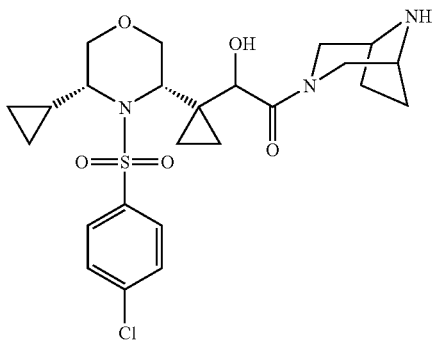

Example 146

Step 1

To a solution of the morpholine alcohol product from Example 139, Step 14 in DCM (12 mL) was added Dess-Martin periodinane (633 mg, 1.49 mmol) as a solid. After 1 h of stirring, the mixture was quenched with 15 mL of saturated sodium bicarbonate and 600 mg of solid $Na_2S_2O_3$. The mixture was stirred until a clear liquid-liquid biphasic mixture was obtained (1 hr). The organic layer was separated and the aqueous phase was extracted with DCM. The combined organic phases were dried over sodium sulfate and concentrated to furnish 435 mg of crude aldehyde, used in the next step without purification.

Step 2

A mixture of aldehyde product from Step 1 (800 mg, 2.16 mmol), potassium cyanide (843 mg, 12.98 mmol), TBSCl (488 mg, 3.24 mmol) and zinc iodide (34.5 mg, 0.108 mmol) in acetonitrile (15 mL) was heated at 55° C. overnight. An additional portion of above mentioned amounts of potassium cyanide, TBSCl and 200 mg (0.627 mmol) of zinc iodide was added and the reaction was heated at 55° C. for another 48 h. After standard aqueous workup (DCM/water), the residue was purified by flash-chromatography over silica gel (eluted with a gradient 0-30% ethyl acetate in hexanes) to give 393 mg of protected cyanohydrin.

Step 3

A solution of the cyanohydrin product from Step 2 (393 mg, 0.76 mmol) in DCM (10 mL) at −78° C. was treated with a 1 N solution of DIBAL in hexanes (1.38 mL, 1.38 mmol). After stirring at this temperature for 4 h, the reaction was quenched with 40 mL of tartrate buffer. The mixture was diluted with 50 mL of DCM and stirred at RT for 1 h to hydrolyze the intermediate imine. The aldehyde (140 mg) was isolated upon DCM extraction and flash-chromatography over silica gel (eluted with a gradient 0-30% EtOAc/hexanes).

Step 4

To a mixture of aldehyde product from Step 3 (140 mg, 0.272 mmol) in tert-butanol (2.0 mL) and water (0.4 mL) was added a 2 N solution of 2-methyl-2-butene in THF (0.87 mL, 1.74 mmol), $NaH_2PO_4.H_2O$ (75 mg, 0.544 mol) and $NaClO_2$ (78.7 mg, 0.87 mmol). The mixture was stirred overnight and partitioned between DCM and 20% citric acid. The aqueous phase was re-extracted with DCM. The combined organic phases were dried over sodium sulfate and evaporated to furnish 125 mg of carboxylic acid.

Step 5

To a solution of carboxylic acid product from Step 4 (125 mg, 0.236 mmol) in THF (3 mL) was added 1 N TBAF solution in THF (0.54 mL, 0.54 mmol). The mixture was stirred at RT overnight, diluted with 20% citric acid and extracted with ethyl acetate to furnish 125 mg of crude hydroxycarboxylic acid.

Step 6

To a mixture of hydroxycarboxylic acid product from Step 5 (60 mg, 0.144 mmol) and 3,8-diaza-bicyclo[3.2.1]octane-8-carboxylic acid tert-butyl ester (61 mg, 0.29 mmol) in DCM (1.0 mL) was added BOP reagent (65 mg, 0.144 mmol) followed by N-methylmorpholine (47 μL, 0.43 mmol). The mixture was stirred at RT for 5 h. The mixture was quenched with brine, extracted with EtOAc and DCM. Combined organic phases were dried over magnesium sulfate and concentrated. The residue was purified by flash-chromatography over silica gel (eluted with 4% MeOH in DCM) to furnish 60 mg of hydroxyamide.

Step 7

To a mixture of hydroxyamide product from Step 6 (60 mg, 0.0984 mmol) in DCM (5 mL) was added 0.5 mL of TFA. The mixture was stirred for 50 minutes and the solvent was removed. The residue was re-dissolved in DCM and washed with 2 N NaOH, water and brine. The organic phase was dried over sodium sulfate, concentrated and purified by prep. TLC over silica gel (eluted with 10% MeOH in DCM) to furnish 37.9 mg of Example 146, as a 2:3 mixture of diastereomers. $^1$H NMR (CDCl$_3$, 400 MHz) δ 7.73 (d, J=8.8 Hz, 0.8H), 7.72 (d, J=8.8 Hz, 1.2H), 7.48 (d, J=8.8 Hz, 2H), 5.29 (br d, 7.3 Hz, 0.4H), 5.14 (br d, 7.3 Hz, 0.6H), 4.18 (d, 11.7 Hz, 0.6H), 4.06-3.88 (ser m, 1.7H), 3.77-3.45 (ser m, 5.8H), 3.40-3.30 (ser m, 2.9H), 3.15 (dd, J=6.6, 11.0 Hz, 0.6H), 2.96 (m, 1H), 2.86 (m, 0.4H), 2.75 (dd, J=5.1, 10.2 Hz, 0.7H), 2.06 (m, 0.4H), 1.87-1.51 (ser m, 8H), 1.14-1.03 (ser m, 1H), 0.84-0.65 (ser m, 5.4H), 0.56 (m, 0.4H), 0.47 (m, 0.6H), 0.26 (m, 1H); LCMS (M+H$^+$) m/z=510.3, retention time 2.65 min (single peak).

Example 147 exo-alpha-[1-[4-[(4-chlorophenyl)sulfonyl]-5(r)-cyclopropyl-3(s)-morpholinyl]cyclopropyl]-beta-oxo-3-(1-piperidinyl)-8-azabicyclo[3.2.1]octane-8-ethanol

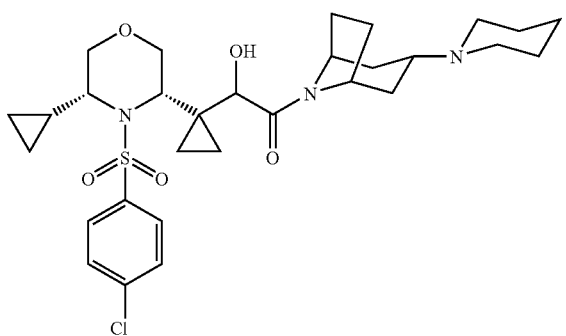

Example 147

The compound of Example 147 was prepared following procedures similar to those of Example 146. LCMS (M+H$^+$) m/z=592.3, retention time 3.11 min.

Assay:

The pharmacological properties of the compounds of this invention may be evaluated by a number of pharmacological assays. The exemplified pharmacological assays, which are described later, have been carried out with the compounds according to the present invention, as well as with salts thereof.

Gamma-secretase activity was determined as described by Zhang et al. (*Biochemistry*, 40 (16), 5049-5055, 2001), which is herein incorporated by reference. Activity is expressed either as a percent inhibition or as the concentration of compound producing 50% inhibition of enzyme activity.

Reagents. Antibodies W02, G2-10, and G2-11 were obtained from Dr. Konrad Beyreuther (University of Heidelberg, Heidelberg, Germany). W02 recognizes residues 5-8 of Aβ peptide, while G2-10 and G2-11 recognize the specific C-terminal structure of Aβ 40 and Aβ42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction. The construct SPC99-Ion, which contains the first 18 residues and the C-terminal 99 amino acids of APP carrying the London mutation, has been described (Zhang, L., Song, L., and Parker, E. (1999) *J. Biol. Chem.* 274, 8966-8972). Upon insertion into the membrane, the 17 amino acid signal peptide is processed, leaving an additional leucine at the N-terminus of Aβ. SPC99-Ion was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for Aβ production by inducing C99 expression with 0.1 g/mL tetracycline for 16-20 h and analyzing conditioned media with a sandwich immunoassay (see below). One of the clones, designated as pTRE.15, was used in these studies.

Membrane Preparation. C99 expression in cells was induced with 0.1 g/mL tetracycline for 20 h. The cells were pretreated with 1 M phorbol 12-myristate 13-acetate (PMA) and 1 M brefeldin A (BFA) for 5-6 h at 37° C. before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70 C before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70° C.

γ-Secretase Reaction and Aβ Analysis. To measure γ-secretase activity, membranes were incubated at 37° C. for 1 h in 50 μL of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2-10 and biotin-W02, while Aβ 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

The compounds of Examples 4, 34, 90 and 91 had an IC$_{50}$ higher than about 1 μM. All other compounds from the other Examples had an IC$_{50}$ within the range of about 1 nM to about 1 μM. The compounds of Examples 2, 15, 16, 30, 35, 36, 43, 47, 51, 59, 69, 75, 78, 88, 94, 98, 99, 110, 122, 135, 142, 146 had an IC$_{50}$ within the range of about 1 nM to about 25 nM, i.e., 6.8, 3.6, 1.4, 11.1, 9.5, 13.3, 7.9, 24.5, 6.2, 8.9, 5.2, 0.9, 3.9, 6.7, 2.1, 3.6, 0.9, 5.7, 4.2, 4.2, 12.4 and 10.1, respectively.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

The invention claimed is:

1. A compound of the formula I:

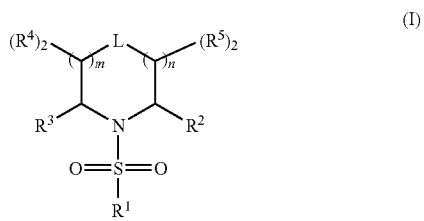

or a pharmaceutically acceptable salt thereof, wherein:

L is —O—;

R¹ is selected from the group consisting of unsubstituted thienyl and thienyl substituted with one or more substituents R⁷ which can be the same or different;

R² is cycloalkylene-X—C(O)—Y;

R³ is selected from the group consisting of unsubstituted aryl, aryl substituted with one or more substituents R⁷ which can be the same or different, unsubstituted heteroaryl, heteroaryl substituted with one or more substituents R⁷ which can be the same or different, unsubstituted alkyl, alkyl substituted with one or more substituents R⁷ which can be the same or different, unsubstituted cycloalkyl, cycloalkyl substituted with one or more substituents R⁷ which can be the same or different, alkylene-cycloalkyl, alkylene-cycloalkyl independently substituted on the cycloalkyl moiety with one or more substituents R⁷, unsubstituted arylalkyl, arylalkyl optionally independently substituted on the aryl moiety with one or more substituents R⁷ which can be the same or different, unsubstituted arylcycloalkyl, arylcycloalkyl independently substituted on the aryl moiety with one or more substituents R⁷ which can be the same or different, unsubstituted heteroarylalkyl, heteroarylalkyl independently substituted on the heteroaryl moiety with one or more substituents R⁷ which can be the same or different, unsubstituted heteroarylcycloalkyl, heteroarylcycloalkyl independently substituted on the heteroaryl moiety with one or more substituents R⁷ which can be the same or different, unsubstituted arylheterocycloalkyl, arylheterocycloalkyl independently substituted on the aryl moiety with one or more substituents R⁷ which can be the same or different, and unsubstituted alkoxyalkyl;

each R⁴ and R⁵ is independently selected from the group consisting of H, alkyl, and alkyl independently substituted with one or more substituents R⁷ which can be the same or different; or R³ and R⁴ together with the carbon atoms to which they are shown attached can be linked to form a 4- to 8-membered cycloalkyl or heterocycloalkyl ring;

R⁷ is selected from the group consisting of halo, —CF₃, —OH, alkyl, alkyl substituted with 1 to 4 hydroxy groups, —O-alkyl, —OCF₃, —CN, —NH(alkyl), —N(alkyl)₂, —NH(aryl), —N(aryl)₂, —N(aryl)(alkyl), —C(O)O-alkyl, -alkylene-NH(alkyl), -alkylene-N(alkyl)₂, -alkylene-NH(aryl), -alkylene-N(aryl)₂, -alkylene-N(aryl)(alkyl), —NHC(O)-alkyl, —N(alkyl)C(O)-alkyl, —N(aryl)C(O)-alkyl, —NHC(O)-aryl, —N(alkyl)C(O)-aryl, —N(aryl)C(O)-aryl, —NHC(O)-heteroaryl, —N(alkyl)C(O)-heteroaryl, —N(aryl)C(O)-heteroaryl, —NHC(O)—NH₂, —NHC(O)—NH(alkyl), —NHC(O)—N(alkyl)₂, —NHC(O)—NH(aryl), —NHC(O)—N(aryl)₂, —NHC(O)—N(alkyl)(aryl), —N(alkyl)C(O)—NH₂, —N(alkyl)C(O)—NH(alkyl), —N(alkyl)C(O)—N(alkyl)₂, —N(alkyl)C(O)—NH(aryl), —N(alkyl)C(O)—N(aryl)₂, —N(alkyl)C(O)—N(alkyl)(aryl), —N(aryl)C(O)—NH₂, —N(aryl)C(O)—NH(alkyl), —N(aryl)C(O)—N(alkyl)₂, —N(aryl)C(O)—NH(aryl), —N(aryl)C(O)—N(aryl)₂, and —N(aryl)C(O)—N(alkyl)(aryl);

R⁸ and R⁹ are each independently selected from the group consisting of H, alkyl, cycloalkyl, arylalkyl, heteroarylalkyl,

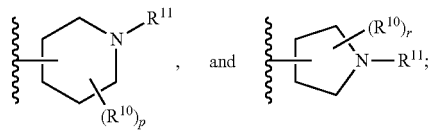

each R¹⁰ is independently selected from the group consisting of H, —OH, alkyl, alkyl substituted with 1 to 4 hydroxy groups, —O-alkyl, —O-alkyl substituted with 1 to 4 hydroxy groups, cycloalkyl, cycloalkyl substituted with 1 to 4 hydroxy groups, —C(O)O-alkyl, -alkylene-C(O)—OH, unsubstituted heterocycloalkyl, heterocycloalkyl substituted with one or more groups R⁷, -alkylene-C(O)—NH₂, -alkylene-C(O)—NH(alkyl), -alkylene-C(O)—N(alkyl)₂, -alkylene-C(O)—NH(aryl), -alkylene-C(O)—N(aryl)₂, -alkylene-C(O)—N(alkyl)(aryl), —C(O)—NH₂, —C(O)—NH(alkyl), —C(O)—N(alkyl)₂, —C(O)—NH(aryl), —C(O)—N(aryl)₂, —C(O)—N(alkyl)(aryl), —O-cycloalkyl, and —O-cycloalkyl substituted with 1 to 4 hydroxy groups; or two R¹⁰ groups together with the ring carbon atoms to which they are shown attached form a 4- to 7-membered cycloalkyl or heterocycloalkyl ring; or two R¹⁰ groups together with the ring carbon atom to which they are attached form a carbonyl group;

R¹¹ is H, alkyl, alkyl substituted with 1 to 4 hydroxy groups, cycloalkyl, cycloalkyl substituted with 1 to 4 hydroxy groups, arylalkyl, heteroarylalkyl, —C(O)O-alkyl, —C(O)-alkyl, —C(O)-alkyl wherein said alkyl moiety is substituted with one or more hydroxyl groups, —C(O)-cycloalkyl, —C(O)—NH₂, —C(O)—NH(alkyl), —C(O)—N(alkyl)₂, —C(O)—NH(aryl), —C(O)—N(aryl)₂, —C(O)—N(alkyl)(aryl), —C(O)-alkylene-NH₂, —C(O)-alkylene-NH(alkyl), —C(O)-alkylene-N(alkyl)₂, —C(O)-alkylene-NH(aryl), —C(O)-alkylene-N(aryl)₂, —C(O)-alkylene-N(alkyl)(aryl), —S(O₂)-alkyl, -alkylene-C(O)—OH, alkylene-O-alkylene-OH, unsubstituted aryl, aryl independently substituted with one or more substituents R⁷, unsubstituted heteroaryl, heteroaryl independently substituted with one or more substituents R⁷, and -alkylene-C(O)O-alkyl;

X is —O—;

Y is selected from the group consisting of unsubstituted heteroaryl, heteroaryl independently substituted with one or more substituents R⁷ which may be the same or different, unsubstituted heterocycloalkyl, heterocycloalkyl independently substituted with one or more substituents R⁷ which may be the same or different, unsubstituted arylheterocycloalkyl, and arylheterocycloalkyl independently substituted on the aryl moiety with one or more substituents R⁷ which may be the same or different; or Y is selected from the group consisting of:

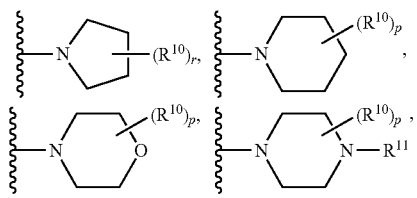

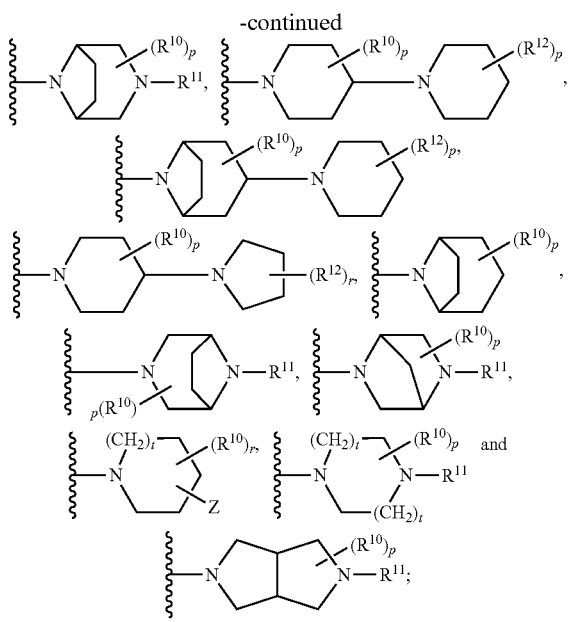

Z is selected from the group consisting of H, —OH, —O-alkyl, unsubstituted heterocycloalkyl, heterocycloalkyl optionally independently substituted with one or more substituents $R^{14}$ which may be the same or different, —$NR^8R^9$, —$NR^8R^{13}$, unsubstituted benzo-fused heterocycloalkyl, and benzo-fused heterocycloalkyl optionally independently substituted on the benzo- or heterocycloalkyl moiety with one or more substituents $R^{14}$ which may be the same or different;

each $R^{12}$ is independently H or alkyl;

$R^{13}$ is selected from the group consisting of H, unsubstituted heterocycloalkyl, heterocycloalkyl independently substituted with one or more substituents $R^{14}$ which may be the same or different, unsubstituted arylalkyl, arylalkyl independently substituted on the aryl moiety with one or more substituents $R^{14}$ which may be the same or different, unsubstituted heteroarylalkyl, heteroarylalkyl optionally independently substituted on the heteroaryl moiety with one or more substituents $R^{14}$ which may be the same or different, unsubstituted cycloalkyl, cycloalkyl optionally independently substituted with one or more substituents $R^{14}$ which may be the same or different, unsubstituted -alkylene-cycloalkyl, -alkylene-cycloalkyl independently substituted on the cycloalkyl moiety with one or more substituents $R^{14}$ which may be the same or different, unsubstituted-alkylene-heterocycloalkyl, and -alkylene-heterocycloalkyl independently substituted on the heterocycloalkyl moiety with one or more substituents $R^{14}$ which may be the same or different;

$R^{14}$ is selected from the group consisting of halo, —$CF_3$, —OH, —O-alkyl, —$OCF_3$, —CN, —$NR^8R^9$, —C(O)-alkyl, —C(O)-aryl, —C(O)—$NR^8R^9$, —C(O)O-alkyl, -alkylene-$NR^8R^9$, -alkylene-C(O)O-alkyl, —$N(R^8)C(O)$-alkyl, —$N(R^8)C(O)$-aryl, —$N(R^8)C(O)$-heteroaryl, —$N(R^8)C(O)$—$NR^8R^9$, piperidinyl, pyrrolidinyl, aryl, heteroaryl, and —O—$CH_2$—$CH_2$—O—, wherein both oxygen atoms of said —O—$CH_2$—$CH_2$—O— are bound to the same carbon atom and with the proviso that aryl and heteroaryl moieties are not substituted with said —O—$CH_2$—$CH_2$—O— group;

m is 1 and n is 1;

p is an integer of from 1 to 4;

r is an integer of from 1 to 3; and t is an integer of from 0 to 2.

2. The compound of claim 1, or a pharmaceutically acceptable salt thereof, wherein:

$R^1$ is thienyl substituted with one or more substituents $R^7$; and $R^3$ is aryl, alkyl, alkylene-cycloalkyl or cycloalkyl, each of which may be unsubstituted or substituted with one or more substituents $R^7$ which can be the same or different.

3. The compound of claim 1, or a pharmaceutically acceptable salt thereof, wherein $R^2$ is -1,1-cyclopropylene-O—C(O)—Y.

4. The compound of claim 1, or a pharmaceutically acceptable salt thereof, wherein $R^3$ is selected from the group consisting of 3,5-difluorophenyl, cyclopropyl, methyl, ethyl, isopropyl, n-propyl, —$CH_2$-cyclopropyl, —$CH_2$-(2,2-difluorocyclopropyl).

5. The compound of claim 1, or a pharmaceutically acceptable salt thereof, wherein Y is selected from the group consisting of

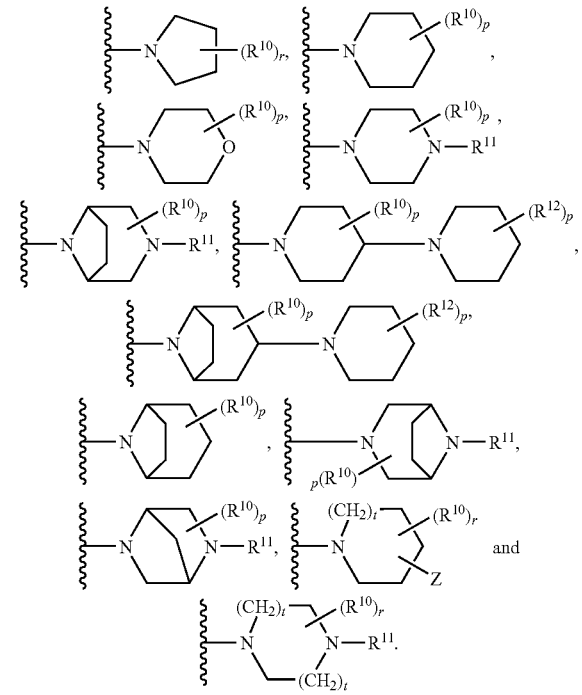

6. The compound of claim 1, or a pharmaceutically acceptable salt thereof, selected from the group consisting of:

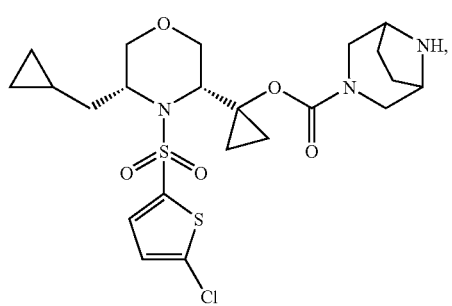

-continued

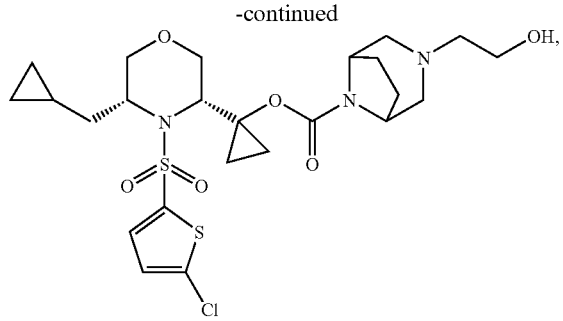

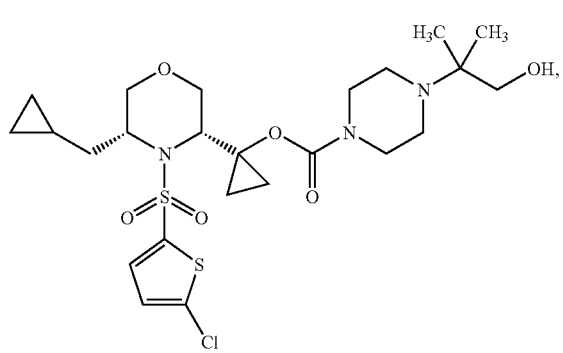

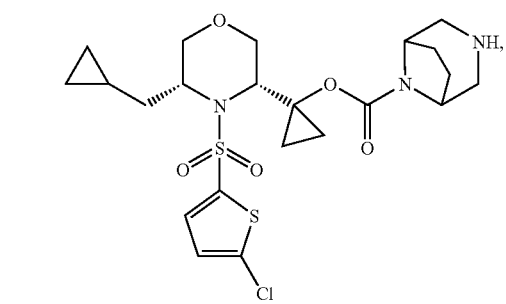

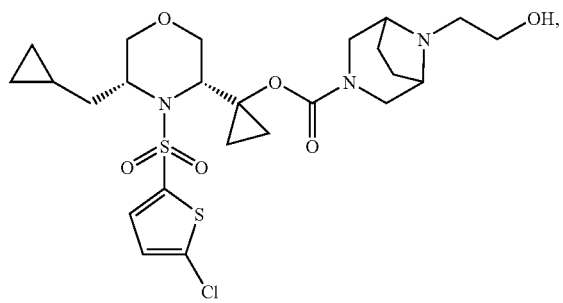

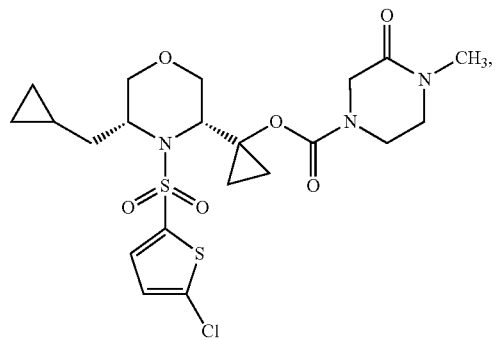

-continued

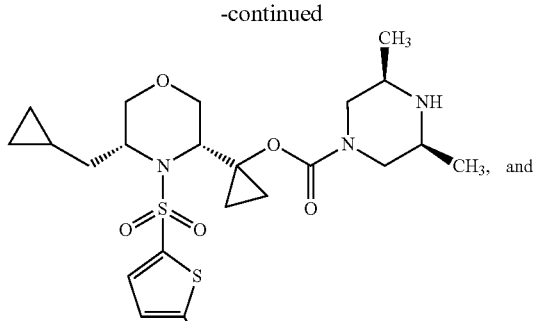

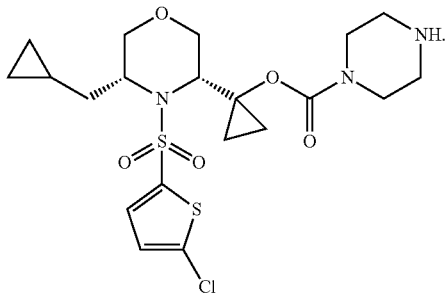

7. A pharmaceutical composition comprising at least one compound of claim 1, or a pharmaceutically acceptable salt thereof and at least one pharmaceutically acceptable carrier.

8. The compound of claim 1, or a pharmaceutically acceptable salt thereof, in purified form.

9. The compound of claim 6, or a pharmaceutically acceptable salt thereof, wherein the compound is:

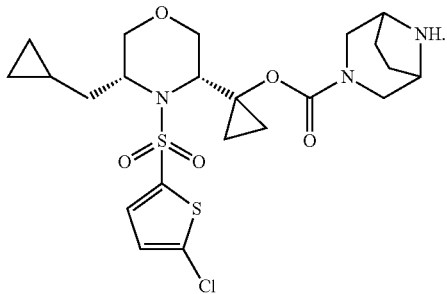

10. The compound of claim 6, or a pharmaceutically acceptable salt thereof, wherein the compound is:

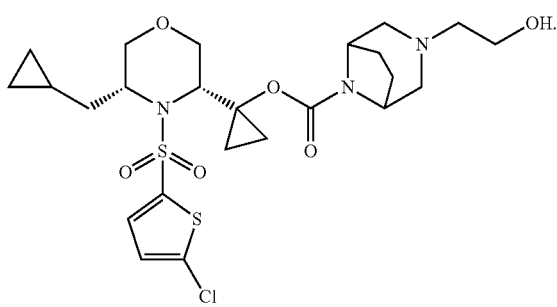

11. The compound of claim 6, or a pharmaceutically acceptable salt thereof, wherein the compound is:

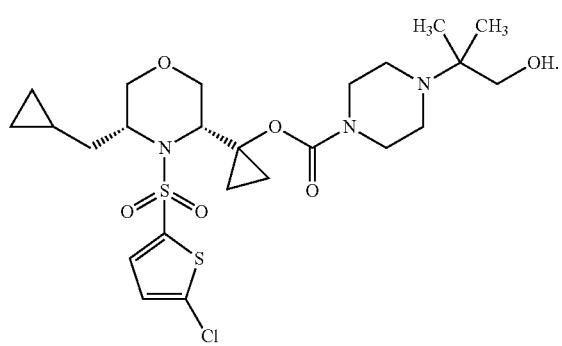

12. The compound of claim 6, or a pharmaceutically acceptable salt thereof, wherein the compound is:

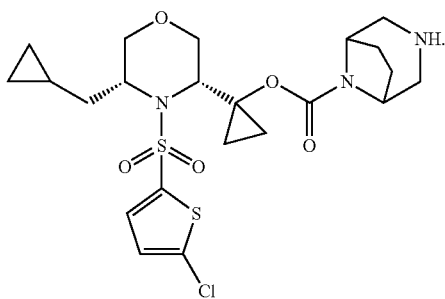

13. The compound of claim 6, or a pharmaceutically acceptable salt thereof, wherein the compound is:

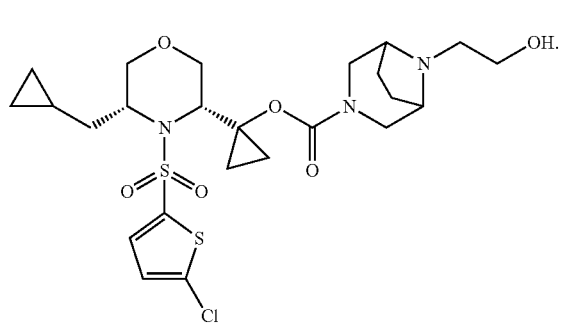

14. The compound of claim 6, or a pharmaceutically acceptable salt thereof, wherein the compound is:

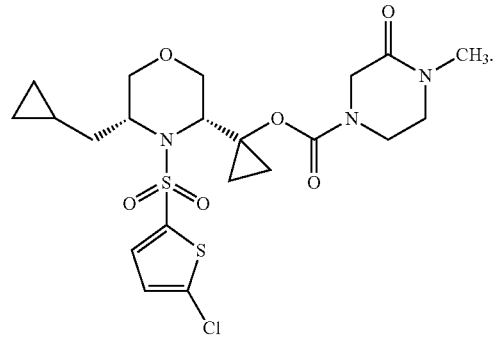

15. The compound of claim 6, or a pharmaceutically acceptable salt thereof, wherein the compound is:

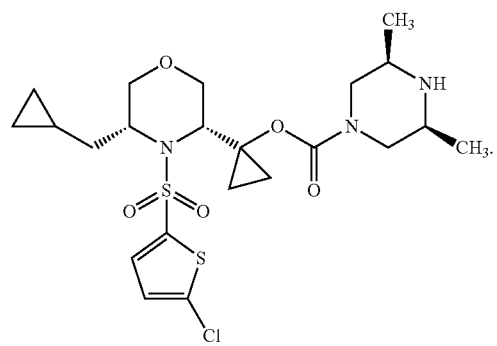

16. The compound of claim 6, or a pharmaceutically acceptable salt thereof, wherein the compound is:

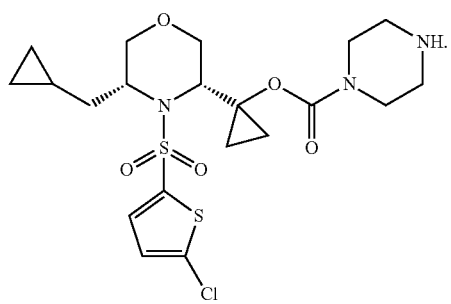

* * * * *